(12) United States Patent
Bigg et al.

(10) Patent No.: US 6,339,091 B1
(45) Date of Patent: *Jan. 15, 2002

(54) COMPTOTHECIN ANALOGUES, PREPARATION METHODS THEREFOR, USE THEREOF AS DRUGS, AND PHARMACEUTICAL COMPOSITIONS CONTAINING SAID ANALOGUES

(75) Inventors: Dennis Bigg, Gif-sur-Yvette; Olivier Lavergne, Massy, both of (FR); Francesc Pla Rodas, Santa Coloma de Farners (ES); Jacques Pommier, Colombes (FR); Gerard Ulibarri, Bures-sur-Yvette (FR); Jerry Harnett, Gif-sur-Yvette (FR); Alain Rolland, Palaiseau (FR); Anne-Marie Liberatore, Auffargis (FR); Christophe Lanco, Dourdan (FR); Jean-Bernard Cazaux, Aramon (FR); Christine Le Breton, Avignon (FR); Eric Manginot, Montfavet (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/332,520

(22) Filed: Jun. 14, 1999

Related U.S. Application Data

(63) Continuation-in-part of application No. 08/973,561, filed as application No. PCT/FR96/00980 on Jun. 21, 1996, application No. 09/332,520, which is a continuation-in-part of application No. PCT/FR98/01768, filed on Aug. 7, 1998, and a continuation-in-part of application No. PCT/FR97/02218, filed on Dec. 5, 1997, and a continuation-in-part of application No. PCT/FR97/02217, filed on Dec. 5, 1997.

(30) Foreign Application Priority Data

Jun. 21, 1995 (GB) ............................... 9512670
Dec. 20, 1996 (FR) ............................. 96 15774
Dec. 20, 1996 (FR) ............................. 96 15775
Dec. 24, 1996 (FR) ............................. 96 15945
Aug. 29, 1997 (FR) ............................. 97 10785

(51) Int. Cl.$^7$ ................... C07D 491/14; C07D 491/22; C07D 471/04; A61K 31/47
(52) U.S. Cl. ........................ 514/283; 546/48
(58) Field of Search ........................ 546/48; 514/283

(56) References Cited

FOREIGN PATENT DOCUMENTS

WO        WO 94/11376        * 5/1994

* cited by examiner

Primary Examiner—Bruck Kifle
(74) Attorney, Agent, or Firm—Bierman, Muserlian and Lucas

(57) ABSTRACT

The compound of the formula

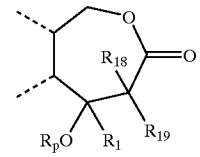

wherein the substituents are defined as in the specification and its non-toxic, pharmaceutically acceptable salts which are useful for the treatment of viral infections, parasitic diseases and the treatment of cancer.

10 Claims, No Drawings

COMPTOTHECIN ANALOGUES, PREPARATION METHODS THEREFOR, USE THEREOF AS DRUGS, AND PHARMACEUTICAL COMPOSITIONS CONTAINING SAID ANALOGUES

PRIOR APPLICATIONS

This application is a continuation-in-part of U.S. patent application Ser. No. 973,561 filed Dec. 2, 1997 which is the 371 of PCT/FR96/00980 filed Jun. 21, 1996 and the 371 of PCT/FR97/02217 filed Dec. 5, 1997, PCT/FR97/02218 filed Dec. 5, 1991 and PCT/FR98/01768 filed Aug. 7, 1998.

Camptothecin is a natural compound which has been isolated for the first time from the leaves and the bark of the Chinese plant called *camptotheca acuminata* (see Wall et al. J. Amer. Chem. Soc. 88:3888 (1966)). Camptothecin is a pentacyclic compound constituted by an idolizing[1,2-b] quinoline fragment fused with an α-hydroxylactone with six members. The carbon in position 20 which carries the α-hydroxy group is asymmetrical and confers a rotatory power on the molecule. The natural form of camptothecin has an absolute "S" configuration as regards the carbon 20 and corresponds to the following formula:

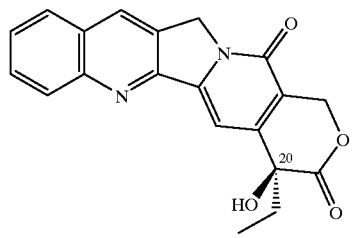

Camptothecin has an anti-proliferative activity in several cancerous cell lines, including the cell lines of human tumors of the colon, lung and breast (Suffness, M et al: The Alkaloids Chemistry and Pharmacology, Bross A., ed., Vol. 25, p. 73 (Acedemic Press, 1985)). It is suggested that the anti-proliferative activity of camptothecin is related to its inhibitory activity on DNA topoisomerase I.

It has been indicated that α-hydroxylactone was an absolute requirement both for the in vivo and in vitro activity of campotothecin (Camptothecins: New Anticancer Agents, Putmesil, M et al, ed., p. 27 (CRC Press, 1995); Wall M. et al, Cancer Res. 55:753 (1995); Hertzberg et al, J. Med. Chem. 32:715 (1982) and Crow et al, J. Med. Chem. 35:4160 (1992)). The present invention relates to a new class of compounds of camptothecin, in which a β-hydroxylactone replaces the natural α-hydroxylactone of camptothecin. The compounds according to the present invention present a powerful biological activity which is unexpected with regard to the state of the prior art.

Therefore a subject of the invention is new analogues of camptothecin which differ from all known derivatives of camptothecin in the sense that they contain β-hydroxylactone (or its open hydroxycarboxylic form) instead of an α-hydroxylactone (or its open hydroxycarboxylic form); or a pharmaceutically acceptable salt of one of the latter. By derivative of camptothecin is meant a compound having the same structural skeleton as that of camptothecin (i.e. an indolizino[1,2-b]quinoline fragment fused with an α-hydroxylactone with six members), with or without other chemical substitutions on the skeletal structure. Different derivatives of camptothecin are well known by specialists, as described hereafter. By β-hydroxylactone is meant a lactone which contains an additional carbon atom between the carbon of the carboxyl and the α-carbon carrying the hydroxyl group in the α-hydroxylactone.

An analogue of camptothecin according to the invention can therefore contain substitutions on the indolizino[1,2-b] quinoline fragment (for example in order to improve the solubility of the compound), or on the open or closed β-hydroxylactone (for example in order to improve the stability of the compound). Examples of substitutions on the closed β-hydroxylactone include an alkyl substitution (for example ethyl) on the β-carbon. Examples of substitutions on the open β-hydroxylactone include alkyl substitutions on the β-carbon, substitutions (for example an amidation) on the resultant carboxylic acid and substitutions (for example an esterification) or suppressions of the resultant hydroxyl group.

Preferred β-hydroxylactone camptothecin analogues are notably those in which the pentacyclic skeleton is substituted at least once by an halogen atom in any of positions 9, 10, 11 or 12.

The invention first relates to compounds of general formula (B1) and (B2)

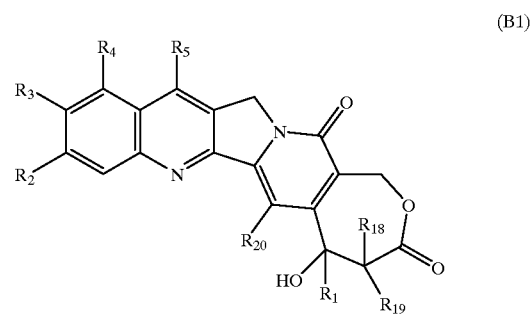

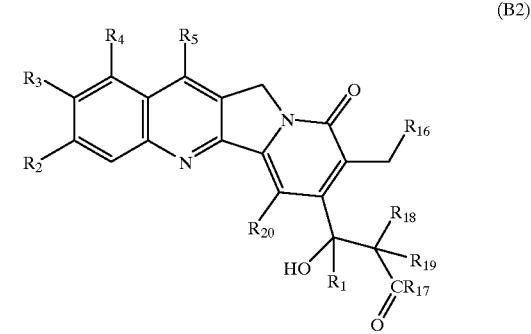

in racemic or enantiomeric form or any combinations of these forms, in which $R_1$ represents a lower alkyl, a lower alkenyl, a lower alkynyl, a lower haloalkyl, a lower alkoxy lower alkyl or lower alkylthio lower alkyl;

$R_2$, $R_3$ and $R_4$ represent, independently, H, halo, lower haloalkyl, lower alkyl, lower alkenyl, cyano, lower cyanoalkyl, nitro, lower nitroalkyl, amido, lower amidoalkyl, hydrazino, lower hydrazinoalkyl, azido, lower azidoalkyl, $(CH_2)_mNR_6R_7$, $(CH_2)_mOR_6$, $(CH_2)_mSR_6$, $(CH_2)_mCO_2R_6$, $(CH_2)_mNR_6C(O)R_8$, $(CH_2)_mC(O)R_8$, $(CH_2)_mOC(O)R_8$, $O(CH_2)_mNR_6R_7$, $OC(O)NR_6R_7$, $OC(O)(CH_2)_mCO_2R_6$ or $(CH_2)n[N=X]$, $OC(O)[N=X]$, $(CH_2)_mOC(O)[N=X]$ (in which [N=X], in this invention, represents a heterocyclic group with 4 to 7 members with the nitrogen atom N, which is a member of the heterocyclic group, and X represents the remaining members, which are necessary to complete the beterocylic group, selected from the group constituted by O, S, $CH_2$, CH, N, $NR_9$ and $COR_{10}$), substituted or non substituted aryl or lower arylalkyl (i.e. substituted between once and four times on the aryl group or the heterocycle), in which the substituent is a lower alkyl, halo, nitro, amino, lower alkylamino, lower haloalkyl, lower hydroxyalkyl, lower alkoxy or lower alkoxy lower alkyl) or $R_2$ and $R_3$ form together a chain with 3 or 4 members in which the elements of the chain are selected from the group constituted by CH, $CH_2$, O, S, N or $NR_9$;

$R_5$ represents H, halo, lower haloalkyl, lower alkyl, lower alkoxy, lower alkoxy lower alkyl, lower alkylthio lower alkyl, cycloalkyl, cycloalkyl lower alkyl, cyano, cyanoalkyl, lower alkyl lower sulphonylalkyl, lower hydroxyalkyl, nitro, $(CH_2)_mC(O)R_8$, $(CH_2)_mNR_6C(O)R_8$, $(CH_2)_mNR_6R_7$, $(CH_2)_mN(CH_3)(CH_2)_nNR_6R_7$, $(CH_2)_mOC(O)R_8$, $(CH_2)_mOC(O)NR_6R_7$, $(CH_2)_mS(O)_qR_{11}$, $(CH_2)_mP(O)R_{12}R_{13}$, $(CH_2)_2P(S)R_{12}R_{13}$ or $(CH_2)_n[N=X]$, $OC(O)[N=X]$, $(CH_2)_mOC(O)[N=X]$, substituted or non substituted aryl or lower arylalkyl (i.e. substituted between once and four times on the aryl or heteroaryl group), in which the substituent is a lower alkyl, halo, hydroxy, nitro, amino, lower alkylamino, lower haloalkyl, lower hydroxyalkyl, lower alkoxy or lower alkoxy lower alkyl;

$R_6$ and $R_7$ represent, independently, H, a lower alkyl, lower hydroxyalkyl, lower alkyl lower aminoalkyl, lower aminoalkyl, cycloalkyl, cycloalkyl lower alkyl, lower alkenyl, lower alkoxy lower alkyl, lower haloalkyl, or substituted or non substituted aryl or lower arylalkyl (i.e. substituted between once and four times on the aryl group), in which the substituent is a lower alkyl, halo, nitro, amino, lower alkylamino, lower haloalkyl, lower hydroxyalkyl, lower alkoxy or lower alkoxy lower alkyl;

$R_8$ represents H, a lower alkyl, lower hydroxyalkyl, amino, lower alkylamino, lower alkyl lower aminoalkyl, lower aminoalkyl, cycloalkyl, cycloalkyl lower alkyl, lower alkenyl, lower alkoxy, lower alkoxy lower alkyl, lower haloalkyl, or substituted or non substituted aryl or lower arylalkyl (i.e. substituted between once and four times on the aryl group), in which the substituent is a lower alkyl, halo, nitro, amino, lower alkylamino, lower haloalkyl, lower hydroxyalkyl, lower alkoxy or lower alkoxy lower alkyl;

$R_9$ represents H, a lower alkyl, lower haloalkyl, aryl, lower arylalkyl, or aryl or lower arylalkyl in which the aryl group is substituted by one or more groups chosen from the following radicals: lower alkyl, halo, nitro, amino, lower alkylamino, lower haloalkyl, lower hydroxyalkyl, lower alkoxy or lower alkoxy lower alkyl;

$R_{10}$ represents H, a lower alkyl, lower haloalkyl, lower alkoxy, aryl or aryl substituted (i.e. having one to four substituents on the aryl group) by one or more groups chosen from the following radicals: lower alkyl, lower haloalkyl, lower hydroxyalkyl or lower alkoxy lower allyl;

$R_{11}$ represents a lower alkyl, aryl, $(CH_2)_mOR_{14}$, $(CH_2)_mSR_{14}$, $(CH_2)_2NR_{14}R_{15}$ or $(CH_2)_m[N=X]$;

$R_{12}$ and $R_{13}$ represent, independently, a lower alkyl, aryl, lower alkoxy, aryloxy or amino;

$R_{14}$ and $R_{15}$ represent, independently, H, lower alkyl or aryl;

$R_{16}$ represents H or $OR_{21}$;

$R_{17}$ represents $OR_6$ or $NR_6R_7$;

$R_{18}$ and $R_{19}$ represent, independently, H, halo, lower alkyl, lower alkoxy or hydroxy;

$R_{20}$ represents H or halo;

$R_{21}$ represents H, a lower alkyl, CHO or $C(O)(CH_2)_mCH_3$;

$R_p$ represents H or an easily cleavable group preferably chosen from the groups corresponding to the formula —C(O)—A—$NR_{22}R_{23}$, in which A represents a linear or branched alkylene radical optionally substituted by a radical chosen from the free, esterified or salified hydroxy, halogen, free, esterified or salified carboxy, amino, mono or dialkylamino radicals, while $R_{22}$ and $R_{23}$, independently, represent H, a lower alkyl, lower hydroxyalkyl, lower alkyl lower aminoalkyl, lower aminoalkyl, cycloalkyl, cycloalkyl lower alkyl, lower alkenyl, lower alkoxy lower alkyl, lower haloalkyl, or substituted or non substituted aryl or lower arylalkyl (i.e., substituted one to four times on the aryl group), in which the substituent is a lower alkyl, halo, nitro, amino, lower alkylamino, lower haloalkyl, lower hydroxyalkyl, lower alkoxy or lower alkoxy lower alkyl;

m is an integer comprised between 0 and 6;

n is 1 or 2; and q represents an integer from 0 to 2; and

[N=X] represents a heterocyclic group with 4 to 7 members, X representing the chain necessary to complete said heterocyclic group and selected from the group constituted by O, S, $CH_2$, CH, N, $NR_9$ and $COR_{10}$:

or pharmaceutically acceptable salts of the latter.

The invention especially relates to compounds of general formula (HCPT)

(HCPT)

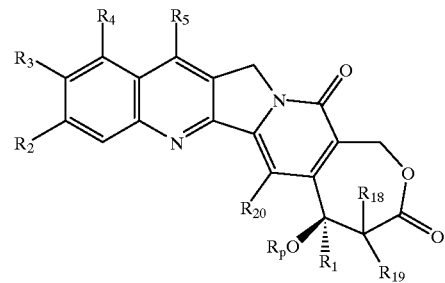

in racemic or enantiomeric form or any combinations of these forms, in which $R_1$ represents a lower alkyl, a lower alkenyl, a lower alkynyl, a lower haloalkyl, a lower alkoxy lower alkyl or lower alkylthio lower alkyl;

$R_2$, $R_3$ and $R_4$ represent, independently, H, halo, lower haloalkyl, lower alkyl, lower alkenyl, cyano, lower cyanoalkyl, nitro, lower nitroalkyl, amido, lower amidoalkyl, hydrazino, lower hydrazinoalkyl, azido, lower azidoalkyl, $(CH_2)_mNR_6R_7$, $(CH_2)_mOR_6$, $(CH_2)_mSR_6$, $(CH_2)_mCO_2R_6$, $(CH_2)_mNR_6C(O)R_8$, $(CH_2)_mC(O)R_8$, $(CH_2)_mOC(O)R_8$, $O(CH_2)_mNR_6R_7$, $OC(O)NR_6R_7$, $OC(O)(CH_2)_mCO_2R_6$ or $(CH_2)_n[N=X]$, $OC(O)[N=X]$, $(CH_2)_mOC(O)[N=X]$ (in which [N=X], in this invention, represents a heterocyclic group with 4 to 7 members with the nitrogen atom N, which is a member of the heterocyclic group, and X represents the remaining members, which are necessary to complete the heterocyclic group, selected from the group constituted by O, S, $CH_2$, CH, N, $NR_9$ and $COR_{10}$), substituted or non substituted aryl or lower arylalkyl (i.e. substituted between once and four times on the aryl group or the heterocycle), in which the substituent is a lower alkyl, halo, nitro, amino, lower alkylamino, lower haloalkyl, lower hydroxyalkyl, lower alkoxy or lower alkoxy lower alkyl) or $R_2$ and $R_3$ form together a chain with 3 or 4 members in which the elements of the chain are selected from the group constituted by CH, $CH_2$, O, S, N or $NR_9$;

$R_5$ represents H, halo, lower haloalkyl, lower alkyl, lower alkoxy, lower alkoxy lower alkyl, lower alkylthio lower alkyl, cycloalkyl, cycloalkyl lower alkyl, cyano, cyanoalkyl, lower alkyl lower sulphonylalkyl, lower hydroxyalkyl, nitro, $(CH_2)_mC(O)R_8$, $(CH_2)_mNR_6C(O)R_8$, $(CH_2)_mNR_6R_7$, $(CH_2)_mN(CH_3)(CH_2)_nNR_6R_7$, $(CH_2)_mOC(O)R_8$, $(CH_2)_mOC(O)NR_6R_7$, $(CH_2)_mS(O)_qR_{11}$, $(CH_2)_mP(O)R_{12}R_{13}$, $(CH_2)_2P(S)R_{12}R_{13}$, substituted or non-substituted $(CH_2)_n[N=X]$ radical, $OC(O)[N=X]$, $(CH_2)_mOC(O)[N=X]$, substituted or non substituted aryl or lower arylalkyl (i.e. substituted between once and four times on the aryl or heteroaryl group), in which the substituent is a lower alkyl, halo, hydroxy, nitro, amino, lower alkylamino, lower haloalkyl, lower hydroxyalkyl, lower alkoxy or lower alkoxy lower alkyl;

$R_6$ and $R_7$ represent, independently, H, a lower alkyl, lower hydroxyalkyl, lower alkyl lower aminoalkyl, lower aminoalkyl, cycloalkyl, cycloalkyl lower alkyl, lower alkenyl, lower alkoxy lower alkyl, lower haloalkyl, or substituted or non substituted aryl or lower arylalkyl (i.e. substituted between once and four times on the aryl group), in which the substituent is a lower allyl, halo, nitro, amino, lower alkylamino, lower haloalkyl, lower hydroxyalkyl, lower alkoxy or lower alkoxy lower alkyl;

$R_8$ represents H, a lower alkyl, lower hydroxyalkyl, amino, lower alkylamino, lower alkyl lower aminoalkyl, lower aminoalkyl, cycloalkyl, cycloalkyl lower alkyl, lower alkenyl, lower alkoxy, lower alkoxy lower alkyl, lower haloalkyl, or substituted or non substituted aryl or lower arylalkyl (i.e. substituted between once and four times on the aryl group), in which the substituent is a lower alkyl, halo, nitro, amino, lower alkylamino, lower haloalkyl, lower hydroxyalkyl, lower alkoxy or lower alkoxy lower alkyl;

$R_9$ represents H, a lower alkyl, lower haloalkyl, aryl, lower arylalkyl, or aryl or lower arylalkyl in which the aryl group is substituted by one or more groups chosen from the following radicals: lower alkyl, halo, nitro, amino, lower alkylamino, lower haloalkyl, lower hydroxyalkyl, lower alkoxy or lower alkoxy lower alkyl;

$R_{10}$ represents H, a lower alkyl, lower haloalkyl, lower alkoxy, aryl or aryl substituted (i.e. having one to four substituents on the aryl group) by one or more groups chosen from the following radicals: lower alkyl, lower haloalkyl, lower hydroxyalkyl or lower alkoxy lower alkyl;

$R_{11}$ represents a lower alkyl, aryl, $(CH_2)_mOR_{14}$, $(CH_2)_mSR_{14}$, $(CH_2)_2NR_{14}R_{15}$ or $(CH_2)_m[N=X]$;

$R_{12}$ and $R_{13}$ represent, independently, a lower alkyl, aryl, lower alkoxy, aryloxy or amino;

$R_{14}$ and $R_{15}$ represent, independently, H, lower alkyl or aryl;

$R_{16}$ represents H or $OR_{21}$;

$R_{17}$ represents $OR_6$ or $NR_6R_7$;

$R_{18}$ and $R_{19}$ represent, independently, H, halo, lower alkyl, lower alkoxy or hydroxy;

$R_{20}$ represents H or halo;

$R_{21}$ represents H, a lower alkyl, CHO or $C(O)(CH_2)_mCH_3$;

$R_p$ represents H or an easily cleavable group preferably chosen from the groups corresponding to the formula —C(O)—A—$NR_{22}R_{23}$, in which A represents a linear or branched alkylene radical optionally substituted by a radical chosen from the free, esterified or salified hydroxy, halogen, free, esterified or salified carboxy, amino, mono or dialkylamino radicals, while $R_{22}$ and $R_{23}$, independently, represent H, a lower alkyl, lower hydroxyalkyl, lower alkyl lower aminoalkyl, lower aminoalkyl, cycloalkyl, cycloalkyl lower alkyl, lower alkenyl, lower alkoxy lower alkyl, lower haloalkyl, or substituted or non substituted aryl or lower arylalkyl (i.e., substituted one to four times on the aryl group), in which the substituent is a lower alkyl, halo, nitro, amino, lower alkylamino, lower haloalkyl, lower hydroxyalkyl, lower alkoxy or lower alkoxy lower alkyl;

m is an integer comprised between 0 and 6;

n is 1 or 2; and q represents an integer from 0 to 2; and

[N=X] represents a heterocyclic group with 4 to 7 members, X representing the chain necessary to complete said heterocyclic group and selected from the group constituted by O, S, $CH_2$, CH, N, $NR_9$ and $COR_{10}$;

or pharmaceutically acceptable salts of the latter.

For the compounds of general formulae (B1), (B2) and (HCPT) (and in extenso the compounds of general formulae (I) and (II)), the following preferences apply independently to the substituents:

$R_1$ represents a lower alkyl, and preferably ethyl;

$R_2$ represents halo;

$R_3$ represents halo, lower alkyl or lower haloalkyl; when $R_3$ is a lower alkyl, $R_3$ is preferably methyl or ethyl;

$R_5$ represents halo, lower alkyl, lower haloalkyl, lower aminoalkyl, substituted or non substituted $(CH_2)_n[N=X]$ radical, substituted or non substituted aryl or lower arylalkyl; preferred $(CH_2)_n[N=X]$ radicals include lower alkyl, and piperazines, especially methyl substituted piperazines;

$R_{18}$ and $R_{19}$ represent H.

$R_{20}$ represents H.

The invention particularly relates to the following compounds which are described as examples of compounds responding to the general formula (B1) or the general formula (B2):

tert-butyl 3-hydroxy-3-[8-(hydroxymethyl)-9-oxo-9,11-dihydroindolizino[1,2-b]quinolin-7-yl]pentanoate;

ethyl 3-hydroxy-3-[8-(hydroxymethyl)-9-oxo-9,11-dihydroindolizino[1,2-b]quinolin-7-yl]pentanoate;

5-ethyl-5-hydroxy-1,4,5,13-tetrahydro-3H,15H-oxepino[3',4':6,7]indolizino[1,2-b]quinoline-3,15-dione;

3-hydroxy-3-[8-(hydroxymethyl)-9-oxo-9,11-dihydroindolizino[1,2-b]quinolin-7-yl]pentanoic acid;

methyl 3-hydroxy-3-[8-(methoxymethyl)-9-oxo-9,11-dihydroindolizino[1,2-b]quinolin-7-yl]pentanoate;

ethyl 2,2-difluoro-3-hydroxy-3-[8-(hydroxymethyl)-9-oxo-9,11-dihydroindolizino[1,2-b]quinolin-7-yl]pentanoate;

ethyl 3-hydroxy-3-(8-methyl-9-oxo-9,11-dihydroindolizino[1,2-b]quinolin-7-yl)pentanoate;

tert-butyl 3-{8-[(acetyloxy)methyl]-9-oxo-9,11-dihydroindolizino[1,2-b]quinolin-7-yl}-3-hydroxypentanoate;

5,12-diethyl-5-hydroxy-1,4,5,13-tetrahydro-3H,15H-oxepino[3',4':6,7]indolizino[1,2-b]quinoline-3,15-dione;

3-[12-ethyl-8-(hydroxymethyl)-9-oxo-9,11-dihydroindolizino[1,2-b]quinolin-7-yl]-3-hydroxypentanoic acid;

8-ethyl-8-hydroxy-2,3,8,9,12,15-hexahydro-(10H,13H-[1,4]dioxino[2,3-g]oxepino[3',4':6,7]indolizino[1,2-b]quinoline-10,13-dione;

10-(benzyloxy)-5-ethyl-5-hydroxy-1,4,5,13-tetrahydro-3H,15H-oxepino[3',4':6,7]indolizino[1,2-b]quinoline-3,15-dione;

3-[2-(benzyloxy)-8-(hydroxymethyl)-9-oxo-9,11-dihydroindolizino[1,2-b]quinolin-7-yl]-3-hydroxypentanoic acid (E);

5-ethyl-5,10-dihydroxy-1,4,5,13-tetrahydro-3H,15H-oxepino[3',4':6,7]indolizino[1,2-b]quinoline-3,15-dione;

11-[(dimethylamino)methyl]-5-ethyl-5,10-dihydroxy-1,4,5,13-tetrahydro-3H,15H-oxepino[3',4':6,7]indolizino[1,2-b]quinoline-3,15-dione;

5-ethyl-9-fluoro-5-hydroxy-10methoxy-1,4,5,13-tetrahydro-3H,15H-oxepino[3',4':6,7]indolizino[1,2-b]quinoline-3,15-dione;

9-chloro-5-ethyl-5-hydroxy-10-methyl-1,4,5,13-tetrahydro-3H,15H-oxepino[3',4':6,7]indolizino[1,2-b]quinoline-3,15-dione;

5-ethyl-9,10-difluoro-5-hydroxy-1,4,5,13-tetrahydro-3H,15H-oxepino[3',4':6,7]indolizino[1,2-b]quinoline-3,15-dione;

7-ethyl-7-hydroxy-7,8,11,14-tetrahydro-9H,12H-[1,3]dioxolo[4,5-g]oxepino[3',4':6,7]indolizino[1,2-b]quinoline-9,12-dione;

9-chloro-5-ethyl-5-hydroxy-10-methoxy-1,4,5,13-tetrahydro-3H,15H-oxepino[3',4':6,7]indolizino[1,2-b]quinoline-3,15-dione;

5-ethyl-5-hydroxy-10-methoxy-1,4,5,13-tetrahydro-3H,15H-oxepino[3',4':6,7]indolizino[1,2-b]quinoline-3,15-dione;

9,11-dichloro-5-ethyl-5-hydroxy-1,4,5,13-tetrahydro-3H,15H-oxepino[3',4':6,7]indolizino[1,2-b]quinoline-3,15-dione;

5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-10-fluoro-5-hydroxy-1,4,5,13-tetrahydro-3H,15H-oxepino[3',4':6,7]indolizino[1,2-b]quinoline-3,15-dione;

10-chloro-5-ethyl-5-hydroxy-1,4,5,13-tetrahydro-3H,15H-oxepino[3',4':6,7]indolizino[1,2-b]quinoline-3,15-dione;

9-chloro-5-ethyl-10-fluoro-5-hydroxy-1,4,5,13-tetrahydro-3H,15H-oxepino[3',4':6,7]indolizino[1,2-b]quinoline-3,15-dione;

5-ethyl-5,10-dihydroxy-11-(4-morpholinylmethyl)-1,4,5,13-tetrahydro-3H,15H-oxepino[3',4':6,7]indolizino[1,2-b]quinoline-3,15-dione;

5,12-diethyl-9-fluoro-5-hydroxy-10methoxy-1,4,5,13-tetrahydro-3H,15H-oxepino[3',4':6,7]indolizino[1,2-b]quinoline-3,15-dione;

5-ethyl-5-hydroxy-12-methyl-1,4,5,13-tetrahydro-3H,15H-oxepino[3',4':6,7]indolizino[1,2-b]quinoline-3,15-dione;

9-chloro-5-ethyl-5-hydroxy-10-methoxy-12-[(4-methyl-1-piperazinyl)methyl]-1,4,5,13-tetrahydro-3H,15H-oxepino[3',4':6,7]indolizino[1,2-b]quinoline-3,15-dione;

9-chloro-5-ethyl-5-hydroxy-10-methoxy-12-(4-morpholinylmethyl)-1,4,5,13-tetrahydro-3H,15H-oxepino[3',4':6,7]indolizino[1,2-b]quinoline-3,15-dione;

5-ethyl-5-hydroxy-12-[(4methyl-1-piperazinyl)methyl]-1,4,5,13-tetrahydro-3H,15H-oxepino[3',4':6,7]indolizino[1,2-b]quinoline-3,15-dion;

5-ethyl-5-hydroxy-12-(1-piperidinylmethyl)-1,4,5,13-tetrahydro-3H,15lH-oxepino[3',4':6,7]indolizino[1,2-b]quinoline-3,15-dione;

5-ethyl-5-hydroxy-12-(4-morpholinylmethyl)-1,4,5,13-tetrahydro-3H,15H-oxepino[3',4':6,7]indolizino[1,2-b]quinoline-3,15-dione;

5-ethyl-10-fluoro-5-hydroxy-12-[(4-methyl-1-piperazinyl)methyl]-1,4,5,13-tetrahydro-3H,15H-oxepino[3',4':6,7]indolizino[1,2-b]quinoline-3,15-dione;

5-ethyl-10-fluoro-5-hydroxy-12-(4-morpholinylmethyl)-1,4,5,13-tetrahydro-3H,15H-oxepino[3',4':6,7]indolizino[1,2-b]quinoline-3,15-dione;

5-ethyl-9-fluoro-5-hydroxy-10-methyl-12-[(4-methyl-1-piperazinyl)methyl]-1,4,5,13-tetrahydro-3H,15H-oxepino[3',4':6,7]indolizino[1,2-b]quinoline-3,15-dione;

5-ethyl-9-fluoro-5-hydroxy-10-methyl-12-(4-morpholinylmethyl)-1,4,5,13-tetrahydro-3H,15H-oxepino[3',4':6,7]indolizino[1,2-b]quinoline-3,15-dione;

5-ethyl-9-fluoro-5-hydroxy-10-methyl-12-(1-piperidinylmethyl)-1,4,5,13-tetrahydro-3H,15H-oxepino[3',4':6,7]indolizino[1,2-b]quinoline-3,15-dione;

8-ethyl-8-hydroxy-16-[(4methyl-1-piperazinyl)methyl]-2,3,8,9,12,15-hexahydro-10H,13H-[1,4]dioxino[2,3-g]oxepino[3',4':6,7]indolizino[1,2-b]quinoline-10,13-dione;

9-chloro-5-ethyl-10-fluoro-5-hydroxy-12-(4-morpholinylmethyl)-1,4,5,13-tetrahydro-3H,15H-oxepino[3',4':6,7]indolizino[1,2-b]quinoline-3,15-dione;

12-[3,6-dihydro-1(2H)-pyridinylmethyl]-5-ethyl-9,10-difluoro-5-hydroxy-1,4,5,13-tetrahydro-3H,15H-oxepino[3',4':6,7]indolizino[1,2-b]quinoline-3,15-dione;

5-ethyl-9,10-difluoro-5-hydroxy-12-[(4-methyl-1-piperidinyl)methyl]-1,4,5,13-tetrahydro-3H,15H-oxepino[3',4':6,7]indolizino[1,2-b]quinoline-3,15-dione;

5-ethyl-9,10-difluoro-5-hydroxy-12-(1-pyrrolidinylmethyl)-1,4,5,13-tetrahydro-3H,15H-oxepino[3',4':6,7]indolizino[1,2-b]quinoline-3,15-dione;

5-ethyl-9,10-difluoro-5-hydroxy-12-[(4-methyl-1-piperazinyl)methyl]-1,4,5,13-tetrahydro-3H,15H-oxepino[3',4':6,7]indolizino[1,2-b]quinoline-3,15-dione;

5-ethyl-9,10-difluoro-5-hydroxy-12-(1-piperidinylmethyl)-1,4,5,13-tetrahydro-3H,15H-oxepino[3',4':6,7]indolizino[1,2-b]quinoline-3,15-dione;

12-[(dimethylamino)methyl]-5-ethyl-9,10-difluoro-5-hydroxy-1,4,5,13-tetrahydro-3H,15H-oxepino[3',4':6,7]indolizino[1,2-b]quinoline-3,15-dione;

9-chloro-5-ethyl-5-hydroxy-10-methyl-12-(4-morpholinylmethyl)-1,4,5,13-tetrahydro-3H,15H-oxepino[3',4':6,7]indolizino[1,2-b]quinoline-3,15-dione;

9-chloro-5-ethyl-5-hydroxy-10-methyl-12-[(4-methyl-1-piperazinyl)methyl]-1,4,5,13-tetrahydro-3H,15H-oxepino[3',4':6,7]indolizino[1,2-b]quinoline-3,15-dione;

12-{[benzyl(methyl)amino]methyl}-9-chloro-5-ethyl-5-hydroxy-10-methyl-1,4,5,13-tetrahydro-3H,15H-oxepino[3',4':6,7]indolizino[1,2-b]quinoline-3,15-dione;

12-[(4-benzyl-1-piperazinyl)methyl]-9-chloro-5-ethyl-5-hydroxy-10-methyl-1,4,5,13-tetrahydro-3H,15H-oxepino[3',4':6,7]indolizino[1,2-b]quinoline-3,15-dione;

9-chloro-5-ethyl-5-hydroxy-10-methyl-12-(1-piperidinylmethyl)-1,4,5,13-tetrahydro-3H,15H-oxepino[3',4':6,7]indolizino[1,2-b]quinoline-3,15-dione;

12-[(4-benzyl-1-piperazinyl)methyl]-5-ethyl-10-fluoro-5-hydroxy-1,4,5,13-tetrahydro-3H,15H-oxepino[3',4':6,7]indolizino[1,2-b]quinoline-3,15-dione;

12-[(4-benzyl-1-piperazinyl)methyl]-5-ethyl-9-fluoro-5-hydroxy-10-methyl-1,4,5,13-tetrahydro-3H,15H-oxepino[3',4':6,7]indolizino[1,2-b]quinoline-3,15-dione;

12-[(dimethylamino)methyl]-5-ethyl-9-fluoro-5-hydroxy-10-methyl-1,4,5,13-tetrahydro-3H,15H-oxepino[3',4':6,7]indolizino[1,2-b]quinoline-3,15-dione;

12-[(diethylamino)methyl]-5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-9-fluoro-5-hydroxy-10-methyl-12-[(4-methyl-1-piperidinyl)methyl]-1,4,5,13-tetrahydro-3H,15H-oxepino[3',4':6,7]indolizino[1,2-b]quinoline-3,15-dione;

5-ethyl-9-fluoro-5-hydroxy-10-methyl-12-(1-pyrrolidinylmethyl)-1,4,5,13-tetrahydro-3H,15H-oxepino[3',4':6,7]indolizino[1,2-b]quinoline-3,15-dione;

12-[3,6-dihydro-1(2H)-pyridinylmethyl]-5-ethyl-9-fluoro-5-hydroxy-10-methyl-1,4,5,13-tetrahydro-3H,15H-oxepino[3',4':6,7]indolizino[1,2-b]quinoline-3,15-dione;

12-[(diisobutylamino)methyl]-5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-9-fluoro-5-hydroxy-10-methoxy-12-[(4methyl-1-piperazinyl)methyl]-1,4,5,13-tetrahydro-3H,15H-oxepino[3',4':6,7]indolizino[1,2-b]quinoline-3,15-dione;

5-ethyl-9-fluoro-5-hydroxy-10-methoxy-12-(1-piperidinylmethyl)-1,4,5,13-tetrahydro-3H,15H-oxepino[3',4':6,7]indolizino[1,2-b]quinoline-3,15-dione;

9-chloro-12-[(dimethylamino)methyl]-5-ethyl-5-hydroxy-10-methoxy-1,4,5,13-tetrahydro-3H,15H-oxepino[3',4':6,7]indolizino[1,2-b]quinoline-3,15-dione;

9-chloro-5-ethyl-5-hydroxy-10-methoxy-12-(1-piperidinylmethyl)-1,4,5,13-tetrahydro-3H,15H-oxepino[3',4':6,7]indolizino[1,2-b]quinoline-3,15-dione;

12-[3,6-dihydro-1(2H)-pyridinylmethyl]-5-ethyl-5-hydroxy-10methoxy-1,4,5,13-tetrahydro-3H,15H-oxepino[3',4':6,7]indolizino[1,2-b]quinoline-3,15-dione;

5-ethyl-5-hydroxy-10-methoxy-12-[(4-methyl-1-piperidinyl)methyl]-1,4,5,13-tetrahydro-3H,15H-oxepino[3',4':6,7]indolizino[1,2-b]quinoline-3,15-dione;

5-ethyl-5-hydroxy-10-methoxy-12-[(4-methyl-1-piperazinyl)methyl]-1,4,5,13-tetrahydro-3H,15H-oxepino[3',4':6,7]indolizino[1,2-b]quinoline-3,15-dione;

5-ethyl-5-hydroxy-10-methoxy-12-(1-pyrrolidinylmethyl)-1,4,5,13-tetrahydro-3H,15H-oxepino[3',4':6,7]indolizino[1,2-b]quinoline-3,15-dione;

12-[(4-benzyl-1-piperazinyl)methyl]-5-ethyl-5-hydroxy-10-methoxy-1,4,5,13-tetrahydro-3H,15H-oxepino[3',4':6,7]indolizino[1,2-b]quinoline-3,15-dione;

9-chloro-5-ethyl-5-hydroxy-10-methyl-12-[(4-methyl-1-piperidinyl)methyl]-1,4,5,13-tetrahydro-3H,15H-oxepino[3',4':6,7]indolizino[1,2-b]quinoline-3,15-dione;

10-(benzyloxy)-5-ethyl-9-fluoro-5-hydroxy-1,4,5,13-tetrahydro-3H,15H-oxepino[3',4':6,7]indolizino[1,2-b]quinoline-3,15-dione;

5-ethyl-9-fluoro-5,10-dihydroxy-1,4,5,13-tetrahydro-3H,15H-oxepino[3',4':6,7]indolizino[1,2-b]quinoline-3,15-dione;

5-ethyl-9,10-difluoro-3,15-dioxo-4,5,13,15-tetrahydro-1H,3H-oxepino[3',4':6,7]indolizino[1,2-b]quinolin-5-yl 2-aminoacetate;

5-ethyl-9,10-difluoro-3,15-dioxo-4,5,13,15-tetrahydro-1H,3H-oxepino[3',4':6,7]indolizino[1,2-b]quinolin-5-yl 3-aminopropanoate;

2,9-diethyl-9-hydroxy-1,2,3,9,10,16-hexahydro-13H-[1,3]oxazino[5,6-f]oxepino[3',4':6,7]indolizino[1,2-b]quinoline-11,14-dione;

9-ethyl-9-hydroxy-2-methyl-1,2,3,9,10,16-hexahydro-13H-[1,3]oxazino[5,6-f]oxepino[3',4':6,7]indolizino[1,2-b]quinoline-11,14-dione;

2-benzyl-9-ethyl-9-hydroxy-1,2,3,9,10,16-hexahydro-13H-[1,3]oxazino[5,6-f]oxepino[3',4':6,7]indolizino[1,2-b]quinoline-11,14-dione;

2-benzyl-9-ethyl-5-fluoro-9-hydroxy-1,2,3,9,10,16-hexahydro-13H-[1,3]oxazino[5,6-f]oxepino[3',4':6,7]indolizino[1,2-b]quinoline-11,14-dione;

(+)-5-ethyl-9,10-difluoro-5-hydroxy-4,5,13,15-tetrahydro-1H,3H-oxepino[3',4':6,7]indolizino[1,2-b]quinoline-3,15-dione;

(+)-1-[9-chloro-5-ethyl-5-hydroxy-10-methyl-3,15-dioxo-4,5,13,15-tetrahydro1H,3H-oxepino[3',4':6,7]

indolizino[1,2-b]quinolin-12-ylmethyl]-4-methylhexahydropyridine;

or a pharmaceutically acceptable salt of the latter.

The invention more particularly relates to the following compounds corresponding to the formula (HCPT):

5-ethyl-5-hydroxy-1,4,5,13-tetrahydro-3H,15H-oxepino[3',4':6,7]indolizino[1,2-b]quinoline-3,15-dione;

5,12-diethyl-5-hydroxy-1,4,5,13-tetrahydro-3H,15H-oxepino[3',4':6,7]indolizino[1,2-b]quinoline3,15-dione;

8-ethyl-8-hydroxy-2,3,8,9,12,15-hexahydro-10H,13H-[1,4]dioxino[2,3-g]oxepino[3',4':6,7]indolizino[1,2-b]quinoline-10,13-dione;

10-(benzyloxy)-5-ethyl-5-hydroxy-1,4,5,13-tetrahydro-3H,15H-oxepino[3',4':6,7]indolizino[1,2-b]quinoline-3,15-dione;

5-ethyl-5,10-dihydroxy-1,4,5,13-tetrahydro-3H,15H-oxepino[3',4':6,7]indolizino[1,2-b]quinoline-3,15-dione;

11-[(dimethylamino)methyl]-5-ethyl-5,10-dihydroxy-1,4,5,13-tetrahydro-3H,15H-oxepino[3',4':6,7]indolizino[1,2-b]quinoline-3,15-dione;

5-ethyl-9-fluoro-5-hydroxy-10-methoxy-1,4,5,13-tetrahydro-3H,15H-oxepino[3',4':6,7]indolizino[1,2-b]quinoline-3,15-dione;

9-chloro-5-ethyl-5-hydroxy-10-methyl-1,4,5,13-tetrahydro-3H,15H-oxepino[3',4':6,7]indolizino[1,2-b]quinoline-3,15-dione;

5-ethyl-9,10-difluoro-5-hydroxy-1,4,5,13-tetrahydro-3H,15H-oxepino[3',4':6,7]indolizino[1,2-b]quinoline-3,15-dione;

7-ethyl-7-hydroxy-7,8,11,14-tetrahydro-9H,12M-[1,3]dioxolo[4,5-g]oxepino[3',4':6,7]indolizino[1,2-b]quinoline-9,12-dione;

9-chloro-5-ethyl-5-hydroxy-10-methoxy-1,4,5,13-tetrahydro-3H,15H-oxepino[3',4':6,7]indolizino[1,2-b]quinoline-3,15-dione;

5-ethyl-5-hydroxy-10-methoxy-1,4,5,13-tetrahydro-3H,15H-oxepino[3',4':6,7]indolizino[1,2-b]quinoline-3,15-dione;

9,11-dichloro-5-ethyl-5-hydroxy-1,4,5,13-tetrahydro-3H,15-oxepino[3',4':6,7]indolizino[1,2-b]quinoline-3,15-dione;

5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-10-fluoro-5-hydroxy-1,4,5,13-tetrahydro-3H,15H-oxepino[3',4':6,7]indolizino[1,2-b]quinoline-3,15-dione;

10-chloro-5-ethyl-5-hydroxy-1,4,5,13-tetrahydro-3H,15H-oxepino[3',4':6,7]indolizino[1,2-b]quinoline-3,15-dione;

9-chloro-5-ethyl-10-fluoro-5-hydroxy-1,4,5,13-tetrahydro-3H,15H-oxepino[3',4':6,7]indolizino[1,2-b]quinoline-3,15-dione;

5-ethyl-5,10-dihydroxy-11-(4-morpholinylmethyl)-1,4,5,13-tetrahydro-3H,15H-oxepino[3',4':6,7]indolizino[1,2-b]quinoline-3,15-dione;

5,12-diethyl-9-fluoro-5-hydroxy-10-methoxy-1,4,5,13-tetrahydro-3H,15H-oxepino[3',4':6,7]indolizino[1,2-b]quinoline-3,15-dione;

5-ethyl-5-hydroxy-12-methyl-1,4,5,13-tetrahydro-3H,15H-oxepino[3',4:6,7]indolizino[1,2-b]quinoline-3,15-dione;

9-chloro-5-ethyl-5-hydroxy-10-methoxy-12-[(4-methyl-1-piperazinyl)methyl]-1,4,5,13-tetrahydro-3H,15H-oxepino[3',4':6,7]indolizino[1,2-b]quinoline-3,15-dione;

9-chloro-5-ethyl-5-hydroxy-10-methoxy-12-(4-morpholinylmethyl)-1,4,5,13-tetrahydro-3H,15H-oxepino[3',4':6,7]indolizino[1,2-b]quinoline-3,15-dione;

5-ethyl-5-hydroxy-12-[(4-methyl-1-piperazinyl)methyl]1,4,5,13-tetrahydro-3H,15H-oxepino[3',4':6,7]indolizino[1,2-b]quinoline-3,15-dione;

5-ethyl-5-hydroxy-12-(1-piperidinylmethyl)-1,4,5,13-tetrahydro-3H,15H-oxepino[3',4':6,7]indolizino[1,2-b]quinoline-3,15-dione;

5-ethyl-5-hydroxy-12-(4-morpholinylmethyl)-1,4,5,13-tetrahydro-3H,15H-oxepino[3',4':6,7]indolizino[1,2-b]quinoline-3,15-dione;

5-ethyl-10-fluoro-5-hydroxy-12-[4-methyl-1-piperazinyl)methyl]-1,4,5,13-tetrahydro-3H,15H-oxepino[3',4':6,7]indolizino[1,2-quinoline-3,15-dione;

5-ethyl-10-fluoro-5-hydroxy-12-(4-morpholinoethyl)-1,4,5,13-tetrahydro-3H,15H-oxepino3',4':6,7]indolizino[1,2-b]quinoline-3,15-dione;

5-ethyl-9-fluoro-5-hydroxy-10-methyl-12-[(4-methyl-1-piperazinyl)methyl[1,4,5,13-tetrahydro-3H,15H-oxepino[3',4':6,7]indolizino[1,2-b]quinoline-3,15-dione;

5-ethyl-9-fluoro-5-hydroxy-10-methyl-12-(4-morpholinylmethyl)-1,4,5,13-tetrahydro-3H,15H-oxepino[3',4':6,7]indolizino[1,2-b]quinoline-3,15-dione;

5-ethyl-9-fluoro-5-hydroxy-10-methyl-12-(1-piperidinylmethyl)-1,4,5,13-tetrahydro-3H,15H-oxepino[3',4':6,7]indolizino[1,2-b]quinoline-3,15-dione;

8-ethyl-8-hydroxy-16-[(4-methyl-1-piperazinyl)methyl]-2,3,8,9,12,15-hexahydro-10H,13H-[1,4]dioxino[2,3-g]oxepino[3',4':6,7]indolizino[1,2-b]quinoline-10,13-dione;

9-chloro-5-ethyl-10-fluoro-5-hydroxy-12-(4-morpholinylmethyl)-1,4,5,13-tetrahydro-3H,15H-oxepino[3',4':6,7]indolizino[1,2-b]quinoline-3,15-dione;

12-[3,6-dihydro-1(2H)-pyridinylmethyl]-5-ethyl-9,10-difluoro-5-hydroxy-1,4,5,13-tetrahydro-3H,15H-oxepino[3',4':6,7]indolizno[1,2-b]quinoline-3,15-dione;

5-ethyl-9,10-difluoro-5-hydroxy-12-[(4-methyl-1-piperidinyl)methyl]1,4,5,13-tetrahydro-3H,15H-oxepino[3',4':6,7]indolizino[1,2-b]quinoline-3,15-dione;

5-ethyl-9,10-difluoro-5-hydroxy-12-(1-pyrrolidinylmethyl)-1,4,5,13-tetrahydro-3H,15H-oxepino[3',4':6,7]indolizino[1,2-b]quinoline-3,15-dione;

5-ethyl-9,10-difluoro-5-hydroxy-12-[(4-methyl-1-piperazinyl)methyl]1,4,5,13-tetrahydro-3H,15H-oxepino[3',4':6,7]indolizino[1,2-b]quinoline-3,15-dione;

5-ethyl-9,10-difluoro-5-hydroxy-12-(1-piperidinylmethyl)-1,4,5,13-tetrahydro-3H,15H-oxepino[3',4':6,7]indolizino[1,2-b]quinoline-3,15-dione;

12-[(dimethylamino)methyl]-5-ethyl-9,10-difluoro-5-hydroxy-1,4,5,13-tetrahydro-3H,15H-oxepino[3',4':6,7]indolizino[1,2-b]quinoline-3,15-dione;

9-chloro-5-ethyl-5-hydroxy-10-methyl-12-(4-morpholinylmethyl)-1,4,5,13-tetrahydro-3H,15H-oxepino[3',4':6,7]indolizino[1,2-b]quinoline-3,15-dione;

9-chloro-5-ethyl-5-hydroxy-10-methyl-12-[(4-methyl-1-piperazinyl)methyl]1,4,5,13-tetrahydro-3H,15H-oxepino[3',4':6,7]indolizino[1,2-b]quinoline-3,15-dione;

12-{[benzyl(methyl)amino]methyl}-9-chloro-5-ethyl-5-hydroxy-10-methyl-1,4,5,13-tetrahydro-3H,15H-oxepino[3',4':6,7]indolizino[1,2-b]quinoline-3,15-dione;

12-[(4-benzyl-1-piperazinyl)methyl]9-chloro-5-ethyl-5-hydroxy-10-methyl-1,4,5,13-tetrahydro-3H,15H-oxepino[3',4':6,7]indolizino[1,2-b]quinoline-3,15-dione;

9-chloro-5-ethyl-5-hydroxy-10-methyl-12-(1-piperidinylmethyl)-1,4,5,13-tetrahydro-3H,15H-oxepino[3',4':6,7]indolizino[1,2-b]quinoline-3,15-dione;

12-[(4-benzyl-1-piperazinyl)methyl]5-ethyl-10-fluoro-5-hydroxy-1,4,5,13-tetrahydro-3H,15H-oxepino[3',4':6,7]indolizino[1,2-b]quinoline-3,15-dione;

12-[(4-benzyl-1-piperazinyl)methyl]5-ethyl-9-fluoro-5-hydroxy-10-methyl-1,4,5,13-tetrahydro-3H,15H-oxepino[3',4':6,7]indolizino[1,2-b]quinoline-3,15-dione;

12-[(dimethylamino)methyl]-5-ethyl-9-fluoro-5-hydroxy-10-methyl-1,4,5,13-tetrahydro-3H,15H-oxepino[3',4':6,7]indolizino[1,2-b]quinoline-3,15-dione;

12-[(diethylamino)methyl]-5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-9-fluoro-5-hydroxy-10-methyl-12-[(4-methyl-1-piperidinyl)methyl]1,4,5,13-tetrahydro-3H,15H-oxepino[3',4':6,7]indolizino[1,2-b]quinoline-3,15-dione;

5-ethyl-9-fluoro-5-hydroxy-10-methyl-12-(1-pyrrolidinylmethyl)-1,4,5,13-tetrahydro-3H,15H-oxepino[3',4':6,7]indolizino[1,2-b]quinoline-3,15-dione;

12-[3,6-dihydro-1(2H)-pyridinylmethyl]5-ethyl-9-fluoro-5-hydroxy-10-methyl-1,4,5,13-tetrahydro-3H,15H-oxepino[3',4':6,7]indolizino[1,2-b]quinoline-3,15-dione;

12-[(diisobutylamino)methyl]-5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-9-fluoro-5-hydroxy-10-methoxy-12-[(4-methyl-1-piperazinyl)methyl]-1,4,5,13-tetrahydro-3H,15H-oxepino[3',4':6,7]indolizino[1,2-b]quinoline-3,15-dione;

5-ethyl-9-fluoro-5-hydroxy-10-methoxy-12-(1-piperidinylmethyl)-1,4,5,13-tetrahydro-3H,15H-oxepino[3',4':6,7]indolizino[1,2-b]quinoline-3,15-dione;

9-chloro-12-[(dimethylamino)methyl]-5-ethyl-5-hydroxy-10-methoxy-1,4,5,13-tetrahydro-3H,15H-oxepino[3',4':6,7]indolizino[1,2-b]quinoline-3,15-dione;

9-chloro-5-ethyl-5-hydroxy-10-methoxy-12-(1-piperidinylmethyl)-1,4,5,13-tetrahydro-3H,15H-oxepino[3',4':6,7]indolizino[1,2-b]quinoline-3,15-dione;

12-[3,6-dihydro-1(2H)-pyridinylmethyl]-5-ethyl-5-hydroxy-10-methoxy-1,4,5,13-tetrahydro-3H,15H-oxepino[3',4':6,7]indolizino[1,2-b]quinoline-3,15-dione;

5-ethyl-5-hydroxy-10-methoxy-12-[(4-methyl-1-piperidinyl)methyl]-1,4,5,13-tetrahydro-3H,15H-oxepino[3',4':6,7]indolizino[1,2-b]quinoline-3,15-dione;

5-ethyl-5-hydroxy-10-methoxy-12-[(4-methyl-1-piperazinyl)methyl]1,4,5,13-tetrahydro-3H,15H-oxepino[3',4':6,7]indolizino[1,2-b]quinoline-3,15-dione;

5-ethyl-5-hydroxy-10-methoxy-12-(1-pyrrolidinylmethyl)-1,4,5,13-tetrahydro-3H,15H-oxepino[3',4':6,7]indolizino[1,2-b]quinoline-3,15-dione;

12-[(4-benzyl-1-piperazinyl)methyl]-5-ethyl-5-hydroxy-10-methoxy-1,4,5,13-tetrahydro-3H,15H-oxepino[3',4':6,7]indolizino[1,2-b]quinoline-3,15-dione;

9-chloro-5-ethyl-5-hydroxy-10-methyl-12-[(4-methyl-1-piperidinyl)methyl]-1,4,5,13-tetrahydro-3H,15H-oxepino[3',4':6,7]indolizino[1,2-b]quinoline-3,15-dione;

10-(benzyloxy)-5-ethyl-9-fluoro-5-hydroxy-1,4,5,13-tetrahydro-3H,15H-oxepino[3',4':6,7]indolizino[1,2-b]quinoline-3,15-dione;

5-ethyl-9-fluoro-5,10-dihydroxy-1,4,5,13-tetrahydro-3H,15H-oxepino[3',4':6,7]indolizino[1,2-b]quinoline-3,15-dione;

5-ethyl-9,10-difluoro-3,15-dioxo-4,5,13,15-tetrahydro-1H,3H-oxepino[3',4':6,7]indolizino[1,2-b]quinolin-5-yl2-aminoacetate;

5-ethyl-9,10-difluoro-3,15-dioxo-4,5,13,15-tetrahydro-1H,3H-oxepino[3',4':6,7]indolizino[1,2-b]quinolin-5-yl3-aminopropanoate;

2,9-diethyl-9-hydroxy-1,2,3,9,10,16-hexahydro-13H-[1,3]oxazino[5,6-f]oxepino[3',4':6,7]indolizino[1,2-b]quinoline-11,14-dione;

9-ethyl-9-hydroxy-2-methyl-1,2,3,9,10,16-hexahydro-13H-[1,3]oxazino[5,6-f]oxepino[3',4':6,7]indolizino[1,2-b]quinoline-11,14-dione;

2-benzyl-9-ethyl-9-hydroxy-1,2,3,9,10,16-hexahydro-13H-[1,3]oxazino[5,6-f]oxepino[3',4':6,7]indolizino[1,2-b]quinoline-11,14-dione;

2-benzyl-9-ethyl-5-fluoro-9-hydroxy-1,2,3,9,10,16-hexahydro-13H-[1,3]oxazino[5,6-floxepino[3',4':6,7]indolizino[1,2-b]quinoline-11,14-dione;

(+)-5-ethyl-9,10-difluoro-5-hydroxy-4,5,13,15-tetrahydro-1H,3H-oxepino[3',4':6,7]indolizino[1,2-b]quinoline-3,15-dione;

(+)-1-[9-chloro-5-ethyl-5-hydroxy-10-methyl-3,15-dioxo-4,5,13,15-tetrahydro-1H,3H-oxepino[3',4':6,7]indolizino[1,2-b]quinolin-12-ylmethyl]4-methylhexahydropyridine;

or pharmaceutically acceptable salts of the latter.

Among the above list of compounds, the following are preferred:

5-ethyl-5-hydroxy-1,4,5,13-tetrahydro-3H,15H-oxepino[3',4':6,7]indolizino[1,2-b]quinoline-3,15-dione;

5,12-diethyl-5-hydroxy-1,4,5,13-tetrahydro-3H,15H-oxepino[3',4':6,7]indolizino[1,2-b]quinoline-3,15-dione;

8-ethyl-8-hydroxy-2,3,8,9,12,15-hexahydro-10H,13H-[1,4]dioxino[2,3-g]oxepino[3',4':6,7]indolizino[1,2-b]quinoline-10,13-dione;

5-ethyl-5,10-dihydroxy-1,4,5,13-tetrahydro-3H,15H-oxepino[3',4':6,7]indolizino[1,2-b]quinoline-3,15-dione;

5-ethyl-9-fluoro-5-hydroxy-10-methoxy-1,4,5,13-tetrahydro-3H,15H-oxepino[3',4':6,7]indolizino[1,2-b]quinoline-3,15-dione;

9-chloro-5-ethyl-5-hydroxy-10-methyl-1,4,5,13-tetrahydro-3H,15H-oxepino[3',4':6,7]indolizino[1,2-b]quinoline-3,15-dione;

5-ethyl-9,10-difluoro-5-hydroxy-1,4,5,13-tetrahydro-3H,15H-oxepino[3',4':6,7]indolizino[1,2-b]quinoline-3,15-dione;

7-ethyl-7-hydroxy-7,8,11,14-tetrahydro-9H,12H-[1,3]dioxolo[4,5-g]oxepino[3',4':6,7]indolizino[1,2-b]quinoline-9,12-dione;

9-chloro-5-ethyl-5-hydroxy-10-methoxy-1,4,5,13-tetrahydro-3H,15H-oxepino[3',4':6,7]indolizino[1,2-b]quinoline-3,15-dione;

5-ethyl-5-hydroxy-10-methoxy-1,4,5,13-tetrahydro-3H,15H-oxepino[3',4':6,7]indolizino[1,2-b]quinoline-3,15-dione;

9,11-dichloro-5-ethyl-5-hydroxy-1,4,5,13-tetrahydro-3H,15H-oxepino[3',4':6,7]indolizino[1,2-b]quinoline-3,15-dione;

5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-10-fluoro-5-hydroxy-1,4,5,13-tetrahydro-3H,15H-oxepino[3',4':6,7]indolizino[1,2-b]quinoline-3,15-dione;

10-chloro-5-ethyl-5-hydroxy-1,4,5,13-tetrahydro-3H,15H-oxepino[3',4':6,7]indolizino[1,2-b]quinoline-3,15-dione;

9-chloro-5-ethyl-10-fluoro-5-hydroxy-1,4,5,13-tetrahydro-3H,15H-oxepino[3',4':6,7]indolizino[1,2-b]quinoline-3,15-dione;

5,12-diethyl-9-fluoro-5-hydroxy-10-methoxy-1,4,5,13-tetrahydro-3H,15H-oxepino[3',4':6,7]indolizino[1,2-b]quinoline-3,15-dione;

5-ethyl-5-hydroxy-12-methyl-1,4,5,13-tetrahydro-3H,15H-oxepino[3',4':6,7]indolizino[1,2-b]quinoline-3,15-dione;

5-ethyl-5-hydroxy-12-(4-morpholinylmethyl)-1,4,5,13-tetrahydro-3H,15H-oxepino[3',4':6,7]indolizino[1,2-b]quinoline-3,15-dione;

5-ethyl-9-fluoro-5-hydroxy-10-methyl-12-[(4-methyl-1-piperazinyl)methyl]1,4,5,13-tetrahydro-3H,15H-oxepino[3',4':6,7]indolizino[1,2-b]quinoline-3,15-dione;

5-ethyl-9-fluoro-5-hydroxy-10-methyl-12-(4-morpholinylmethyl)-1,4,5,13-tetrahydro-3H,15H-oxepino[3',4':6,7]indolizino[1,2-b]quinoline-3,15-dione;

5-ethyl-9-fluoro-5-hydroxy-10-methyl-12-(1-piperidinylmethyl)-1,4,5,13-tetrahydro-3H,15H-oxepino[3',4':6,7]indolizino[1,2-b]quinoline-3,15-dione;

12-[3,6-dihydro-1(2H)-pyridinylmethyl]5-ethyl-9,10-difluoro-5-hydroxy-1,4,5,13-tetrahydro-3H,15H-oxepino[3',4':6,7]indolizino[1,2-b]quinoline-3,15-dione;

5-ethyl-9,10-difluoro-5-hydroxy-12-[(4-methyl-1-piperidinyl)methyl]-1,4,5,13-tetrahydro-3H,15H-oxepino[3',4':6,7]indolizino[1,2-b]quinoline-3,15-dione;

5-ethyl-9,10-difluoro-5-hydroxy-12-(1-pyrrolidinylmethyl)-1,4,5,13-tetrahydro-3H,15H-oxepino(3',4':6,7]indolizino[1,2-b]quinoline-3,15-dione;

5-ethyl-9,10-difluoro-5-hydroxy-12-[(4-methyl-1-piperazinyl)methyl]1,4,5,13-tetrahydro-3H,15H-oxepino[3',4':6,7]indolizino[1,2-b]quinoline-3,15-dione;

5-ethyl-9,10-difluoro-5-hydroxy-12-(1-piperidinylmethyl)-1,4,5,13-tetrahydro-3H,15H-oxepino[3',4':6,7]indolizino[1,2-b]quinoline-3,15-dione;

12-[(dimethylamino)methyl]5-ethyl-9,10-difluoro-5-hydroxy-1,4,5,13-tetrahydro-3H,15H-oxepino[3',4':6,7]indolizino[1,2-b]quinoline-3,15-dione;

9-chloro-5-ethyl-5-hydroxy-10-methyl-12-(4-morpholinylmethyl)-1,4,5,13-tetrahydro-3H,15H-oxepino[3',4':6,7]indolizino[1,2-b]quinoline-3,15-dione;

9-chloro-5-ethyl-5-hydroxy-10-methyl-12-[(4-methyl-1-piperazinyl)methyl]1,4,5,13-tetrahydro-3H,15H-oxepino[3',4':6,7]indolizino[1,2-b]quinoline-3,15-dione;

12-[(4-benzyl-1-piperazinyl)methyl]9-chloro-5-ethyl-5-hydroxy-10-methyl-1,4,5,13-tetrahydro-3H,15H-oxepino[3',4':6,7]indolizino[1,2-b]quinoline-3,15-dione;

12-[(diethylamino)methyl]-5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-9-fluoro-5-hydroxy-10-methyl-12-[(4-methyl-1-piperidinyl)methyl]1,4,5,13-tetrahydro-3H,15H-oxepino[3',4':6,7]indolizino[1,2-b]quinoline-3,15-dione;

5-ethyl-9-fluoro-5-hydroxy-10-methyl-12-(1-pyrrolidinylmethyl)-1,4,5,13-tetrahydro-3H,15H-oxepino[3',4':6,7]indolizino[1,2-b]quinoline-3,15-dione;

12-[3,6-dihydro-1(2H)-pyridinylmethyl]5-ethyl-9-fluoro-5-hydroxy-10-methyl-1,4,5,13-tetrahydro-3H,15H-oxepino[3',4':6,7]indolizino[1,2-b]quinoline-3,15-dione;

12-[(diisobutylamino)methyl]5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-9-fluoro-5-hydroxy-10-methoxy-12-(1-piperidinylmethyl)-1,4,5,13-tetrahydro-3H,15H-oxepino[3',4':6,7]indolizino[1,2-b]quinoline-3,15-dione;

9-chloro-12-[(dimethylamino)methyl]5-ethyl-5-hydroxy-10-methoxy-1,4,5,13-tetrahydro-3H,15H-oxepino[3',4':6,7]indolizino[1,2-b]quinoline-3,15-dione;

9-chloro-5-ethyl-5-hydroxy-10-methoxy-12-(1-piperidinylmethyl)-1,4,5,13-tetrahydro-3H,15H-oxepino[3',4':6,7]indolizino[1,2-b]quinoline-3,15-dione;

5-ethyl-5-hydroxy-10-methoxy-12-[(4-methyl-1-piperidinyl)methyl]1,4,5,13-tetrahydro-3H,15H-oxepino[3',4':6,7]indolizino[1,2-b]quinoline-3,15-dione;

9-chloro-5-ethyl-5-hydroxy-10-methyl-12-[(4-methyl-1-piperidinyl)methyl]1,4,5,13-tetrahydro-3H,15H-oxepino[3',4':6,7]indolizino[1,2-b]quinoline-3,15-dione;

5-ethyl-9-fluoro-5,10-dihydroxy-1,4,5,13-tetrahydro-3H, 15H-oxepino[3',4':6,7]indolizino[1,2-b]quinoline-3,15-dione;

2,9-diethyl-9-hydroxy-1,2,3,9,10,16-hexahydro-13H-[1,3]oxazino[5,6-f]oxepino[3',4':6,7]indolizino[1,2-b]quinoline-11,14-dione;

9-ethyl-9-hydroxy-2-methyl-1,2,3,9,10,16-hexahydro-13H-[1,3]oxazino[5,6-f]oxepino[3',4':6,7]indolizino[1,2-b]quinoline-11,14-dione;

2-benzyl-9-ethyl-9-hydroxy-1,2,3,9,10,16-hexahydro-13H-[1,3]oxazino[5,6-f]oxepino[3',4':6,7]indolizino[1,2-b]quinoline-11,14-dione;

2-benzyl-9-ethyl-5-fluoro-9-hydroxy-1,2,3,9,10,16-hexahydro-13H-[1,3]-oxazino[5,6-f]oxepino[3',4':6,7]indolizino[1,2-b]quinoline-11,14-dione;

(+)-5-ethyl-9,10-difluoro-5-hydroxy-4,5,13,15-tetrahydro-1H,3H-oxepino[3',4':6,7]indolizino[1,2-b]quinoline-3,15-dione;

(+)-1-[9-chloro-5-ethyl-5-hydroxy-10-methyl-3,15-dioxo-4,5,13,15-tetrahydro-1H,3H-oxepino[3',4':6,7]indolizino[1,2-b]quinolin-12-ylmethyl]4-methylhexahydropyridine;

or a pharmaceutically acceptable salt of the latter.

Among the above list of compounds, the following are more preferred:

5-ethyl-5-hydroxy-1,4,5,13-tetrahydro-3H,15H-oxepino[3',4':6,7]indolizino[1,2-b]quinoline-3,15-dione;

5,12-diethyl-5-hydroxy-1,4,5,13-tetrahydro-3H,15H-oxepino[3',4':6,7]indolizino[1,2-b]quinoline-3,15-dione;

8-ethyl-8-hydroxy-2,3,8,9,12,15-hexahydro-10H,13H-[1,4]dioxino[2,3-g]oxepino[3',4':6,7]indolizino[1,2-b]quinoline-10,13-dione;

5-ethyl-5,10-dihydroxy-1,4,5,13-tetrahydro-3H,15H-oxepino[3',4':6,7]indolizino[1,2-b]quinoline-3,15-dione;

5-ethyl-9-fluoro-5-hydroxy-10-methoxy-1,4,5,13-tetrahydro-3H,15H-oxepino[3',4':6,7]indolizino[1,2-b]quinoline-3,15-dione;

9-chloro-5-ethyl-5-hydroxy-10-methyl-1,4,5,13-tetrahydro-3H,15H-oxepino[3',4':6,7]indolizino[1,2-b]quinoline-3,15-dione;

5-ethyl-9,10-difluoro-5-hydroxy-1,4,5,13-tetrahydro-3H,15H-oxepino[3',4':6,7]indolizino[1,2-b]quinoline-3,15-dione;

7-ethyl-7-hydroxy-7,8,11,14-tetrahydro-9H,12H-[1,3]dioxolo[4,5-g]oxepino[3',4':6,7]indolizino[1,2-b]quinoline-9,12-dione;

9-chloro-5-ethyl-5-hydroxy-10-methoxy-1,4,5,13-tetrahydro-3H,15H-oxepino[3',4':6,7]indolizino[1,2-b]quinoline-3,15-dione;

5-ethyl-5-hydroxy-10-methoxy-1,4,5,13-tetrahydro-3H,15H-oxepino[3',4':6,7]indolizino[1,2-b]quinoline-3,15-dione;

5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-10-fluoro-5-hydroxy-1,4,5,13-tetrahydro-3H,15H-oxepino[3',4':6,7]indolizino[1,2-b]quinoline-3,15-dione;

10-chloro-5-ethyl-5-hydroxy-1,4,5,13-tetrahydro-3H,15H-oxepino[3',4':6,7]indolizino[1,2-b]quinoline-3,15-dione;

9-chloro-5-ethyl-10-fluoro-5-hydroxy-1,4,5,13-tetrahydro-3H,15H-oxepino[3',4':6,7]indolizino[1,2-b]quinoline-3,15-dione;

5,12-diethyl-9-fluoro-5-hydroxy-10-methoxy-1,4,5,13-tetrahydro-3H,15H-oxepino[3',4':6,7]indolizino[1,2-b]quinoline-3,15-dione;

5-ethyl-5-hydroxy-12-methyl-1,4,5,13-tetrahydro-3H,15H-oxepino[3',4':6,7]indolizino[1,2-b]quinoline-3,15-dione;

5-ethyl-5-hydroxy-12-(4-morpholinylmethyl)-1,4,5,13-tetrahydro-3H,15H-oxepino[3',4':6,7]indolizino[1,2-b]quinoline-3,15-dione;

5-ethyl-9,10-difluoro-5-hydroxy-12-[(4-methyl-1-piperidinyl)methyl-1,4,5,13-tetrahydro-3H,15H-oxepino[3',4':6,7]indolizino[1,2-b]quinoline-3,15-dione;

5-ethyl-9,10-difluoro-5-hydroxy-12-(,5-pyrrolidinylmethyl)-1,4,5,13-tetrahydro-3H,15H-oxepino13',4':6,7]indolizino[1,2-b]quinoline-3,15-dione;

9-chloro-5-ethyl-5-hydroxy-10-methyl-12-(4-morpholinylmethyl)-1,4,5,13-tetrahydro-3H,15H-oxepino[3',4':6,7]indolizino[1,2-b]quinoline-3,15-dione;

9-chloro-5-ethyl-5-hydroxy-10-methyl-2-(4-methyl-1-piperazinyl)methyl]1,4,5,13-tetrahydro-3H,15H-oxepino[3',4':6,7]indolizino[1,2-b]quinoline-3,15-dione;

12-[(diethylamino)methyl]5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-9-fluoro-5-hydroxy-10-methyl-12-[(4-methyl-1-piperidinyl)methyl]1,4,5,13-tetrahydro-3H,15H-oxepino[3',4':6,7]indolizino[1,2-b]quinoline-3,15-dione;

12-[3,6-dihydro-1(2H)-pyridinylmethy]5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-9-fluoro-5-hydroxy-10-methoxy-1-(1-piperidinylmethyl)-1,4,5,13-tetrahydro-3H,15H-oxepino[3',4':6,7]indolizino[1,2-b]quinoline-3,15-dione;

5-ethyl-9-fluoro-5,10-dihydroxy-1,4,5,13-tetrahydro-3H,15H-oxepino[3',4':6,7indolizino[1,2-b]quinoline-3,15-dione;

2,9-diethyl-9-hydroxy-1,2,3,9,10,16-hexahydro-13H-[1,3]oxazino[5,6-f]oxepino[3',4':6,7]indolizino[1,2-b]quinoline-11,14-dione;

9-ethyl-9-hydroxy-2-methyl-1,2,3,9,10,16-hexahydro-13H-[1,3]oxazino[5,6-f]oxepino[3',4':6,7]indolizino[1,2-b]quinoline-11,14-dione;

2-benzyl-9-ethyl-9-hydroxy-1,2,3,9,10,16-hexahydro-13H-[1,3]oxazino[5,6-f]oxepino[3',4':6,7]indolizino[1,2-b]quinoline-11,14-dione;

2-benzyl-9-ethyl-5-fluoro-9-hydroxy-1,2,3,9,10,16-hexahydro-13H-[1,3]oxazino[5,6-f]oxepino[3',4':6,7]indolizino[1,2-b]quinoline-11,14-dione;

(+)-5-ethyl-9,10-difluoro-5-hydroxy-4,5,13,15-tetrahydro-1H,3H-oxepino[3',4':6,7]indolizino[1,2-b]quinoline-3,15-dione;

(+)-1-[9-chloro-5-ethyl-5-hydroxy-10-methyl-3,15-dioxo-4,5,13,15-tetrahydro-1H,3H-oxepino[3',4':6,7]indolizino[1,2-b]quinolin-12-ylmethyl]4-methylhexahydropyridine;

or a pharmaceutically acceptable salt of the latter.

Among the above lists of compounds, particularly preferred compounds for the present invention are the following:

5-ethyl-5-hydroxy-1,4,5,13-tetrahydro-3H,15H-oxepino[3',4':6,7]indolizino[1,2-b]quinoline-3,15-dione;

5-ethyl-5,10-dihydroxy-1,4,5,13-tetrahydro-3H,15H-oxepino[3',4':6,7]indolizino[1,2-b]quinoline-3,15-dione;

5-ethyl-10-fluoro-5-hydroxy-1,4,5,13-tetrahydro-3H,15H-oxepino[3',4':6,7]indolizino[1,2-b]quinoline-3,15-dione;

5-ethyl-9-fluoro-5,10-dihydroxy-1,4,5,13-tetrahydro-3H,15H-oxepino[3',4':6,7]indolizino[1,2-b]quinoline-3,15-dione;

(+)-5-ethyl-9,10-difluoro-5-hydroxy-4,5,13,15-tetrahydro-1H,3H-oxepino[3',4':6,7]indolizino[1,2-b]quinoline-3,15-dione;

(+)-1-[9-chloro-5-ethyl-5-hydroxy-10-methyl-3,15-dioxo-4,5,13,15-tetrahydro-1H,3H-oxepino[3',4':6,7]indolizino[1,2-b]quinolin-12-ylmethyl]4-methylhexahydropyridine;

or a pharmaceutically acceptable salt of the latter.

Among the above lists of compounds, more particularly preferred compounds for the present invention are the following:

(+)-5-ethyl-9,10-difluoro-5-hydroxy-4,5,13,15-tetrahydro-1H,3H-oxepino[3',4':6,7]indolizino[1,2-b]quinoline-3,15-dione;

(+)-1-[9-chloro-5-ethyl-5-hydroxy-10-methyl-3,15-dioxo-4,5,13,15-tetrahydro-1H,3H-oxepino[3',4':6,7]indolizino[1,2-b]quinolin-12-ylmethyl]-4-methylhexahydropyridine;

or a pharmaceutically acceptable salt of the latter.

A more particular subject of the invention is the compounds of general formula (I) and general formula (II),

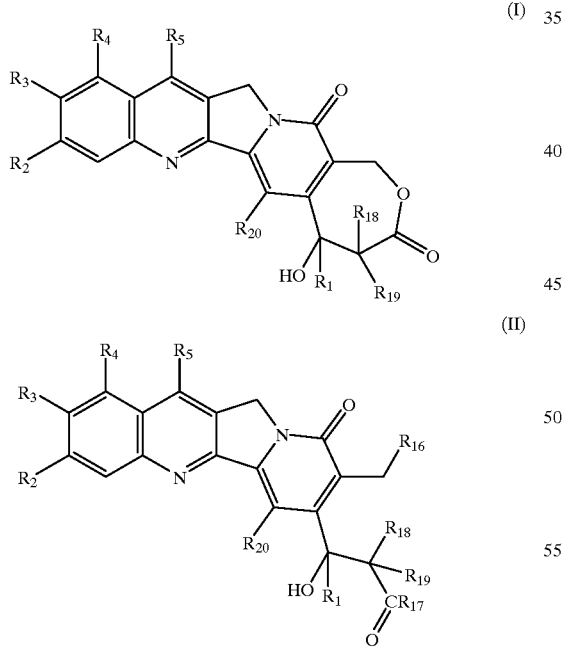

in racemic or enantiomeric form or any combinations of these forms, in which $R_1$ represents a lower alkyl, a lower alkenyl, a lower alkynyl, a lower haloalkyl, a lower alkoxy lower alkyl or lower alkylthio lower alkyl;

$R_2$, $R_3$ and $R_4$ represent, independently, H, halo, lower haloalkyl, lower alkyl, lower alkenyl, cyano, lower cyanoalkyl, nitro, lower nitroalkyl, amido, lower amidoalkyl, hydrazino, lower hydrazinoalkyl, azido, lower azidoalkyl, $(CH_2)_mNR_6R_7$, $(CH_2)_mOR_6$, $(CH_2)_mSR_6$, $(CH_2)_mCO_2R_6$, $(CH_2)_mNR_6C(O)R_8$, $(CH_2)_mC(O)R_8$, $(CH_2)_mOC(O)R_8$, $O(CH_2)_mNR_6R_7$, $OC(O)NR_6R_7$, $OC(O)(CH_2)_mCO_2R_6$ or $(CH_2)_n[N=X]$, $OC(O)[N=X]$, $(CH^2)_mOC(O)[N=X]$ (in which [N=X], in this invention, represents a heterocyclic group with 4 to 7 members with the nitrogen atom N, which is a member of the heterocyclic group, and X represents the remaining members, which are necessary to complete the heterocylic group, selected from the group constituted by O, S, $CH_2$, CH, N, $NR_9$ and $COR_{10}$), substituted or non substituted aryl or lower arylalkyl (i.e. substituted between once and four times on the aryl group or the heterocycle), in which the substituent is a lower alkyl, halo, nitro, amino, lower alkylamino, lower haloalkyl, lower hydroxyalkyl, lower alkoxy or lower alkoxy lower alkyl) or $R_2$ and $R_3$ form together a chain with 3 or 4 members in which the elements of the chain are selected from the group constituted by CH, $CH_2$, O, S, N or $NR_9$;

$R_5$ represents H, halo, lower haloalkyl, lower alkyl, lower alkoxy, lower alkoxy lower alkyl, lower alkylthio lower alkyl, cycloalkyl, cycloalkyl lower alkyl, cyano, cyanoalkyl, lower alkyl lower sulphonylalkyl, lower hydroxyalkyl, nitro, $(CH_2)_mC(O)R_8$, $(CH_2)_mNR_6C(O)R_8$, $(CH_2)_mNR_6R_7$, $(CH_2)_mN(CH_3)(CH_2)_nNR_6R_7$, $(CH_2)_mOC(O)R_8$, $(CH_2)_mOC(O)NR_6R_7$, $(CH_2)_mS(O)_qR_{11}$, $(CH_2)_mP(O)R_{12}R_{13}$, $(CH_2)_2P(S)R_{12}R_{13}$ or $(CH_2)_n[N=X]$, $OC(O)[N=X]$, $(CH_2)_mOC(O)[N=X]$, substituted or non substituted aryl or lower arylalkyl (i.e. substituted between once and four times on the aryl or heteroaryl group), in which the substituent is a lower alkyl, halo, nitro, amino, lower alkylamino, lower haloalkyl, lower hydroxyalkyl, lower alkoxy or lower alkoxy lower alkyl;

$R_6$ and $R_7$ represent, independently, H, a lower alkyl, lower hydroxyalkyl, lower alkyl lower aminoalkyl, lower aminoalkyl, cycloalkyl, cycloalkyl lower alkyl, lower alkenyl, lower alkoxy lower alkyl, lower haloalkyl, or substituted or non substituted aryl or lower arylalkyl (i.e. substituted between once and four times on the aryl group), in which the substituent is a lower alkyl, halo, nitro, amino, lower alkylamino, lower haloalkyl, lower hydroxyalkyl, lower alkoxy or lower alkoxy lower alkyl;

$R_8$ represents H, a lower alkyl, lower hydroxyalkyl, amino, lower alkylamino, lower alkyl lower aminoalkyl, lower aminoalkyl, cycloalkyl, cycloalkyl lower allyl, lower alkenyl, lower alkoxy, lower alkoxy lower alkyl, lower haloalkyl, or substituted or non substituted aryl or lower arylalkyl (i.e. substituted between once and four times on the aryl group), in which the substituent is a lower alkyl, halo, nitro, amino, lower alkylamino, lower haloalkyl, lower hydroxyalkyl, lower alkoxy or lower alkoxy lower alkyl;

$R_9$ represents H, a lower alkyl, lower haloalkyl, aryl, lower arylalkyl, or aryl or lower arylalkyl in which the aryl group is substituted by one or more groups chosen from the following radicals: lower alkyl, halo, nitro, amino, lower alkylamino, lower haloalkyl, lower hydroxyalkyl, lower alkoxy or lower alkoxy lower alkyl;

$R_{10}$ represents H, a lower alkyl, lower haloalkyl, lower alkoxy, aryl or aryl substituted (i.e. having one to four substituents on the aryl group) by one or more groups chosen from the following radicals: lower alkyl, lower haloalkyl, lower hydroxyalkyl or lower alkoxy lower alkyl;

$R_{11}$ represents a lower alkyl, aryl, $(CH_2)_m OR_{14}$, $(CH_2)_m SR_{14}$, $(CH_2)_2 NR_{14}R_{15}$ or $(CH_2)_m[N=X]$;

$R_{12}$ and $R_{13}$ represent, independently, a lower alkyl, aryl, lower alkoxy, aryloxy or amino;

$R_{14}$ and $R_{15}$ represent, independently, H, lower alkyl or aryl;

$R_{16}$ represents H or $OR_{21}$;

$R_{17}$ represents $OR_6$ or $NR_6R_7$;

$R_{18}$ and $R_{19}$ represent, independently, H, halo, lower alkyl, lower alkoxy or hydroxy;

$R_{20}$ represents H or halo;

$R_{21}$ represents H, a lower alkyl, CHO or $C(O)(CH_2)_m CH_3$;

m is an integer comprised between 0 and 6;

n is 1 or 2; and q represents an integer from 0 to 2; and

[N=X] represents a heterocyclic group with 4 to 7 members, X representing the chain necessary to complete said heterocyclic group and selected from the group constituted by O, S, $CH_2$, CH, N, $NR_9$ and $COR_{10}$;

or a pharmaceutically acceptable salt of the latter.

A particular subject of the invention is the compounds of formulae I and II as defined above in which $R_1$ represents a lower alkyl, lower alkenyl, lower haloalkyl, lower alkoxy lower alkyl or lower alkylthio lower alkyl; $R_5$ represents H, halo, lower haloalkyl, lower alkyl, lower alkoxy, lower alkoxy lower alkyl, lower alkylthio lower alkyl, cycloalkyl, cycloalkyl lower alkyl, cyano, cyanoalkyl, lower hydroxyalkyl, nitro, $(CH_2)_m C(O)R_8$, $(CH_2)_m NR_6C(O)R_8$, $(CH_2)_m NR_6R_7$, $(CH_2)_m N(CH_3)(CH_2)_n NR_6R_7$, $(CH_2)_m OC(O)R_8$, $(CH_2)_m OC(O)NR_6R_7$, or $(CH_2)_n[N=X]$, $OC(O)[N=X]$, $(CH_2)_m OC(O)[N=X]$, substituted or non substituted aryl or lower arylalkyl; $R_{12}$ and $R_{13}$ represent, independently, a lower alkyl; $R_{16}$ represents $OR_{21}$; and $R_{18}$, $R_{19}$ and $R_{20}$ represent H.

The invention has more particularly as its subject matter the compounds of formula (I) and (II) as is defined above in which $R_1$ represents a lower alkyl, lower alkenyl, lower haloalkyl or lower alkoxy lower alkyl; $R_2$, $R_3$ and $R_4$ represent, independently, H, halo, lower haloalkyl, lower alkyl, nitro, amido, lower amidoalkyl, hydrazino, lower hydrazinoalkyl, azido, lower azidoalkyl, $(CH_2)_m NR_6R_7$, $(CH_2)_m OR_6$, $(CH_2)_m SR_6$, $(CH_2)_m C(O)R_8$, $(CH_2)_n[N=X]$, or $(CH_2)_m OC(O)[N=X]$ substituted or non substituted, or $OC(O)[N=X]$; or $R_2$ and $R_3$ form together a chain with 3 or 4 members in which the elements of the chain are selected from the group constituted by CH, $CH_2$, O, S, N or $NR_9$; $R_5$ represents H, halo, lower haloalkyl, lower alkyl, lower alkoxy, lower alkoxy lower alkyl, lower alkylthio lower alkyl, lower hydroxyalkyl, nitro, $(CH_2)_m C(O)R_8$, $(CH_2)_m NR_6C(O)R_8$, $(CH_2)_m NR_6R_7$, $(CH_2)_m N(CH_3)(CH_2)_n NR_6R_7$, $(CH_2)_m OC(O)R_8$, $(CH_2)_m OC(O)NR_6R_7$, or $(CH_2)_n[N=X]$, $OC(O)[N=X]$ substituted or non substituted or $(CH_2)_m OC(O)[N=X]$; $R_6$ and $R_7$ represent, independently, H, a lower alkyl, lower hydroxyalkyl, lower alkyl lower aminoalkyl, lower aminoalkyl, cycloalkyl, cycloalkyl lower alkyl, lower alkoxy lower alkyl, lower haloalkyl, or substituted or non substituted aryl or lower arylalkyl; $R_8$ represents H, a lower alkyl, lower hydroxyalkyl, lower alkylamino, lower alkyl lower aminoalkyl, lower aminoalkyl, cycloalkyl, cycloalkyl lower alkyl, lower alkenyl, lower alkoxy, lower alkoxy lower alkyl, lower haloalkyl, or substituted or non substituted aryl or lower arylalkyl; $R_9$ represents H, a lower alkyl or lower haloalkyl; $R_{10}$ represents H, a lower alkyl, lower haloalkyl or lower alkoxy; $R_9$ represents H or lower alkyl; and $R_{14}$ and $R_{15}$ represent, independently, H or lower alkyl.

In a more preferred manner, $R_2$ represents H or halo and preferably H, chloro or fluoro; and $R_3$ represents H, a lower alkyl, halo or $OR_6$ in which $R_6$ represents H, a lower alkyl or a lower arylalkyl and preferably H, fluoro, chloro, methyl or methoxy. Also in a more preferred manner, $R_2$ and $R_3$ together form a methylenedioxy or an ethylenedioxy.

A more particular subject of the invention is the compounds of formula (I) and (II) for which $R_2$ represents a hydrogen or halogen atom, $R_3$ represents a halogen atom, a lower alkyl or a lower alkoxy, $R_4$ and $R_{16}$ represent hydrogen atoms, and $R_{18}$, $R_{19}$ and $R_{20}$ represent hydrogen atoms; or a pharmaceutically acceptable salt of the latter. An aminoalkyl radical will then preferably be chosen for $R_5$.

A more particular subject of the invention is the products described hereafter in the examples and corresponding to the following formulae:

5-ethyl-9,10-difluoro-4,5-dihydro-5-hydroxy-12-(1,2,5,6-tetrahydopyridinomethyl-1H-oxepino[3',4':6,7]indolizino[1,2-b]quinoline-3,15(4H,13H)-dione hydrochloride 5-ethyl-9,10-difluoro-4,5-dihydro-5-hydroxy-12-(4-methylpiperidinomethyl)-1H-oxepino[3',4':6,7]indolizino[1,2-b]quinoline-3,15(4H,13H)-dione 5-ethyl-9,10-difluoro-4,5-dihydro-5-hydroxy-12-pyrrolidinomethyl-1H-oxepino[3',4':6,7]indolizino[1,2-b]quinoline-3,15(4H,13H)-dione 5-ethyl-9,10-difluoro-4,5-dihydro-5-hydroxy-12-(4-methylpiperazinomethyl-1H-oxepino[3',4':6,7]indolizino[1,2-b]quinoline-3,15(4H,13H)-dione 5-ethyl-9,10-difluoro-4,5-dihydro-5-hydroxy-12-piperidinomethyl-1H-oxepino[3',4':6,7]indolizino[1,2-b]quinoline-3,15(4H,13H)-dione 5-ethyl-9,10-difluoro-4,5-dihydro-5-hydroxy-12-dimethylamino-methyl-1H-oxepino(3',4':6,7]indolizino[1,2-b]quinoline-3,15(4H,13H)-dione 9-chloro-5-ethyl-4,5-dihydro-5-hydroxy-10-methyl-12-morpholinomethyl-1H-oxepino[3',4':6,7]indolizino[1,2-b]quinoline-3,15(4H,13H)-dione 9-chloro-5-ethyl-4,5-dihydro-5-hydroxy-10-methyl-12-(4-methylpiperazinomethyl)-1H-oxepino[3',4':6,7]indolizino[1,2-b]quinoline-3,15(4H,13H)-dione 12-benzylpiperazinomethyl-9-chloro-5-ethyl-4,5-dihydro-5-hydroxy-10-methyl-1H-oxepino[3',4':6,7]indolizino[1,2-b]quinoline-3,15(4H,13H)-dione 12-(4-benzylpiperazinomethyl)-9-chloro-5-ethyl4,5-dihydro-5-hydroxy-10-methyl-1H-oxepino[3',4':6,7]indolizino[1,2-b]quinoline-3,15(4H,13H)-dione 9-chloro-5-ethyl4,5-dihydro-5-hydroxy-10-methyl-12-piperidinomethyl-1H-oxepino[3',4':6,7]indolizino[1,2-b]quinoline-3,15(4H$_{1,13}$H)-dione 12-(4-benzylpiperazinomethyl)-5-ethyl-9-fluoro-4,5-dihydro-5-hydroxy-1H-oxepino[3',4':6,7]indolizino[1,2-b]quinoline-3,15(4H,13H)-dione 12-(4-benzylpiperazinomethyl)-5-ethyl-9-fluoro-4,5-dihydro-5-hydroxy-10-methyl-1H-oxepino[3',4':6,7]indolizino[1,2-b]quinoline-3,15(4H,13H)-dione 5-ethyl-9-fluoro-4,5-dihydro-5-hydroxy-10-methyl-12-dimethylaminomethyl-1H-oxepino[3',4':6,7]indolizino[1,2-b]quinoline-3,15(4H,13H)-dione 5-ethyl-12-diethylaminomethyl-9-fluoro-4,5-dihydro-5-hydroxy-10-methyl-1H-oxepino[3',4':6,7]indolizino[1,2-b]quinoline-3,15(4H,13H)-dione 5-ethyl-9-fluoro-4,5-dihydro-5-hydroxy-10-methyl-12-(4-methyl piperidinomethyl)-1H-oxepino[3',4':6,7]indolizino[1,2-b]quinoline-3,15(4H,13H)-dione 5-ethyl-9-fluoro-4,5-dihydro-5-hydroxy-10-methyl-12-pyrrolidinomethyl-1H-oxepino[3',4':6,7]indolizino[1,2-b]quinoline-3,15(4H,13H)-dione 5-ethyl-9-fluoro-4,5-dihydro-5-hydroxy-10-methyl-12-(1,2,5,6-tetrahydropyridinomethyl)-1H-oxepino[3',4':6,7]indolizino[1,2-b]quinoline-3,15(4H,131)-dione 12-diisobutylaminomethyl-5-ethyl-9-fluoro-4,5-dihydro-5-hydroxy-10-methyl-1H-oxepino[3',4':6,7]indolizino[1,2-b]quinoline-3,15(4H,13H)-dione 5-ethyl-9-fluoro-4,5-dihydro-5-hydroxy-10-methoxy-12-(4-methylpiperazinomethyl)-1H-oxepino[3',4':6,7]indolizino[1,2-b]quinoline-3,15(4H,13H)-dione 5-ethyl-9-fluoro-4,5-dihydro-5-hydroxy-10-methoxy-12-piperidinomethyl-1H-oxepino[3',4':6,7]indolizino[1,2-b]quinoline-3,15(4H,13H)-dione 9-chloro-5-ethyl-4,5-dihydro-5-hydroxy-10-methoxy-12-dimethylaminomethyl-1H-oxepino[3',4':6,7]indolizino[1,2-b]quinoline-3,15(4H,13H)-dione 9-chloro-5-ethyl-4,5-dihydro-5-hydroxy-10-methoxy-12-piperidinomethyl-1H-oxepino[3',4':6,7]indolizino[1,2-b]quinoline-3,15(4H,13H)-dione hydrochloride 5-ethyl-4,5-dihydro-5-hydroxy-10-methoxy-12-(1,2,5,6-tetrahydropyridinomethyl)-1H-oxepino[3',4':6,7]indolizino[1,2-b]quinoline-3,15(4H$_{13}$H)-dione hydrochloride 5-ethyl-4,5-dihydro-5-hydroxy-10-methoxy-12-(4-methylpiperidinomethyl)-1H-oxepino[3',4':6,7]indolizino[1,2-b]quinoline-3,15(4H,13H)-dione 5-ethyl-4,5-dihydro-5-hydroxy-10-methoxy-12-(4-methylpiperazinomethyl)-1H-oxepino[3',4':6,7]indolizino[1,2-b]quinoline-3,15(4H,13H)-dione 5-ethyl-4,5-dihydro-5-hydroxy-10-methoxy-12-pyrrolidinomethyl-1H-oxepino[3',4':6,7]indolizino[1,2-b]quinoline-3,15(4H,13H)-dione 12-(4-benzylpiperazinomethyl)-5-ethyl4,5-dihydro-5-hydroxy-10-methoxy-1H-oxepino[3',4':6,7]indolizino[1,2-b]quinoline-3,15(4H,13H)-dione 9-chloro-5-ethyl-4,5-dihydro-5-hydroxy-10-methyl-12-(4-methylpiperidinomethyl)-1H-oxepino[3',4':6,7]indolizino[1,2-b]quinoline-3,15(4H,13H)-dione;

10-benzyloxy-5-ethyl-9-fluoro-4,5-dihydro-5-hydroxy-1H-oxepino[3',4':6,7]indolizino[1,2-b]quinoline-3,15(4H,13H)-dione;

5-ethyl-9-fluoro-4,5-dihydro-5,10-dihydroxy-1H-oxepino[3',4':6,7]indolizino[1,2-b]quinoline-3,15(4H,13H)-dione;

or a pharmaceutically acceptable salt of the latter.

A more particular subject of the invention is the compounds of formula (I) as defined above, in which $R_1$ represents the ethyl group; $R_2$ and $R_3$ represent, independently, H, a lower alkyl, halo, lower alkyl halo or $(CH_2)_mOR_6$, or $R_2$ and $R_3$ form together a methylenedioxy or an ethylenedioxy; $R_4$ and $R_5$ represent, independently, H, a lower alkyl, $(CH_2)_mNR_6R_7$, or $(CH_2)_n[N=X]$ non substituted or substituted by a lower alkyl; $R_{20}$ represents H and $R_{17}$ represents $OR_6$, in which $R_6$ represents H or a lower alkyl, or $NR_6R_7$ in which $R_6$ and $R_7$, independently, represent H, a lower alkyl, aryl or lower alkyl aryl. Preferably, $R_4$ represents H or $(CH_2)_mNR_6R_7$, in which $R_6$ and $R_7$ represent, independently, H or a lower alkyl; $R_5$ represents H, a lower alkyl or $(CH_2)_n[N=X]$ non substituted or substituted by a lower alkyl; and $R_{17}$ represents $OR_6$ in which $R_6$ represents H or a lower alkyl; or a pharmaceutically acceptable salt of the latter. As an example of substituted or non substituted [N=X], there can be mentioned the piperidyl, morpholinyl, piperazinyl, imidazolyl and 4-methylpiperazinyl radical.

In a more preferred manner, $R_2$ represents H or halo and preferably H, chloro or fluoro; $R_3$ represents H, a lower alkyl, halo or $OR_6$ in which $R_6$ represents H, a lower alkyl or a lower alkyl aryl and preferably H, fluoro, chloro, methyl or methoxy. Also in a more preferred manner $R_2$ and $R_3$ form together dioxymethylene or dioxyethylene.

A more particular subject of the invention is the products described hereafter in the examples, in particular the products corresponding to the following formulae:

5-ethyl-9,10-difluoro-4,5-dihydro-5-hydroxy-12-(4-methyl piperidinomethyl)-1H-oxepino[3',4':6,7]indolizino[1,2-b]quinoline-3,15(4H,13H)-dione;

5-ethyl-12-diethylaminomethyl-9-fluoro-4,5-dihydro-5-hydroxy-10-methyl-1H-oxepino[3',4':6,7]indolizino[1,2-b]quinoline-3,15(4H,13H)-dione;

5-ethyl-9-fluoro-4,5-dihydro-5-hydroxy-10-methyl-12-(4-methyl piperidinomethyl)-1H-oxepino[3',4':6,7]indolizino[1,2-b]quinoline-3,15(4H,13H)-dione;

5-ethyl-9-fluoro-4,5-dihydro-5-hydroxy-10-methyl-12-pyrrolidinomethyl-1H-oxepino[3',4':6,7]indolizino[1,2-b]quinoline-3,15(4H,13H)-dione;

9-chloro-5-ethyl-4,5-dihydro-5-hydroxy-10-methoxy-12-piperidinomethyl-1H-oxepino[3',4':6,7]indolizino[1,2-b]quinoline-3,15(4H,13H)-dione hydrochloride;

5-ethyl-4,5-dihydro-5-hydroxy-10-methoxy-12-(4-methylpiperidinomethyl)-1H-oxepino[3',4':6,7]indolizino[1,2-b]quinoline-3,15(4H,13H)-dione;

9-chloro-5-ethyl-4,5-dihydro-5-hydroxy-10-methyl-12-(4-methylpiperidinomethyl)-1H-oxepino[3',4':6,7]indolizino[1,2-b]quinoline-3,15(4H,13H)-dione;

or a pharmaceutically acceptable salt of the latter.

Camptothecin and certain of its analogues are not hydrosoluble, which makes their administration by parenteral route difficult. Hydrosoluble derivatives of camptothecin have been prepared where rings A and B carry salifiable substituents (cf. for example U.S. Pat. No. 4,981,968, U.S. Pat. No. 5,049,668, EP 540,099). However, these products revealed an antitumoral activity which was reduced with respect to that of non-hydrosoluble derivatives. Other hydrosoluble derivatives of camptothecin have also been prepared where the hydroxyl group in position 20 is esterified by an acid carrying a salifiable radical such as for example glycine (cf. U.S. Pat. No. 4,943,579 and PCT No. WO 96/02546). These derivatives are designated by a person skilled in the art under the name "prodrug forms" as they are not biologically active in themselves, but only after a first metabolization phase once administered to the patient. The prodrug forms of the α-hydroxylactone analogues of camptothecin have shown a good anti-tumoral effectiveness in animals and clinically, but accompanied by damaging side-effects such as the appearance of serious diarrhoeas which can put the patient's life in danger. It is therefore necessary to develop hydrosoluble analogues of camptothecin which are more effective and better tolerated.

Hydrosolubility of the camptothecin analogues being important, some compounds according to the present invention have also been designed in order to possess this property as well.

Two solutions were chosen in order to increase the hydrosolubility of the camptothecin analogues: the first consists in grafting an oxazine onto the A ring of the molecule, and the second in designing prodrug forms by acetylating the hydroxy function of the β-hydroxylactone.

More specifically, among this new class of camptothecin analogues, the compounds according to the present invention are either analogues modified by fixation of an oxazine ring on carbons 10 and 11 or prodrug forms in which a β-hydroxylactone replaces the natural α-hydroxylactone of camptothecin. The compounds of the present invention are therefore camptothecin analogue β-hydroxylactones on which an oxazine ring or hydrosoluble prodrugs have been grafted and present a powerful biological activity which is unexpected in the light of the state of the prior art.

Another object of the invention is therefore the compounds of formula $(I)_{OP}$ and formula $(II)_{OP}$:

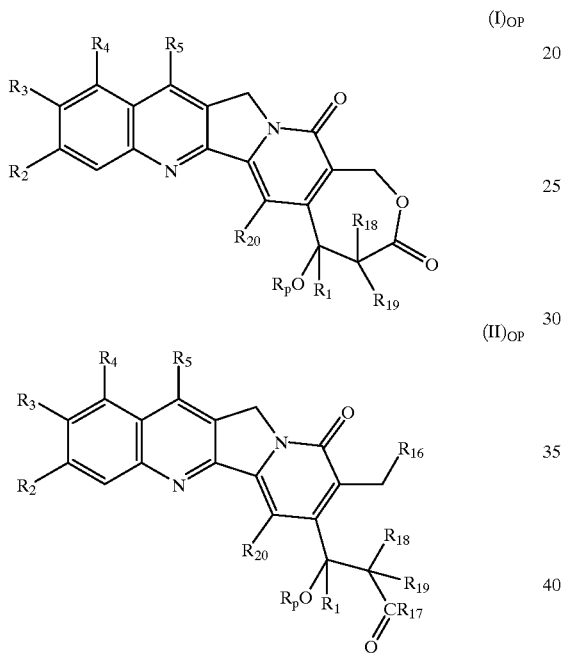

in racemic or enantiomeric form or any combinations of these forms, in which $R_1$ represents a lower alkyl, a lower alkenyl, a lower alkynyl, a lower haloalkyl, a lower alkoxy lower alkyl or lower alkylthio lower alkyl;

$R_2$, $R_3$ and $R_4$ represent, independently, H, halo, lower haloalkyl, lower alkyl, lower alkenyl, cyano, lower cyanoalkyl, nitro, lower nitroalkyl, amido, lower amidoalkyl, hydrazino, lower hydrazinoalkyl, azido, lower azidoalkyl, $(CH_2)_mNR_6R_7$, $(CH_2)_mOR_6$, $(CH_2)_mSR_6$, $(CH_2)_mCO_2R_6$, $(CH_2)_mNR_6C(O)R_8$, $(CH_2)_mC(O)R_8$, $(CH_2)_mOC(O)R_8$, $O(CH_2)_mNR_6R_7$, $OC(O)NR_6R_7$, $OC(O)(CH_2)_mCO_2R_6$ or $(CH_2)_n[N=X]$, $OC(O)[N=X]$, $(CH_2)_mOC(O)[N=X]$ (in which [N=X], in this invention, represents a heterocyclic group with 4 to 7 members with the nitrogen atom N, which is a member of the heterocyclic group, and X represents the remaining members, which are necessary to complete the heterocylic group, selected from the group constituted by O, S, $CH_2$, CH, N, $NR_9$ and $COR_{10}$), aryl or lower arylalkyl substituted (i.e. substituted between once and four times on the aryl group or the heterocycle) or non substituted, in which the substituent is a lower alkyl, halo, nitro, amino, lower alkylamino, lower haloalkyl, lower hydroxyalkyl, lower alkoxy or lower alkoxy lower alkyl or $R_2$ and $R_3$ or $R_3$ and $R_4$ form together a chain with 3 or 4 members in which the elements of the chain are selected from the group constituted by CH, $CH_2$, O, S, N or $NR_9$;

$R_5$ represents H, halo, lower haloalkyl, lower alkyl, lower alkoxy, lower alkoxy lower alkyl, lower alkylthio lower alkyl, cycloalkyl, cycloalkyl lower alkyl, cyano, cyanoalkyl, lower alkyl lower sulphonylalkyl, lower hydroxyalkyl, nitro, $(CH_2)_mC(O)R_8$, $(CH_2)_mNR_6C(O)R_8$, $(CH_2)_mNR_6R_7$, $(CH_2)_mN(CH_3)(CH_2)_nNR_6R_7$, $(CH_2)_mOC(O)R_8$, $(CH_2)_mOC(O)NR_6R_7$, $(CH_2)_mS(O)_qR_{11}$, $(CH_2)_mP(O)R_{12}R_{13}(CH_2)_2P(S)R_{12}R_{13}$ or $(CH_2)_n[N=X]$, $OC(O)[N=X]$, $(CH_2)_mOC(O)[N=X]$, substituted or non substituted aryl or lower alkyl aryl (i.e. substituted between once and four times on the aryl or heteroaryl group), in which the substituent is a lower alkyl, halo, nitro, amino, lower alkylamino, lower haloalkyl, lower hydroxyalkyl, lower alkoxy or lower alkoxy lower alkyl;

$R_6$ and $R_7$ represent, independently, H, a lower alkyl, lower hydroxyalkyl, lower alkyl lower aminoalkyl, lower aminoalkyl, cycloalkyl, cycloalkyl lower alkyl, lower alkenyl, lower alkoxy lower alkyl, lower haloalkyl, or a substituted or non substituted aryl or lower arylalkyl (i.e. substituted between once and four times on the aryl group), in which the substituent is a lower alkyl, halo, nitro, amino, lower alkylamino, lower haloalkyl, lower hydroxyalkyl, lower alkoxy or lower alkoxy lower alkyl;

$R_8$ represents H, a lower alkyl, lower hydroxyalkyl, amino, lower alkylamino, lower alkyl lower aminoalkyl, lower aminoalkyl, cycloalkyl, cycloalkyl lower alkyl, lower alkenyl, lower alkoxy, lower alkoxy lower alkyl, lower haloalkyl, or substituted or non substituted aryl or lower arylalkyl (i.e. substituted between once and four times on the aryl group), in which the substituent is a lower alkyl, halo, nitro, amino, lower alkylamino, lower haloalkyl, lower hydroxyalkyl, lower alkoxy or lower alkoxy lower alkyl;

$R_9$ represents H, a lower alkyl, lower haloalkyl, aryl, lower arylalkyl, or aryl or lower arylalkyl in which the aryl group is substituted by one or more groups chosen from the following radicals: lower alkyl, halo, nitro, amino, lower alkylamino, lower haloalkyl, lower hydroxyalkyl, lower alkoxy or lower alkoxy lower alkyl;

$R_{10}$ represents H, a lower alkyl, lower haloalkyl, lower alkoxy, aryl or aryl substituted (i.e. having one to four substituents on the aryl group) by one or more groups chosen from the following radicals: lower alkyl, lower haloalkyl, lower hydroxyalkyl or lower alkoxy lower alkyl;

$R_{11}$ represents a lower alkyl, aryl, $(CH_2)_mOR_{14}$, $(CH_2)_mSR_{14}$, $(CH_2)_2NR_{14}R_{15}$ or $(CH_2)_m[N=X]$;

$R_{12}$ and $R_{13}$ represent, independently, a lower alkyl, aryl, lower alkoxy, aryloxy or amino;

$R_{14}$ and $R_{15}$ represent, independently, H, lower alkyl or aryl;

$R_{16}$ represents H or $OR_{21}$;

$R_{17}$ represents $OR_6$ or $NR_6R_7$;

$R_{18}$ and $R_{19}$ represent, independently, H, halo, lower alkyl, lower alkoxy or hydroxy;

$R_{20}$ represents H or halo;

$R_{21}$ represents H, a lower alkyl, CHO or $C(O)CH_2)_mCH_3$;

$R_p$ represents H or an easily cleavable group preferably chosen from the groups corresponding to the formula —C(O)—A—$NR_{22}R_{23}$, in which A represents a linear or branched alkylene radical optionally substituted by a radical chosen from the free, esterified or salified hydroxy, halogen, free, esterified or salified carboxy, amino, mono or dialkylamino radicals, while $R_{22}$ and $R_{23}$, independently, represent H, a lower alkyl, lower hydroxyalkyl, lower alkyl lower aminoalkyl, lower aminoalkyl, cycloalkyl, cycloalkyl lower alkyl, lower alkenyl, lower alkoxy lower alkyl, lower haloalkyl, or substituted or non substituted aryl or lower arylalkyl (i.e., substituted one to four times on the aryl group), in which the substituent is a lower alkyl, halo, nitro, amino, lower alkylamino, lower haloalkyl, lower hydroxyalkyl, lower alkoxy or lower alkoxy lower alkyl;

m is an integer comprised between 0 and 6;

n is 1 or 2; and q represents an integer from 0 to 2; and

[N=X] represents a heterocyclic group with 4 to 7 members, X representing the chain necessary to complete said heterocyclic group and selected from the group constituted by O, S, $CH_2$, CH, N, $NR_9$ and $COR_{10}$;

it being understood that when Rp is a hydrogen atom, $R_3$ and $R_4$ together form a chain with 3 or 4 members;

or a pharmaceutically acceptable salt of the latter.

As concerns the oxazin-grafted forms of the invention, $R_2$ preferably represents a radical chosen from the group consisting of H, halo or lower alkyl.

As concerns the prodrug forms of the invention (those for which $R_p$ is not a hydrogen atom), the products of general formula $(I)_{OP}$ are preferred. Preferably, $R_2$ and $R_3$ then represent, independently, a radical chosen from the group consisting of halo or lower alkyl.

Examples of substituted camptothecins used as starting products can be found in the U.S. Pat. Nos. 4,473,692, 4,604,463, 4,894,956, 5,162,532, 5,395,939, 5,315,007, 5,264,579, 5,258,516, 5,254,690, 5,212,317 and 5,341,745, the PCT Patent Applications Nos. US91/08028, US94/06451, US90/05172, US92/04611, US93/10987, US91/09598, EP94/03058 and EP95/00393 and the European Patent Application Nos. 325 247, 495 432, 321 122 and 540 099.

For the compounds comprising an oxazine ring:

a β-hydroxylactonic compound of general formula D

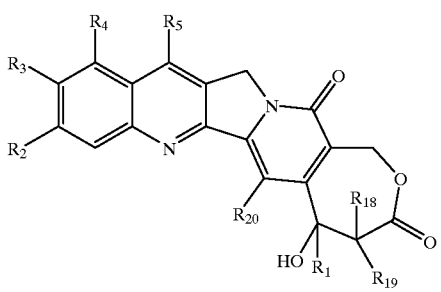

D in which $R_3$ is a hydroxyl radical, $R_4$ is H and $R_1$, $R_2$, $R_5$, $R_{18}$, $R_{19}$ and $R_{20}$ have the meaning indicated above is treated with a primary amine, under Mannich's conditions, in order to obtain a β-hydroxylactonic compound of general formula Ia

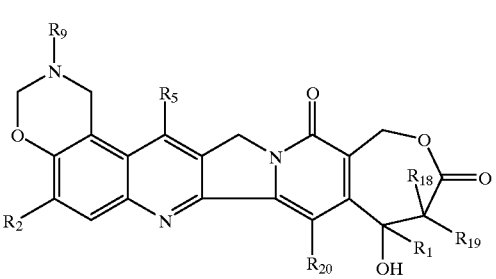

Ia in which $R_1$, $R_2$, $R_5$, $R_9$, $R_{18}$, $R_{19}$ and $R_{20}$ have the meaning indicated above.

This process consists in heating the starting product in the presence of a primary amine such as benzylamine, of formaldehyde in an acid solvent such as acetic acid or propionic acid at a temperature of 30° C. to 80° C. for a period of 0.5 to 5 hours. Alternatively, a suspension of starting product in acetic acid with a tri-N-substituted hexahydrotriazine such as hexahydro-1,3,5-trimethyl triazine, 1,3,5-triethylhexahydro triazine or 1,3,5-tribenzyl hexahydrotriazine can be heated at a temperature of 30° C. to 80° C. for a period of 0.5 to 5 hours.

the lactone of general formula Ia is opened optionally in a basic medium in order to produce after neutralization the compound of formula IIa

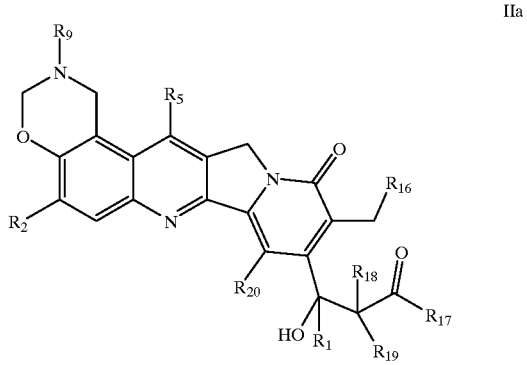

IIa in which $R_1$, $R_2$, $R_5$, $R_9$, $R_{17}$, $R_{18}$, $R_{19}$ and $R_{20}$ have the meaning indicated above; $R_{16}$ represents $OR_{21}$ in which $R_{21}$ represents H or a lower alkyl; and $R_{17}$ represents $OR_6$ or $NHR_6$ and $R_6$ represents H, a lower alkyl, cycloalkyl, lower cycloalkyl alkyl, lower alkenyl, lower alkoxy lower alkyl, or aryl or lower aryl alkyl.

the said compound of general formula D or Ia is optionally acylated, preferably with a derivative of the C(O)—A—N—$R_{22}R_{23}$ radical as defined above in order to produce the β-hydroxylactonic compound of general formula Ib, i.e. $(I)_{OP}$ with $R_p$ different from H (prodrug form of the invention).

in the same manner as with the lactone Ia, the lactone Ib can be opened in order to produce hydroxyacid IIb.

The opening of the lactone ring in a basic medium can more generally be used in order to convert products of general formula (B1) in products of general formula (B2).

In the above process, the $R_2$, $R_3$, $R_4$ and $R_5$ groups can be protected if necessary according to standard protection methods (Greene, T., Protective Groups in Organic Synthesis 10–86 (John Wiley & Sons 1981)). If at least one of the $R_{22}$ or $R_{23}$ groups is H, or contains at least one function which is chemically incompatible with the acylation process such as, for example, a primary or secondary amine, it is then necessary to use a protective group which is resistent to acylation conditions. A protective group commonly used for the amines is tert-butyloxycarbonyl (BOC). The acylation reaction is then carried out as described above, then the protective group is cleaved, for example by treatment with trifluoroacetic acid in the case of BOC, in order to produce the compound of general formula (I) or (II). Use of protective groups is known to a person skilled in the art (for other examples, reference can be made to Greene, T., Protective Groups in Organic Synthesis, John Wiley & Sons, 1981).

The preparation of the compounds of general formula D is described later in the present application.

As it is used here, the term lower with reference to the alkyl, alkylthio and alkoxy groups designates linear or branched saturated aliphatic hydrocarbon groups containing 1 to 6 carbons, such as for example, methyl, ethyl, propyl, isopropyl, butyl, t-butyl, methylthio, ethylthio, methoxy and ethoxy. With reference to the alkenyl or alkynyl groups, the term lower designates groups containing 2 to 6 carbon atoms and one or more double or triple bonds, such as for example, the vinyl, allyl, isopropenyl, pentenyl, hexanyl, ethynyl propenyl, propynyl and butynyl groups. The term cycloalkyl designates a ring with 3 to 7 carbons, such as for example, the cyclopropyl, cyclobutyl, cyclopentyl or cyclohexyl groups. The term aryl designates a mono- di- or tricyclic hydrocarbon compound with at least one aromatic ring, each ring containing a maximum of 7 members, such as for example, phenyl, naphthyl, anthracyl, biphenyl or indenyl. The term halo signifies chloro, bromo, iodo or fluoro. The radicals corresponding to the expressions lower haloalkyl, lower cyanoalkyl, lower nitroalkyl, lower amidoalkyl, lower hydrazinoalkyl, lower azidoalkyl, lower arylalkyl, lower hydroxyalkyl, lower alkoxy lower alkyl, lower alkylthio lower alkyl, and lower alkyl lower sulphonylalkyl are substituted, respectively, by one to three halo, cyano, nitro, amido, hydrazino, azido, aryl, hydroxy, lower alkoxy, lower alkylthio or lower sulphonylalkyl groups. The lower alkylamino radical can contain one or two lower alkyl groups and represent, for example, $NHCH_3$, $NHCH_2CH_3$, $N(CH_3)_2$ or $N(CH_3)(CH_2CH_3)$. Examples of [N=X] include the piperidinyl, morpholinyl, piperizinyl and imidazolyl groups.

As has been observed for camptothecin, the carbon atom carrying the hydroxy function in the β-hydroxylactone or the β-hydroxycarboxylate group of the compounds according to the present invention, is asymmetrical. Consequently, the compounds according to the present invention have two possible enantiomeric forms, i.e. under "R" and "S" configurations. The present invention includes the two enantiomeric forms and any combinations of these forms, including "RS" racemic mixtures. In an effort to simplify matters, when no specific configuration is indicated in the structural formulae, it should be understood that the two enantiomeric forms and their mixtures are represented.

A subject of the invention is also preparation processes for the compounds of general formulae (B1) and (B2), either starting with camptothecin or substituted camptothecins, or by total chemical synthesis.

Therefore the invention relates to a preparation process for the compounds of formulae (B1) and (B2) according to the invention, and in particular the products the formulae of which are indicated above, starting with camptothecin or substituted camptothecins characterized in that:

camptothecin α-hydroxylactone of general formula

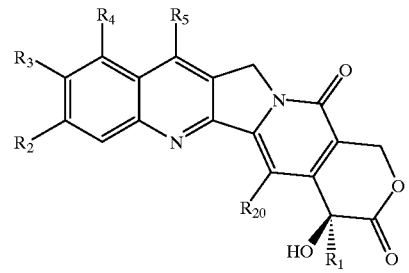

in which $R_1$, $R_2$, $R_3$, $R_4$, $R_5$ and $R_{20}$ have the meaning indicated above, is reduced in order to obtain the α-hydroxylactol of general formula A

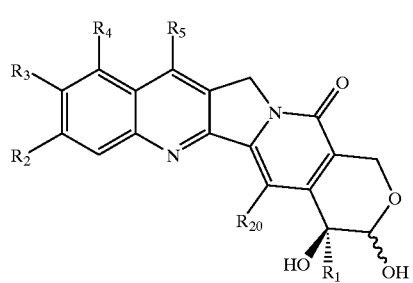

A in which $R_1$, $R_2$, $R_3$, $R_4$, $R_5$ and $R_{20}$ have the meaning indicated above, in compound A thus formed, the carbon-carbon bond linking the adjacent carbinols, is cut by treatment with an appropriate oxidizing agent so as to produce a compound of formula B

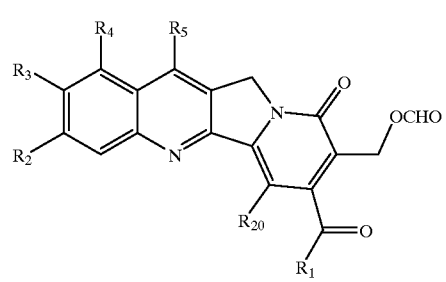

B in which $R_1$, $R_2$, $R_3$, $R_4$, $R_5$ and $R_{20}$ have the meaning indicated above, then treatment is carried out with a functionalized alkylating agent and the formyl a function of the compound of formula B is cut in order to produce a β-hydroxyester of general formula C

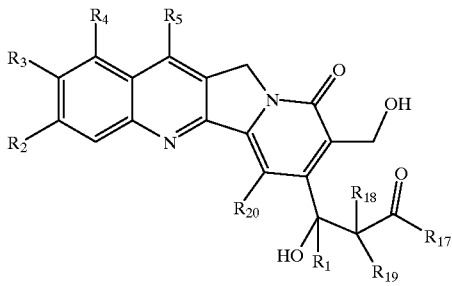

C in which $R_1$, $R_2$, $R_3$, $R_4$, $R_5$, $R_{18}$, $R_{19}$ and $R_{20}$ have the meaning indicated above, and $R_{17}$ represents $OR_6$ and $R_6$ represents a lower alkyl, cycloalkyl, cycloalkyl lower alkyl, lower alkenyl, lower alkoxy lower alkyl or aryl or lower aryl alkyl;

said compound of general formula C is cyclized in order to produce the β-hydroxylactonic compound of general formula D

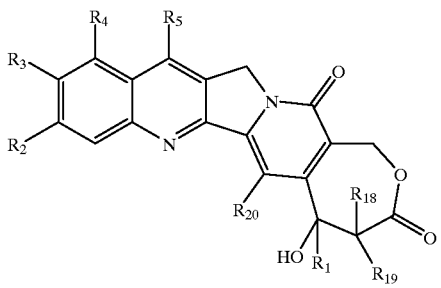

D in which $R_1$, $R_2$, $R_3$, $R_4$, $R_5$, $R_{18}$, $R_{19}$ and $R_{20}$ have the meaning indicated above, the lactone of general formula D is opened in order to produce the compound of formula E

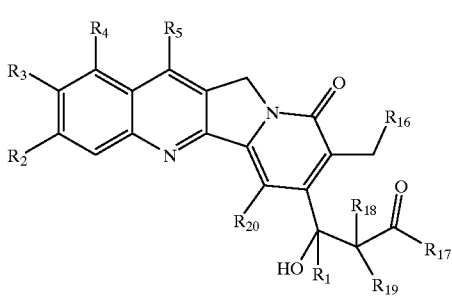

E in which $R_1$, $R_2$, $R_3$, $R_4$, $R_5$, $R_{17}$, $R_{18}$, $R_{19}$ and $R_{20}$ have the meaning indicated above; $R_{16}$ represents $OR_{21}$ in which $R_{21}$ represents H or a lower alkyl; and $R_{17}$ represents $OR_6$ or $NHR_6$ and $R_6$ represents H, a lower alkyl, cycloalkyl, cycloalkyl lower alkyl, lower alkenyl, lower alkoxy lower alkyl or aryl or lower aryl alkyl.

Certain compounds of general formula E can also be obtained by hydrolysis of the ester function of the corresponding compounds of general formula D. The compounds of general formula E in which $R_{16}$ and/or $R_{17}$ represent, independently, the hydroxy radical, can be esterified or amidified under standard conditions known to a person skilled in the art in order to obtain the corresponding esters or amides of general formula E.

In the above process, the $R_2$, $R_3$, $R_4$ and $R_5$ groups can be protected if necessary according to standard protection methods (Greene, T., Protective Groups in Organic Synthesis 10–86 (John Wiley & Sons 1981)). During this process, the reduction is carried out using a reducing agent in an appropriate solvent, such as, for example, sodium borohydride in methanol. The stage corresponding to the formation of compound of general formula B starting from compound of general formula A is implemented under oxidizing conditions, such as, for example, with lead tetraacetate, periodic acid or sodium metaperiodate in an appropriate solvent, such as, for example, acetic acid. The treatment with a functionalized alkylating agent can be implemented using a metallic derivative for example, of lithium or zinc, of a carboxylic ester in an anhydrous aprotic solvent such as, for example, tetrahydrofuran. The lactonization stage which allows compound of general formula D to be obtained starting from compound of general formula C is generally carried out under acid conditions, such as, for example, by treatment with trifluoroacetic acid or hydrochloric gas dissolved in an anhydrous solvent such as dichloromethane or dioxan. The opening of the lactonic ring of compound of general formula D in order to obtain compound of general formula E, can be carried out, for example, by hydrolysis under alkaline conditions followed by neutralization.

Examples of substituted camptothecins used as starting products can be found in the U.S. Pat. Nos. 4,473,692, 4,604,463, 4,894,956, 5,162,532, 5,395,939, 5,315,007, 5,264,579, 5,258,516, 5,254,690, 5,212,317 and 5,341,745, the PCT Patent Applications Nos. US91/08028, US94/06451, US90/05172, US92/04611, US93/10987, US91/09598, EP94/03058 and EP95/00393 and the European Patent Application Nos. 325 247, 495 432, 321 122 and 540 099.

Therefore, the invention also relates to a preparation process for the compounds of formulae (B1) and (B2), characterized in that a compound of general formula M

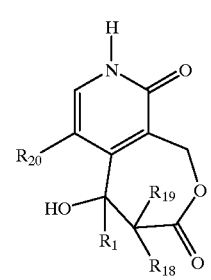

M in which $R_1$, $R_{18}$ and $R_{19}$ have the meaning indicated above and $R_{20}$ represents a hydrogen or a halogen atom, is coupled with a 2-halo-3-quinoline-methanol of general formula N

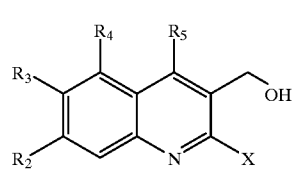

N in which $R_2$, $R_3$, $R_4$ and $R_5$ have the meaning indicated above and X represents a halogen atom, in order to produce the compound of formula O

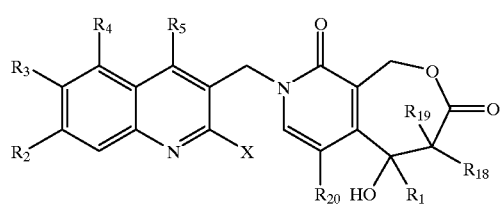

in which $R_1$, $R_2$, $R_3$, $R_4$, $R_5$, $R_{18}$, $R_{19}$, $R_{20}$ and X have the meaning indicated above;

then the compound of general formula O is cyclized in order to obtain the compound of general formula D as defined above.

In the above process, the $R_1$, $R_2$, $R_3$ and $R_4$ groups can be protected if necessary according to standard protection methods (Greene. T., Protective Groups in Organic Synthesis 10–86 (John Wiley & Sons 1981)). The formation of compound O starting from the compounds of general formulae M and N is carried out with a treatment known to a person skilled in the art under the name Mitsunobu's reaction (refer to Mitsunobu, O. et al. *Synthesis*, p.1 (1981)). The hydroxyl function of compound N is displaced by a nucleophile such as compound M or a deprotonated derivative of the latter, by a treatment with a phosphine, for example triphenylphosphine, and an azodicarboxylate derivative, for example diethyl azodicarboxylate, in an aprotic solvent such as, for example, tetrahydrofuran or N,N-dimethylformamide. The cyclization of compound O is preferably carried out in the presence of a palladium catalyst (for example palladium diacetate) under basic conditions (provided for example by an alkaline acetate optionally combined with a phase transfer agent, such as, for example, tetrabutylammonium bromide), in an aprotic solvent such as acetonitrile or N,N-dimethylformamide, at a temperature comprised between 50° C. and 120° C. (R. Grigg et al., *Tetrahedron* 46, page 4003 (1990)).

The compounds of general formula M are new. They can be prepared according to a process characterized in that the carbonyl of a pyridine of general formula

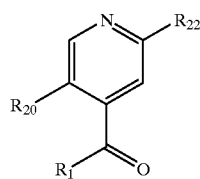

in which $R_1$ and $R_{20}$ have the meaning indicated above and $R_{22}$ represents a halogen atom or a lower alkoxy, is protected with an acetal function, in order to produce the compound of general formula F

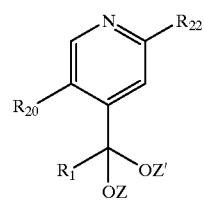

in which $R_1$, $R_{20}$ and $R_{22}$ have the meaning indicated above and the Z and Z' groups represent, independently, a lower alkyl or form together a saturated hydrocarbon chain with 2 to 4 carbons:

a hydroxymethyl function is introduced into the compound of general formula F in order to obtain a compound of general formula G

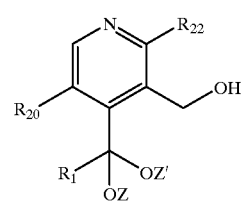

in which $R_1$, $R_{20}$, $R_{22}$, Z and Z' have the meaning indicated above, then the alcohol function of the compound of general formula G is protected in order to produce a compound of general formula H

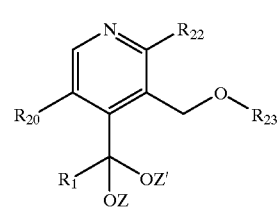

in which $R_1$, $R_{20}$, $R_{22}$, Z and Z' have the meaning indicated above and $R_{23}$ represents a protective group of the alcohol function.

the acetal of the compound of general formula H is deprotected in order to produce the compound of general formula I'

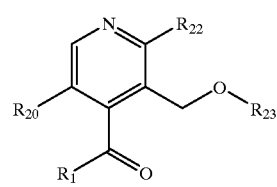

in which $R_1$, $R_{20}$, $R_{22}$ and $R_{23}$ have the meaning indicated above, the compound of formula I' is treated with a functionalized alkylating agent in order to produce a β-hydroxyester of general formula J

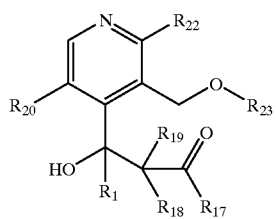

in which $R_1$, $R_{20}$, $R_{22}$ and $R_{23}$ have the meaning indicated above, and $R_{17}$, $R_{18}$ and $R_{19}$ are as defined in general formula II the protective group $R_{23}$ of the compound of general formula J is cleaved in order to produce a compound of general formula K,

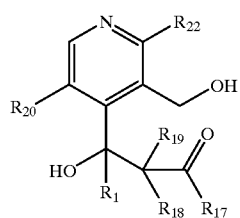

in which $R_1$, $R_{18}$, $R_{19}$, $R_{20}$ and $R_{22}$ have the meaning indicated above, and $R_{17}$ represents $OR_6$ or $NHR_6$ and $R_6$ represents H, a lower alkyl, cycloalkyl, lower alkyl cycloalkyl, lower alkenyl, lower alkyl lower alkoxy or aryl or lower alkyl aryl, the compound of general formula K is cyclized into the compound of general formula L

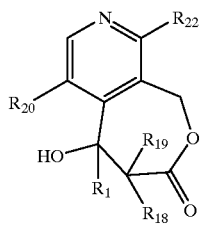

in which $R_1$, $R_{18}$, $R_{19}$, $R_{20}$ and $R_{22}$ have the meaning indicated above, and finally the $R_{22}$ radical of compound L is converted into carbonyl in order to obtain the compound of general formula M

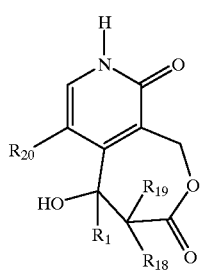

in which $R_1$, $R_{18}$, $R_{19}$, $R_{20}$, and $R_{22}$ have the meaning indicated above.

The carbonyl function of a 4-acyl-2-pyridine (obtained for example according to Lammattina J. L. *J. Heterocyclic Chem.* 20, p. 553 (1983)) is preferably protected by an acetal function, preferably a cyclic acetal, according to the standard conditions known to a person skilled in the art (Greene. T., Protective Groups in Organic Synthesis 10–86 (John Wiley & Sons 1981)). The intermediate thus obtained is treated with a sodium or potassium alcoholate in an aprotic solvent (for example acetonitrile), or the alcohol from which the alcoholate is derived, at a temperature comprised between 0° C. and 100° C. in order to produce the compound of general formula F. The latter can be lithiated in position 3 by treatment with an aryl- or alkyl-lithium (for example mesityl-lithium) in an ethereal solvent such as tetrahydrofuran at a temperature comprised between –100° C. and 0° C. A formulating electrophile such as N,N-dimethylformamide is added to the lithiated intermediate thus obtained, and the aldehyde thus obtained is treated, after hydrolysis, with a reducing agent such as sodium borohydride in order to produce the compound of general formula G. The protection of the alcohol function of compound of general formula G is carried out according to the standard conditions known to a person skilled in the art, in order to obtain a compound of general formula H. Examples of protective groups of the alcohol function include those which form ethers (i.e. methyl, methoxymethyl, tetrahydropyranyl, 2-methoxyethoxy methyl, benzyloxymethyl, t-butyl and benzyl (substituted or non substituted)), and esters (i.e. formate, acetate and isobutyrate). For other examples of protective groups of primary hydroxyls refer to Greene. T., Protective Groups in Organic Synthesis 10–86 (John Wiley & Sons 1981). The deprotection of the compound of general formula H in order to produce the compound of general formula I' is carried out under selective conditions maintaining the integrity of the $R_{23}$ radical, for example, by treatment under acid conditions (for example by trifluoroacetic acid). The selective conditions for the protection and deprotection of functional groups are known to a person skilled in the art (Greene. T., Protective Groups in Organic Synthesis 10–86 (John Wiley & Sons 1981)). The treatment of compound of general formula I' with a functionalized alkylating agent in order to produce a β-hydroxy ester of general formula J can be carried out using a lithium enolate or a zinc derivative of a carboxylic ester in an anhydrous aprotic solvent, for example, tetrahydrofuran. The protective group $R_{23}$ of the compound of general formula J is cleaved in order to produce a compound of general formula K under deprotection conditions known to a person skilled in the art. For example, when $R_{23}$ is a benzyl group, an alcoholic solution of the compound of general formula J with a palladium catalyst added to it can be subjected to a hydrogen atmosphere under a pressure of 0.5 to 10 Bar. The cyclization of the compound of general formula K thus obtained can be carried out under acid conditions (for example by treatment with trifluoroacetic acid, or hydrochloric gas dissolved in an anhydrous solvent such as dichloromethane or dioxan) in order to produce a β-hydroxylactonic ring with seven members such as in the compound of general formula L. The compounds of general formula L can be converted into pyridones of general formula M, for example, by treatment with warm hydrochloric acid, or by treatment with trimethylsilyl iodide.

The 2-halo-3-quinoline methanols of general formula N can be obtained starting from the acetanilides of general formula P

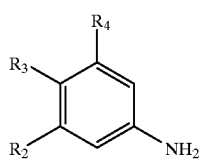

P in which $R_2$, $R_3$ and $R_4$ have the meaning indicated in the general formulae of compounds I and II. In the processes below, the $R_2$, $R_3$ and $R_4$ groups can be protected if necessary according to standard protection methods (Greene. T., Protective Groups in Organic Synthesis 10–86 (John Wiley & Sons 1981)).

The compounds of formula N can therefore be obtained according to the following process: the said anilines of formula P are N-acetylated by treatment with an acetylating agent such as, for example, acetic anhydride. The acetanilides thus obtained are treated at a temperature comprised between 50° C. and 100° C., preferably approximately 75° C., with a reagent known to a person skilled in the art under the name Vilsmeyer's reagent (obtained by the action of phosphoryl oxychloride on NN-dimethylformamide at a temperature comprised between 0° C. and 10° C.) in order to produce the corresponding 2-chloro-3-quinolinecarbaldehyde (for example, refer to Meth-Cohn et al. *J. Chem. Soc., Perkin Trans. I* p.1520 (1981); Meth-Cohn et al. *J. Chem. Soc., Perkin Trans. I* p.2509 (1981); and Nakasimhan et al. *J. Am. Chem. Soc.*, 112 p.4431 (1990)). The chlorine in position 2 of the 2-chloro-3-quinolinecarbaldehydes can be substituted by iodine or bromine by heating the product in an inert solvent such as acetonitrile in the presence of an iodine or bromine salt (for example sodium iodide or tetrabutylammonium bromide). A trace of acid such as concentrated hydrochloric acid may be necessary to catalyze this conversion. The 2-halo-3-quinolinecarbaldehydes are easily reduced to the corresponding 2-halo-3-quinolinemethanols of general formula N, under standard conditions known to a person skilled in the art such as treatment in an alcoholic solvent (for example methanol) with sodium borohydride at a temperature comprised between 0° C. and 40° C.

The compounds of formula N can also be obtained according to the following process: the anilines of general formula P as defined above are acylated by reaction with a nitrile (such as chloroacetonitrile or propionitrile) in the presence of boron trichloride and another Lewis acid such as aluminium trichloride, titanium tetrachloride or diethylaluminium chloride in an aprotic solvent or a mixture of aprotic solvents, followed by hydrolysis (cf. Sugasawa T. et al. *J. Am. Chem. Soc.* 100 p.4842 (1978)). The intermediate thus obtained is then treated with ethylmalonyl chloride in an aprotic solvent such as acetonitrile in the presence of a base such as triethylamine, then treated with an alkaline alcohol, for example, sodium methylate in methanol, in order to produce an ethyl 2-hydroxy-3-quinolinecarboxylate substituted in position 4. This is converted into ethyl 2-chloro-3-quinolinecarboxylate by treatment with phosphoryl oxychloride. When position 4 of the quinoline carries a chloromethyl group, a nucleophile substitution can be carried out by treatment with a secondary amine such as, for example, dimethylamine, N-methylpiperazine, morpholine or piperidine. The ethyl 2-chloro3-quinolinecarboxylate is then reduced with diisobutylalumihium hydride in an aprotic solvent such as dichloromethane in order to produce the 2-chloro-3-quinolinemethanol of general formula N. Analogues of intermediate compounds of general formula N have been described in the literature and in particular in the PCT Application 95/05427.

The invention also offers, as a new industrial product, a compound of general formula $M_X$ represented below:

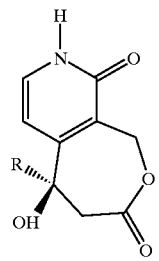

$M_X$ wherein R is a lower alkyl group, and preferably ethyl.

This product can be used for the manufacture of medicaments.

The compound of formula $M_X$ is synthesized according to a new process which is part of the invention and includes the following successive stages:

the racemic t-butyl ester represented below

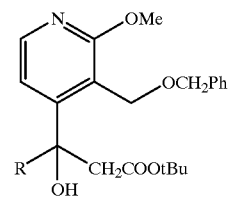

(for its preparation, refer in particular to the Patent Application WO 97/00876) is treated with trifluoroacetic acid for 18 hours at ambient temperate in order to produce the corresponding carboxylic acid;

then the quinidine salt of the acid obtained previously is heated in isopropyl alcohol at a temperature greater than 30° C., and preferably at about 50° C., before leaving the reaction medium to cool down to ambient temperatue, so that the salt of one of the enantiomers of the above-mentioned acid crystallized while the salt of the other enantiomer, the anion of which is represented below, remains in solution

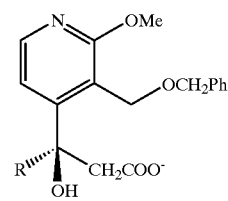

the solution in isopropyl alcohol of the salt of the enantiomer which has not crystallized is concentrated and treated with hydrochloric acid and agitated, producing the compound of general formula Ax represented below

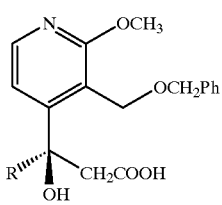

$A_X$ the compound of general formula $A_X$ is then put in contact with palladium on damp carbon, then ammonium formate is added to the mixture in order to produce the debenzylated product of general formula $B_X$ represented below

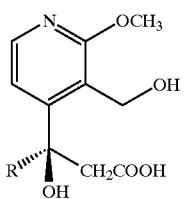

$B_X$ then the compound of general formula $B_X$ is cyclized by the action of dicyclohexylcarbodiimide in order to obtain the lactonic compound of general formula $C_X$ represented below

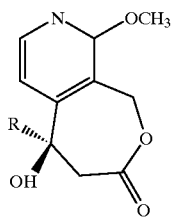

$C_X$ finally, the —OCH$_3$ group of the lactonic compound of general formula $C_X$ is converted into carbonyl, by the action of sodium iodide and trimethylsilyl chloride, in order to obtain a compound of general formula $M_X$ represented below.

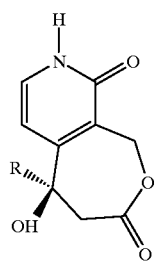

$M_X$

For the process described above, the reaction leading from the compound of general formula $A_X$ to the compound of general formula $B_X$ will preferably take place in methanol, and preferably by heating the reaction medium to about 40° C. after the addition of the ammonium formate. The cyclization of the compound of general formula $B_X$ in order to produce the compound $C_X$ can be carried out in THF, preferably at a temperature of about 50° C., while the reaction will preferably be carried out at ambient temperatue with acetonitrile as solvent in the reaction leading from the compound of general formula $C_X$ to the compound of general formula $M_X$.

In the particular case where R represents an ethyl group, the compound of formula $M_X$ is synthesized according to the process constituted by the following successive stages:

the racemic t-butyl ester represented below

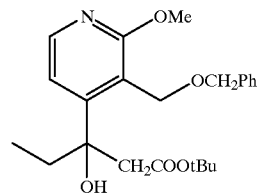

(for its preparation, refer in particular to the Patent Application WO 97/00876) is treated with trifluoroacetic acid for 18 hours at ambient temperatue in order to produce the corresponding carboxylic acid;

the quinidine salt of 3-(3-benzyloxymethyl-2-methoxy-4-pyridyl)-3-hydroxy-pentanoic acid is heated in isopropyl alcohol at a temperature higher than 30° C., and preferably at about 50° C., before leaving the reaction medium to cool down to ambient temperatue, so that the salt of the (+) enantiomer of 3-(3-benzyloxymethyl-2-methoxy-4-pyridyl)-3-hydroxy-pentanoic acid crystallizes whilst the salt of the (−) isomer the anion of which is represented below, remains in solution

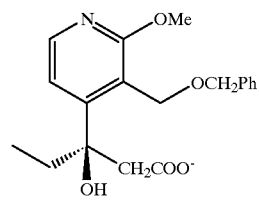

the solution in isopropyl alcohol of the salt of the (−) enantiomer of 3-(3-benzyloxymethyl-2-methoxy-4-pyridyl)-3-hydroxy-pentanoic acid is concentrated and treated with hydrochloric acid and agitated, producing the compound of formula $A_{X'}$ represented below

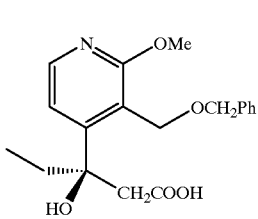

$A_{X'}$ the compound $A_{X'}$ is then put in contact with palladium on damp carbon, the ammonium formate is added to the mixture in order to produce the debenzylated product $B_{X'}$ represented below

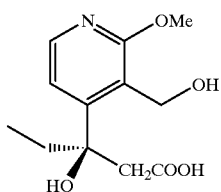

$B_{X'}$ then the compound of formula $B_{X'}$ is cyclized by the action of dicyclohexylcarbodiimide in order to obtain the lactonic compound of formula $C_{X'}$ represented below

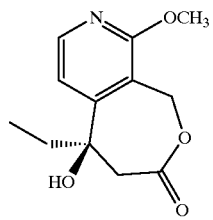

$C_{X'}$ finally, the —OCH$_3$ group of the lactonic compound of formula $C_{X'}$ is converted into carbonyl, by the action of sodium iodide and trimethylsilyl chloride, in order to obtain (+)-5-ethyl-5-hydroxy-1,3,4,5,8,9-hexahydrooxepino[3,4-c]pyridin-3,9-dione (or (+)-EHHOPD) represented below.

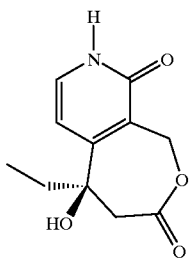

(+)-EHHOPD

A subject of the invention is also, as new industrial products and in particular as new industrial products intended for the preparation of the products of general formula (B1) and (B2); the products of general formulae I', M and $M_{X'}$ as described above.

Certain compounds of the invention can be prepared in the form of pharmaceutically acceptable salts according to the usual methods. Acceptable salts include, by way of example and in a non-limitative fashion, the addition salts with inorganic acids such as hydrochloride, sulphate, phosphate, diphosphate, hydrobromide, and nitrate or with organic acids such as acetate, maleate, fumarate, tartrate, succinate, citrate, lactate, methane sulphonate, p-toluenesulphonate, pamoate, salicylate, oxalate and stearate. The salts formed from bases such as sodium or potassium hydroxide also form part of the field of application of the present invention, when they are useable. For other examples of pharmaceutically acceptable salts one can refer to "Pharmaceutical Salts", J. Pharm. Sci. 66:1 (1977).

The compounds of the present invention possess useful pharmacological properties. Thus the compounds of the present invention have an inhibitory effect on topoisomerase I and/or II and an anti-tumoral activity. The state of the art suggests that the compounds according to the invention have an anti-parasitic and/or anti-viral activity. The compounds according to the present invention can also be used in different therapeutic applications.

An illustration of the pharmacological properties of the compounds according to the invention will be found hereafter in the experimental part.

The compounds can inhibit topoisomerase, for example of type I and/or II, in a patient, for example a mammal such as man, by administration to this patient of a therapeutically effective quantity of a compound of formula (B1) or a compound of formula (B2).

The compounds according to the invention also have an anti-tumoral activity. They can be used for the treatment of tumors, for example tumors expressing a topoisomerase, in a patient by administration to the latter of a therapeutically effective quantity of a compound of formula (B1) or a compound of formula (B2). Examples of tumors or cancers include cancers of the oesophagus, the stomach, the intestines, the rectum, the oral cavity, the pharynx, the larynx, the lung, the colon, the breast, the cervix uteri, the corpus endometrium, the ovaries, the prostate, the testicles, the bladder, the kidneys, the liver, the pancreas, the bone, the connective tissues, the skin, the eyes, the brain and the central nervous system, as well as cancer of the thyroid, leukemia, Hodgkin's disease, lymphomas other than those related to Hodgkin, multiple myelomas and others.

They can also be used for the treatment of parasitic infections by inhibition of the hemoflagellates (for example in trypanosomia or leishmania infections) or by inhibition of the plasmodia (such as for example in malaria), but also the treatment of viral infections and diseases.

These properties make the products of formula (B1) and (B2) suitable for pharmaceutical use. A subject of the present Application is also, as medicaments, the products of formula (B1) and (B2) as defined above as well as the addition salts with pharmaceutically acceptable mineral or organic acids of said products of formula (B1) and (B2), as well as the pharmaceutical compositions containing at least one of the medicaments as defined above as active ingredient.

An object of the invention is therefore methods of treatment of diseases related with topoisomerase I and/or topoisomerase II disorders, and especially cancer, viral and parasitic diseases, comprising the administration of a therapeutically efficient dose of a camptothecin analog, said camptothecin analog being characterized in that it features a β-hydroxy lactone instead of the α-hydroxy lactone of natural camptothecin.

Another object of the invention is methods of treatment of diseases related with topoisomerase I and/or topoisomerase II disorders, and especially cancer, viral and parasitic diseases, comprising the administration of a therapeutically efficient dose of a compound of general formula (B1) or a compound of general formula (B2).

In particular, an object of the invention is methods of treatment as previously described comprising the administration of any of the β-hydroxy lactone camptothecin analogues disclosed in the present application, especially those of general formula (HCPT) and those described in the examples.

The invention also relates to pharmaceutical compositions containing a compound according to the invention or an addition salt with a pharmaceutically acceptable acid of it, in combination with a pharmaceutically acceptable support according to the chosen administration method (for example oral, intravenous, intraperitoneal, intramuscular, transdermic or sub-cutaneous). The pharmaceutical composition (for example therapeutic) can be in the form of a solid, liquid, liposome or lipidic micella.

The pharmaceutical composition can be in solid form, for example, powders, pills, granules, tablets, liposomes, gelatin capsules or suppositories. The pill, tablet or gelatin capsule can be covered in a substance which is capable of protecting the composition from the action of gastric acid or enzymes in the stomach of the subject for a sufficient period of time to allow this composition to pass in a non-digested form into the small intestine of the latter. The compound can also be administered locally, for example, at the same location as the tumor. The compound can also be administered according to a sustained release process (for example a sustained release composition or an infusion pump). The appropriate solid supports can be, for example, calcium phosphate, magnesium stearate, magnesium carbonate, talc, sugars, lactose, dextrin, starch, gelatin, cellulose, methyl cellulose, sodium carboxymethyl cellulose, polyvinylpyrrolidine and wax. The pharmaceutical compositions containing a compound according to the invention can also be presented in liquid form such as, for example, solutions, emulsions, suspensions or a sustained release formulation. The appropriate liquid supports can be, for example, water, organic solvents such as glycerol or glycols such as polyethylene glycol, similarly their mixtures, in varied proportions, in water.

A subject of the invention is also the use of the products of formula (B1) or (B2) as defined above for the preparation of medicaments intended to inhibit topoisomerase and more particularly topoisomerase of type I or type II, medicaments intended for the treatment of tumors, medicaments intended for the treatment of parasitic infections, as well as medicaments intended for the treatment of viral diseases.

Of course, the products of general formula (HCPT), (I), (II), (I)$_{OP}$ and (II)$_{OP}$ can be used according to the invention analogously to the products of formula (B1) or (B2).

The dose of a compound according to the present invention envisaged for the treatment of the diseases or disorders mentioned above, varies according to the administration method, the age and body weight of the subject as well as the state of the latter and it will be decided definitively by the attending doctor or vet. Such a quantity determined by the attending doctor or vet is called here "effective therapeutic quantity".

Unless defined in another manner, all the technical and scientific terms used here have the same meaning as that commonly understood by an ordinary specialist in the field to which the invention belongs. Similarly, all publications, Patent Applications, all Patents and all other references mentioned here are incorporated by way of reference.

The following examples are presented to illustrate the above procedures and must in no case be considered as a limit to the scope of the invention.

EXPERIMENTAL PART

Example 1 tert-butyl 3-hydroxy-3-[8-(hydroxymethyl)-9-oxo-9,11-dihydroindolizino[1,2-b]quinolin-7-yl]pentanoate 1.a. 4-ethyl-3,4-dihydroxy-1,3,4,12-tetrahydro-14H-pyrano[3',4':6,7]indolizino[1,2-b]quinolin-14-one Sodium borohydride (14 g, 370 mmol) is added by portions to a suspension of (S)-(+)-camptothecin (14 g, 40 mmol, which can be obtained from different commercial sources such as Aldrich Chemical Co. (Milwaukee, Wis.)), in methanol (750 ml) and the resultant mixture is heated gently to 55° C. in order to obtain a limpid solution which is then agitated for 16 hours at ambient temperature. The solvent is then evaporated off under reduced pressure, the residue is taken up in water (250 ml), neutralized by the addition of acetic acid (21 ml) and left at rest for 2 hours at 4° C. The resultant suspension is filtered and washed successively with cold water, acetone and diethyl ether, which allows the sought product to be obtained, after drying under reduced pressure, in the form of a white solid m.p. 280° C.

1.b. (9-oxo-7-propionyl-9,11-dihydroindolizino[1,2-b]quinolin-8-yl)methyl formate A solution of sodium metaperiodate (14 g, 65 mmol) in water (140 ml) is added dropwise to a suspension of 4-ethyl-3,4-dihydroxy-1,3,4,12-tetrahydro-14H-pyrano[3',4':6,7]indolizino[1,2-b]quinolin-14-one (13.4 g, 38 mmol) in glacial acetic acid (720 ml) and the resultant solution is agitated for one hour at ambient temperature. The reaction mixture is then poured into an ice/water mixture (650 ml) and the resultant suspension is then agitated for half an hour then filtered and washed successively with water, isopropyl alcohol and diethyl ether, which allows the sought product (11.5 g) to be obtained, after drying under reduced pressure, in the form of a pale yellow solid m.p. >200° C. (d).

1.c. tert-butyl 3-hydroxy-3-[8-(hydroxymethyl)-9-oxo-9,11-dihydroindolizino[1,2-b]quinolin-7-yl]pentanoate A suspension of zinc (6.5 g, 100 mmol) stirred with a magnetic stirrer in anhydrous diethyl ether (50 ml) under argon, is activated by the dropwise addition of chlorotrimethylsilane (0.75 ml, 5.7 mmol). Stirring is continued for 15 minutes at ambient temperature then the reaction medium is heated to reflux. The heating bath is then removed and tert-butyl bromoacetate (15 ml, 100 mmol) is added dropwise at a rate which ensures reflux is maintained. The external heating is put back and heating is continued for one hour. The resultant ethereal solution of Reformatsky's reagent is left to cool down to ambient temperature then transferred using a cannula into a suspension of (9-oxo-7-propionyl-9,11-dihydroindolizino[1,2-b]quinolin-8-yl) methyl formate (1.6 g, 4.7 mmol) in anhydrous tetrahydrofuran (40 ml) under argon. The reaction mixture is agitated under reflux for one hour, then left to cool down to ambient temperature and the reaction is stopped by the addition of saturated ammonium chloride (100 ml) and extraction is carried out with chloroform (3×100 ml). The combined chloroformic extracts are dried over sodium sulphate, evaporated and the residue is purified by chromatography on a silica gel column (1–2% MeOH/CH$_2$Cl$_2$), which allows 0.64 g (31%) of sought product to be obtained in the form of a pale yellow solid, m.p. 146–149° C.

NMR-1H (CDCl$_3$): 0.93 (t, 3H); 1.37 (s, 9H); 1.99 (m, 2H); 2.97 (dd, 2H); 3.5 (se, 1H); 5.10 (s, 2H); 5.24 (s, 2H); 7.40 (s, 1H); 7.59 (t, 1H); 7.83 (t, 1H); 7.90 (d, 1H); 8.20 (d, 1H); 8.34 (s, 1H). NMR-C13 (CDCl$_3$): 8.18; 27.90; 34.59; 45.34; 49.91; 58.55; 77.39; 82.42; 100.52; 127.67; 127.97; 128.10; 128.64; 129.44; 129.79; 130.42; 130.99; 142.86; 148.69; 152.75; 155.16; 162.38; 172.24. IR (KBr): 764; 1016; 1157; 1580; 151; 1726.

Example 2

Ethyl 3-hydroxy-3-[8-(hydroxymethyl)-9-oxo-9,11-dihydroindolizino[1,2-b]quinolin-7-yl]pentanoate A suspension of zinc (500 mg, 7.64 mmol) and (9-oxo-7-propionyl-9,11-dihydroindolizino[1,2-b]quinolin-8-yl)

methyl formate (400 mg, 1.15 mmol) in anhydrous tetrahydrofuran (20 ml) containing 10 mg of hydroquinone is heated to reflux under argon. The heating bath is removed and the exothermic reaction is initiated by the addition of a drop of ethyl bromoacetate and a small crystal of iodine. Reflux is maintained by the dropwise addition of ethyl bromoacetate (500 μl, 4.48 mmol) then the reaction mixture is again heated to reflux for one hour. After cooling down to ambient temperature, the reaction is stopped by the addition of saturated ammonium chloride (10 ml) and methanol (30 ml). The resultant mixture is agitated for 5 minutes then filtered and evaporated. The residue is dissolved in dichloromethane (30 ml), washed with water and dried over sodium sulphate. Then the solvent is eliminated and purification using column chromatography is carried out (SiO$_2$, CH$_2$Cl$_2$/MeOH 98/2), which produces 230 mg (49%) of sought compound in the form of a yellow solid, m.p. 157–161° C.

NMR-$^1$H (CDCl$_3$): 0.93 (t, 3H); 1.20 (t, 3H); 2.02 (m, 2H); 3.07 (dd, 2H); 4.11 (q, 2H); 4.9 (se, 1H); 5.08 (s, 2H); 5.23 (s, 2H); 7.45 (s, 1H); 7.62 (t, 1H); 7.80 (t, 1H); 7.90 (d, 1H); 8.22 (d, 1H); 8.36 (s, 1H). NMR-C$^{13}$ (CDCl$_3$): 8.09; 14.01; 34.67; 44.85; 49.94; 58.31; 61.09; 77.21; 100.78; 127.78; 127.96; 128.11; 128.72; 129.16; 129.65; 130.60; 131.32; 142.76; 148.28; 152.55; 155.09; 162.22; 172.59. IR (KBr): 766; 1009; 1184; 1582; 1647; 1750.

Example 3

5-ethyl-5-hydroxy-1,4,5,13-tetrahydro-3H,15H-oxepino[3',4':6,7]indolizino[1,2-b]quinoline-3,15-dione tert-butyl 3-hydroxy-3-[8-(hydroxymethyl)-9-oxo-9,11-dihydroindolizino[1,2-b]quinolin-7-yl]pentanoate (1.45 g, 3.32 mmol) is dissolved in anhydrous dichloromethane (25 ml) and treated with a saturated solution of hydrogen chloride in dichloromethane (100 ml). The resultant mixture is maintained at −20° C. for 16 hours. The precipitate is filtered, washed with methanol and dried under reduced pressure, which allows 662 mg (55%) of sought product to be obtained in the form of a yellow solid, m.p. >300° C.

NMR-$^1$H (DMSO): 0.90 (t, 3H); 1.20 (q, 2H); 3.27 (dd, 2H); 5.29 (s, 2H); 5.49 (dd, 2H); 7.42 (s, 1H); 7.73 (t, 1H); 7.90 (t, 1H); 8.16 (t, 2H); 8.71 (s, 1H). NMR-C$^{13}$ (DMSO): 8.45; 36.48; 42.54; 50.68; 61.44; 73.34; 99.78; 122.71; 127.83; 128.15; 128.75; 129.08; 130.07; 130.61; 131.81; 144.66; 148.04; 152.80; 155.91; 159.26; 172,08. IR (KBr): 761; 1127; 1204; 1285; 1580; 1653; 1757.

Example 4

3-hydroxy-3-[8-(hydroxymethyl)-9-oxo-9,11-dihydroindolizino[1,2-b]quinolin-7-yl]pentanoic acid An aqueous solution of potassium hydroxide (0.1N, 30ml) is added 5-ethyl-5-hydroxy-1,4,5,13-tetrahydro-3H,15H-oxepino[3',4':6,7]indolizino[1,2-b]quinoline-3,15-dione (500 mg, 1.38 mmol) and the resultant suspension is agitated at ambient temperature for 16 hours, which produces a virtually limpid solution which is filtered. The filtrate is acidified to pH 3.5 with 1N hydrochloric acid, and the yellow precipitate is recovered by filtration, washed with water and with acetone then dried under reduced pressure. 415 mg (79%) of sought compound is obtained in the form of a monohydrate, m.p. 165–167° C.

NMR-$^1$H (DMSO): 0.82 (t, 3H); 2.10 (m, 2H); 2.83 (d, 2H); 3.12 (d, 2H); 3.25 (se, 1H); 4.81 (s, 2H); 5.26 (s, 2H); 5.76 (se, 1H); 7.38 (s, 1H); 7.71 (t, 1H); 7.84 (t, 1H); 8.10 (d, 1H); 8.18 (d, 1H); 8.34 (s, 1H); 12.15 (se, 1H). NMR-C$^{13}$ (DMSO): 8.16; 34.80; 46.71; 50.36; 55.73; 76.53; 100.17; 127.50; 128.00; 128.26; 128.69; 129.06; 130.01; 130.45; 131.63; 142.57; 148.09; 153.19; 156.07; 161.22; 172.27. IR(KBr): 1020; 1188; 1413; 1586; 1651; 1694.

Example 5 methyl 3-hydroxy-3-[8-(methoxymethyl)9-oxo-9,11-dihydroindolizino[1,2-b]quinolin-7-yl]pentanoate 5-ethyl-5-hydroxy-1,4,5,13-tetrahydro-3H,15H-oxepino[3',4:6,7]indolizino[1,2-b]quinoline-3,15-dione (180 mg, 0.5 mmol), in suspension in methanol (50 ml) is treated with 6N dry hydrogen chloride in methanol (0.5 ml) and maintained under reflux until complete dissolution (4 hours). The volatile compounds are evaporated off and the residue is dissolved in dichloromethane (50 ml), washed with dilute sodium hydroxide (0.05 N, 15 ml) and brine (15 ml). The organic fraction is dried over sodium sulphate and evaporated. The solid residue is purified by chromatography in a silica gel column (MeOH at 3%/CH$_2$Cl$_2$) and the purified product is taken up in diethyl ether, filtered and dried, which produces 120 mg (58%) of sought compound in the form of a pale yellow solid, m.p. 163–166° C.

NMR-$^1$H (CDCl$_3$): 0.93 (t, 3H); 1.2 (m, 2H); 3.05 (dd, 2H); 3.49 (s, 3H); 3.62 (s, 3H); 4.93 (s, 2H); 5.22 (d, 2H); 5.52 (s, 1H); 7.21 (s, 1H); 7.62 (t, 1H); 7.81 (t, 1H); 7.91 (d, 1H); 8.22 (d, 1H); 8.36 (s, 1H). NMR-C$^{13}$ (CDCl$_3$): 7.74; 35,54; 46.82; 50.15; 51.67; 58.10; 65.33; 78.03; 100.17; 125.57; 127.70; 128.04; 128.10; 128.35; 129.53; 130.39; 130.94; 143.87; 148.75; 152.94; 157.83; 161.74; 171.35. IR (KBr): 1207; 1595; 2655; 1709.

Example 6 ethyl 2,2-difluoro-3-hydroxy-3-[8-(hydroxymethyl)-9-oxo-9,11-dihydroindolizino[1,2-b]quinolin-7-yl]pentanoate Approximately half of a total quantity of ethyl bromodifluoroacetate (1.8 ml, 14 mmol), (9-oxo-7-propionyl-9,11-dihydroindolizino[1,2-b]quinolin-8-yl)methyl formate (2,0 g, 5.75 mmol, as obtained in Stage 1.b.) in suspension in anhydrous THF (10 ml), are added dropwise under argon to a suspension of zinc (1.25 g, 17.2 mmol) in anhydrous THF under reflux (40 ml) then the remaining part of the ethyl bromodifluoroacetate is added. The reaction mixture is maintained under reflux for another half an hour. After cooling down to ambient temperature, the reaction is stopped by the addition of saturated ammonium chloride (20 ml) and the reaction mixture is extracted with dichloromethane (3×20 ml). The combined organic extracts are dried and concentrated. The residue is taken up in diethyl ether (10 ml), filtered and purified by column chromatography (SiO$_2$, CH$_2$Cl$_2$/MeOH:98/2), which produces 664 mg (26%) of product in the form of a yellow solid, m.p. 208–209° C.

NMR-$^1$H (CDCl$_3$): 0.91 (t, 3H); 1.38 (t, 3H); 2.32 (m, 2H); 4.8 (se, 1H); 4.38 (q, 2H); 5.09 (d, 2H); 5.13 (dd, 2H); 7.42 (s,1H); 7.55 (t, 1H); 7.72 (t, 1H); 7.79 (d, 1H); 8.08 (d, 1H); 8.22 (s, 1H). NMR-C$^{13}$ (CDCl$_3$): 6.97; 13.93; 28.63; 50.18; 56.27; 63.15; 77.20; 81.96 (t); 101.27; 116.40 (t); 127.67; 127.77; 127.97; 128.31; 129.26; 130.33; 130.94; 131.23; 143.16; 148.34; 150.20; 151.91; 161.21; 163.21 (t). IR(KBr): 1124; 1308; 1591; 1647; 1748.

Example 7 ethyl 3-hydroxy-3-(8-methyl-9-oxo-9,11-dihydroindolizino[1,2-b]quinolin-7-yl)pentanoate A suspension of zinc (1.25 g, 19.1 mmol), 8-methyl-7-propionylindolizino[1,2-b]quinoline-9-(11H)-one (500 mg, 1.43 mmol, as obtained by Kingsburry, W. D., Tetrahedron Lett. 29:6847 (1988)) and silver acetate (250 mg, 1.50 mmol) in anhydrous tetrahydrofuran (10 ml) is agitated at ambient temperature under an argon atmosphere. After 10 minutes, the reaction mixture is activated by the dropwise addition of a molar solution of chlorodiethylaluminium (10 ml, 10 mmol), then ethyl bromoacetate (1.25 ml, 11.3 mmol) is added dropwise and the resultant mixture is left to react for another 5 hours. The reaction is stopped by the successive addition of ethyl alcohol (10 ml) and a saturated solution of potassium and sodium tartrate (10 ml). The resultant mixture is agitated for another hour, filtered and concentrated under reduced pressure. The residue is taken up in dichloromethane (30 ml), washed with water, dried, concentrated and purified by column chromatography ($SiO_2$, $CH_2Cl_2$/MeOH:98/2), which produces 93 mg (15%) of desired product in the form of a pale yellow solid, m.p. 185–188° C.

NMR-$^1$H (CDCl$_3$): 0.91 (t, 3H); 1.17 (t, 3H); 1.99 (m, 2H); 2.49 (s, 3H); 3.10 (dd, 2H); 4.11 (q, 2H); 4.6 (se, 1H); 5.25 (s, 2H); 7.65 (t, 1H); 7.67 (s, 1H); 7.80 (t, 1H); 7.90 (d, 1H); 8.22 (d, 1H); 8.34 (s, 1H). NMR-C$^{13}$ (CDCl$_3$): 8.02; 13.99; 14.72; 33.14; 43.97; 50.02; 61.0; 76.54; 101.90; 127.65; 127.84; 128.08; 128.81; 128.88; 130.74; 131.59; 131.65; 140.33; 147.64; 152.96; 153.61; 162.11; 172.91. IR (KBr): 762; 1192; 1576; 1653; 1740.

Example 8 tert-butyl 3-{8-[(acetyloxy)methyl]-9-oxo-9,11-dihydroindolizino[1,2-b]quinolin-7-yl}-3-hydroxypentanoate Acetic anhydride (70 μl, 0.7 mmol) is added dropwise to a solution of tert-butyl 3-hydroxy-3-[8-(hydroxymethyl)-9-oxo-9,11-dihydroindolizino[1,2-b]quinolin-7-yl]pentanoate (200 mg, 0.46 mmol) and triethylamine (140 μl, 1 mmol) in dichloromethane (5 ml) and the resultant mixture is agitated at ambient temperature for 21 hours. The volatile components are evaporated off and the residue is purified by chromatography on a silica gel column (1–2% MeOH/$CH_2Cl_2$), which produces 152 mg of sought compound in the form of a yellow solid, m.p. 195–196° C.

NMR-$^1$H (CDCl$_3$): 0.88 (t, 3H); 1.32 (s, 9H); 1.93 (m, 2H); 2.07 (s, 3H); 2.97 (dd, 2H); 4.8 (se, 1H); 5.28 (s, 2H); 5.59 (dd, 2H); 7.39 (s, 1H); 7.63 (t, 1H); 7.80 (t, 1H); 7.90 (d, 1H); 8.23 (d, 1H); 8.34 (s, 1H). NMR-C$^{13}$ (CDCl$_3$): 8.02; 21.06; 27.91; 35.05; 45.58; 50.16; 59.23; 77.52; 82.26; 100.59; 124.21; 127.91; 128.10; 128.14; 128.97; 129.18; 130.68; 131.46; 142.85; 148.29; 152.43; 158.49; 161.83; 171.13; 171.90.

Example 9

5,12-diethyl-5-hydroxy-1,4,5,13-tetrahydro-3H,15H-oxepino[3',4':6,7]indolizino[1,2-b]quinoline-3,15-dione This compound is prepared in a similar manner to Example 1, except that in Stage 1.a., 7-ethyl camptothecin (Sawada and collaborators, Chem. Pharm. Bull. 39:2574 (1991)) is used instead of camptothecin. The sought compound is obtained in the form of a vivid yellow solid, m.p. >270° C.

NMR-$^1$H (DMSO): 0.92 (t, 3H); 1.39 (t, 3H); 1.93 (q, 2H); 3.08 (d, 2H); 3.25 (q, 2H); 3.51 (d, 2H); 5.32 (s, 2H); 5.52 (dd, 2H); 7.42 (s, 1H); 7.76 (t, 1H); 7.89 (t, 1H); 8.18 (d, 1H); 8.32 (d, 1H). NMR-C$^{13}$ (DMSO): 8.46; 14.15; 22.42; 36.50; 42.54; 49.95; 61.45; 73.35; 99.68; 122.61; 124.27; 126.76; 127.70; 128.27; 129.92; 130.18; 145.17; 145.82; 148.57; 152.15; 155.89; 159.26; 172.08.

Example 10

3-[12-ethyl-5-(hydroxymethyl)-9-oxo-9,11-dihydroindolizino[1,2-b]quinolin-7-yl]-3-hydroxypentanoic acid This compound is prepared in a similar manner to Example 4, 5,12-diethyl-5-hydroxy-1,4,5,13-tetrahydro-3H,15H-oxepino[3',4':6,7]indolizino[1,2-b]quinoline-3,15-dione is used instead of the 5-ethyl-5-hydroxy-1,4,5,13-tetrahydro-3H,15H-oxepino[3',4':6,7]indolizino[1,2-b]quinoline-3,15-dione. It is presented in the form of a slightly dirty white solid, m.p. 238–239° C.

NMR-$^1$H (DMSO): 0.82 (t, 3H); 1.35 (t, 3H); 2.01 (m, 2H); 2.85 (d, 2H); 3.18 (d, 2H); 3.22 (q, 2H); 4.81 (s, 2H); 5.00 (se, 1H); 5.24 (s, 2H); 5.78 (se, 1H); 7.38 (s, 1H); 7.77 (t, 1H); 7.86 (t, 1H); 8.18 (d, 1H); 8.28 (d, 1H); 12.10 (se, 1H). NMR-C$^{13}$ (DMSO): 8.12; 14.15; 22.41; 34.78; 46.74; 49.65; 55.7 1; 76.51; 100.04; 124.22; 126.63; 127.48; 128.12; 128.21; 129.94; 130.02; 143.10; 145.59; 148.69; 152.62; 156.03; 161.22; 172.22.

Example 11

8-ethyl-8-hydroxy-2,3,8,9,12,15-hexahydro-10H,13H-[1,4]dioxino[2,3-g]oxepino[3',4':6,7]indolizino[1,2-b]quinoline-10,13-dione 11.a. 4-(2-ethyl-1,3-dioxolan-2-yl)-2-methoxypyridine (F)

The water is distilled in an azeotropic manner (overnight) with a Dean Stark apparatus from a mixture of 2-chloro-4-propionylpyridine (10 g, 59 mmol) obtained as in Lamattina, J. L. *J.Heterocyclic Chem*. 20, p. 553 (1983), ethylene glycol (20 ml) and p-toluenesulphonic acid (250 mg) in toluene (150 ml). The solvent is then eliminated under reduced pressure, the acid is neutralized with saturated aqueous sodium bicarbonate (100 ml) and the product is extracted with ether. The combined ethereal extracts are washed with brine, dried over sodium sulphate and evaporated, which produces 13.3 g (96%) of crude product protected by the carbonyl group which is heated to reflux with 3 equivalents of sodium methoxide in acetonitrile until the end of the reaction (checked by thin layer chromatography: $SiO_2$, tert-butyl methyl oxide/hexane (TBMO/HX) 50/50). The acetonitrile solution is then filtered and evaporated. The residue is taken up in ether, washed with water and with brine, dried over sodium sulphate and evaporated, which produces a brown oil which is distilled (70–75° C., 0.04 mbar); 10.7 g (overall yield 81%) of product (F) is collected in the form of a clear oil.

11.b. [4-(2-ethyl-1,3-dioxolan-2-yl)-2-methoxy-3-pyridinyl]methanol (G)

tert-butyllithium (1.7 M in pentane, 100 ml, 170 mmol) is added dropwise using a cannula to a solution of bromomesitylene (13 ml, 85 mmol) in anhydrous tetrahydrofuran (300 ml) at −78° C. and under argon. The resultant white precipitate is agitated at −78° C. for one hour then 4-(2-ethyl-1,3-dioxolan-2-yl)-2-methoxypyridine (10 g, 44.8 mmol) is added and the reaction mixture is agitated for 15 minutes at −78° C., for one hour at 0° C. and for one hour at ambient temperature. After again cooling down to −78° C., anhydrous N,N-dimethylformamide (100 mmol) is added and the reaction mixture is left to heat up to ambient temperature then agitated for 16 hours, after which analysis by thin layer chromatography (SiO$_2$, TBMO/HX: 50/50) reveals the complete consumption of the starting product The reaction is stopped with saturated ammonium chloride and the reaction mixture is extracted with diethyl ether (200 ml, 50 ml, 50 ml). The combined extracts are dried over sodium sulphate and evaporated, which produces a yellow oil which is purified by column chromatography (SiO$_2$, TBMO/HX: 0/100 to 5/95 to elute the mestylene derivatives then 20/80 to 50/50 to elute the product) in order to obtain the intermediate aldehyde (7 g). The aldehyde is dissolved in methanol (100 ml) and treated with sodium borohydride (5 g, 132 mmol) and the resultant mixture is agitated until complete consumption of the intermediate aldehyde (approximately 1 hour) with analytical control by thin layer chromatography. The solvent is then evaporated off, the residue is taken up in ether, washed with water and with brine, dried and the solvent is evaporated off. Column chromatography (SiO$_2$, TBMO/HX: 10/90 to 50/50) of the residue produces 7 g (overall yield 62%) of product (G) in the form of a yellow oil.

11.c. 3-[(benzyloxy)methyl]-4-(2-ethyl-1,3-dioxolan-2-yl)-2-methoxypyridine (H)

A solution of [4-(2-ethyl-1,3-dioxolan-2-yl)-2-methoxy-3-pyridinyl]methanol (7 g, 30 nmol) and benzyl chloride (5 ml, 45 mmol) in anhydrous tetrahydrofuran (50 ml) is added dropwise to a suspension of sodium hydride (80% in mineral oil, 1.85 g, 61 mmol) in anhydrous tetrahydrofuran (100 ml) and the reaction mixture is maintained under reflux for 16 hours. The reaction mixture is then left to cool down to ambient temperature, the reaction is stopped with water (50 ml) and the reaction mixture is concentrated under reduced pressure. The residue is dissolved in diethyl ether (150 ml) and washed with water and with brine, dried and evaporated. Purification by column chromatography (SiO$_2$, TBMO/IX: 5/95 to 20/80) produces the product protected by the benzyl (H), 9 g, (87%) in the form of a limpid oil.

11.d. 1-{3-[(benzyloxy)methyl]-2-methoxy-4-pyridinyl}-1-propanone (I')

3-[(Benzyloxy)methyl]-4-(2-ethyl-1,3-dioxolan-2-yl)-2-methoxypyridine (9 g, 27 mmol) is treated with trifluoroacetic acid (10 ml) and water (5 ml) at a bath temperature of 120° C. for 3 hours. The reaction mixture is concentrated under reduced pressure and the residual traces of acids are neutralized by the addition of saturated aqueous sodium bicarbonate. Extraction is carried out with ether followed by column chromatography (SiO$_2$, TBMO/HX: 10/90) which produces 5.5 g (70%) of product (I).

11.e. tert-butyl 3-{3-[(benzyloxy)methyl]-2-methoxy-4-pyridinyl}-3-hydroxypentanoate (J)

tert-butyl bromoacetate (13 ml, 80 mmol) is added dropwise to a zinc suspension (5.3 g, 80 mmol activated with 6N HCl over 10 seconds, then washed successively with water until a neutral pH is achieved, with acetone and with diethyl ether) in anhydrous tetrahydrofuran (60 ml) under reflux. The reaction medium is maintained under reflux for another 10 minutes after the addition is terminated. Then, a solution of 1-{3-[(benzyloxy)methyl]-2-methoxy-4-pyridinyl}-1-propanone (5.8 g, 20 mmol) in anhydrous tetrahydrofuran (20 ml) is added and the reaction mixture is agitated under reflux for another hour. The reaction is stopped at 0° C. with saturated aqueous ammonium chloride (100 ml) and the reaction mixture is extracted with diethyl ether. The combined extracts are dried over sodium sulphate and evaporated, which produces a yellow oil which is purified by column chromatography (SiO$_2$, TBMO/HX: 5/95 to 10/90) in order to obtain the tert-butyl ester (J) (7 g, 95%) in the form of a limpid liquid.

11.f. tert-butyl 3-hydroxy-3-[3-(hydroxymethyl)-2-methoxy-4-pyridinyl]pentanoate (K)

tert-Butyl 3-{3-[(benzyloxy)methyl]-2-methoxy-4pyridinyl}-3-hydroxypentanoate (1 g, 2.5 numol) is subjected to hydrogenolysis at atmospheric pressure and at ambient temperature using 5% palladium on carbon as catalyst (50 mg) and absolute ethanol as solvent (10 ml). Once the reaction has terminated (6 hours), the catalyst is separated by filtration and the solvent is evaporated off, which leaves 0.7 g (90%) of product (K) of a sufficient purity for a subsequent synthetic use.

11.g. 5-ethyl-5-hydroxy-9-methoxy-4,5-dihydrooxepino[3,4-c]pyridin-3(1H)-one (L)

tert-butyl 3-hydroxy-3-[3-(hydroxymethyl)-2-methoxy-4-pyridinyl]pentanoate (8.8 g, 28 mmol) is treated with trifluoroacetic acid (30 ml) for 3 hours at ambient temperature. The volatile components are evaporated off and the residue is purified by column chromatography (SiO$_2$, CH$_2$Cl$_2$/MeOH: 100/0 to 98/2), which produces a limpid oil which, after treatment with toluene, produces 5.9 g of product (L) (89%) in the form of white crystals, m.p. 97–98° C.

11.h. 5-ethyl-5-hydroxy-1,4,5,8-tetrahydrooxepino[3,4-c]pyridine-3,9-dione (M)

5-Ethyl-5-hydroxy-9-methoxy-4,5-dihydrooxepino[3,4-c]pyridin-3(1H)-one (0.5 g, 2.1 mmol) is heated under reflux for 9 hours in 1N hydrochloric acid (20 ml). The reaction mixture is concentrated under reduced pressure and the residue is again dried by the addition and evaporation of toluene twice, then left overnight under reduced pressure in the presence of phosphorus pentoxide. The resultant oil is dissolved in anhydrous acetonitrile (5 ml) and agitated under argon for 24 hours. The precipitate is filtered out and dried, which produces 0.23 g (49%) of a white solid (M), m.p. 118–119° C.

11.i. (7-iodo-2,3-dihydro[1,4]dioxino[2,3-g]quinolin-8-yl)methanol (N)

The procedures described by Meth-Cohn et al., J. Chem. Soc. Perkin Trans. I, p. 1520 (1981); Meth-Cohn, J. Chem. Soc. Perkin Trans. I, p. 2509 (1981); and Nakasimhan et al J. Am. Chem. Soc. 112, p. 4431 (1990), are used. N-(2,3-dihydro-1,4-benzodioxin-6-yl)acetamide (22 g, 113 mmol) is added to the Vilsmeyer reagent obtained by the dropwise addition of phosphoryl oxychloride (71 ml, 0.77 mol) to anhydrous dimethylfonnamide (23 ml, 0.28 mol), cooled down with a water/ice bath and agitated again for 0.5 hours under an argon atmosphere. The resultant mixture is heated at 75° C. for 16 hours. After cooling down to ambient temperature, the reaction mixture is added to a mixture of ice and water (300 ml) and extracted with dichloromethane (5×200 ml). The combined organic extracts are dried over sodium sulphate, filtered and concentrated. The solid residue is suspended in dichloromethane (20 ml), filtered and dried under reduced pressure, which produces 10 g (35%) of 7-chloro-2,3-dihydro[1,4]dioxino[2,3-g]quinoline-8-carbaldehyde in the form of a yellow solid, m.p. 222–224° C. This intermediate is treated with sodium iodide (30 g, 0.2 mol) and concentrated hydrochloric acid (1.5 ml) in acetonitrile under reflux (150 ml) for 24 hours. After cooling down to ambient temperature, the solvent is eliminated under reduced pressure and the residue is taken up in aqueous tetrahydrofuran at 50% (200 ml), filtered, washed with tetrabydrofuran and dried under reduced pressure, which produces 12 g of 7-iodo-2,3-dihydro[1,4]dioxino[2,3-g]quinoline-8-carbaldehyde in the form of a yellow solid, m.p. 155–157° C. The above intermediate is treated with sodium borohydride (2 g, 52 mmol) in methanol (200 ml) at ambient temperature for 0.5 hours. The solvent is eliminated under reduced pressure and the residue is taken up in water and filtered. The resultant solid is dried under reduced pressure in the presence of phosphorus pentoxide, which produces 11 g of (7-iodo-2,3-dihydro[1,4]dioxino[2,3-g]quinolin-8-yl)methanol in the form of a yellow solid, m.p. 178–180° C.

11.j. 5-ethyl-5-hydroxy-8-[(7-iodo-2,3-dihydro[1,4]dioxino[2,3-g]quinolin-8-yl)methyl]-1,4,5,8-tetrahydrooxepino[3,4-c]pyridine-3,9-dione (O)

Diethyl azodicarboxylate (570 l, 3.6 mmol) is added dropwise over 5 minutes to a solution of 5-ethyl-5-hydroxy-1,4,5,8-tetrahydrooxepino[3,4-c]pyridine-3,9-dione (400 mg, 1.79 mmol), the compound obtained in the preceding Stage, 11 .i. (770 mg, 2.23 mmol) and triphenylphosphine (934 mg, 3.58 mmol) in a mixture of anhydrous THF/DMSO (8/1 v/v, 45 ml) and the resultant mixture is agitated under argon at ambient temperature for 16 hours. The reaction mixture is then concentrated under reduced pressure and the residue is dissolved in chloroform (100 ml). The resultant solution is washed with brine (4×50 ml), dried over sodium sulphate and evaporated. The residue is purified by column chromatography (SiO$_2$, CH$_2$Cl$_2$/MeOH: 99/1 to 98/2), which produces 650 mg (66%) of product (O) in the form of a white solid, m.p. 165–167° C.

11.k. 8-ethyl-8-hydroxy-2,3,8,9,12,15-hexahydro-10H,13H-[1,4]dioxino[2,3-g]oxepino[3',4':6,7]indolizino[1,2-b]quinoline-10,13-dione 5-ethyl-5-hydroxy-8-[(7-iodo-2,3-dihydro[1,4]dioxino[2,3-g]quinolin-8-yl)methyl]-1,4,5,8-tetrahydrooxepino[3,4-c]pyridine-3,9-dione (600 mg, 1.1 mmol), tetrabutylammonium bromide (352 mg, 1.1 mmol), sodium acetate (359 mg, 4.4 mmol) and palladium II acetate (98 mg, 0.43 mmol) are dissolved in anhydrous acetonitrile (40 ml) and heated at 90° C. under argon for 16 hours. After cooling down to ambient temperature, a white precipitate is separated from the reddish solution. This precipitate is filtered out and dried under reduced pressure. The crude product is suspended in water, filtered and dried under reduced pressure over phosphorus pentoxide which produces 250 mg of sought compound in the form of a clear yellow solid, m.p. >250° C.

NMR-$^1$H (DMSO): 0.91 (t, 3H); 1.87 (m, 2H); 3.08 (d, 1H); 3.51 (d, 1H); 4.45 (s, 4H); 5.19 (s, 2H); 5.47 (dd, 2H); 6.02 (se, 1H); 7.33 (s, 1H); 7.54 (s, 1H); 7.55 (s, 1H); 8.43 (s, 1H). NMR-C$^{13}$ (DMSO): 8.43; 36.47; 42.54; 50.52; 61.43; 64.43 (2C); 73.31; 99.07; 112.27; 113.14; 122.00; 124.24; 128.18; 129.74; 144.59; 145.01; 145.33; 147.63; 150.88; 155.88; 159.23; 172.07.

Example 12

10-(benzyloxy)-5-ethyl-5-hydroxy-1,4,5,13-tetrahydro-3H,15H-oxepino[3',4':6,7]indolizino[1,2-b]quinoline-3,15-dione 12.a. [6-(benzyloxy)-2-iodo-3-quinolinyl]methanol This compound is prepared in a similar manner to that indicated in Stage 11.i. of Example 11, but by using 4N-[4-(benzyloxy)phenyl]acetamide instead of N-(2,3-dihydro-1,4-benzodioxin-6-yl)acetamide. Purification by chromatography on a silica gel column and the use of dichloromethane as eluant are necessary in order to isolate the intermediate 6-(benzyloxy)-2-chloro-3-quinolinecarbaldehyde, m.p. 180–182° C. (yield 8%) with sufficient purity. Then, the halogen exchange produces 6-(benzyloxy)-2-iodo-3-quinolinecarbaldehyde, m.p. 155–157° C. and a subsequent reduction with sodium borohydride produces [6-(benzyloxy)-2-iodo-3-quinolinyl]methanol, m.p. 147–149° C.

12.b. 8-{[6-(benzyloxy)-2-iodo-3-quinolinyl]methyl}-5-ethyl-5-hydroxy-1,4,5,8-tetrahydrooxepino[3,4-c]pyridine-3,9-dione This compound is prepared in a similar manner to that indicated in Stage 11.j. of Example 11, but by using [6-(benzyloxy)-2-iodo3-quinolinyl]methanol instead of (7-iodo-2,3-dihydro[1,4]dioxino[2,3-g]quinolin-8-yl)methanol. This compound is presented in the form of a white solid m.p. 197–199° C.

12.c. 10-(benzyloxy)-5-ethyl-5-hydroxy-1,4,5,13-tetrahydro-3H,15H-oxepino[3',4':6,7]indolizino[1,2-b]quinoline-3,15-dione This compound is prepared in a similar manner to that indicated in Stage 11.k. of Example 11, but by using 8-{[6-(benzyloxy)-2-iodo-3-quinolinyl]methyl}-5-ethyl-5-hydroxy-1,4,5,8-tetrahydrooxepino[3,4-c]pyridine-3,9-dione instead of 5-ethyl-5-hydroxy-8-[(7-iodo-2,3dihydro[1,4]dioxino[2,3-g]quinolin-8-yl)methyl]-1,4,5,8-tetrahydrooxepino[3,4c]pyridine-3,9-dione. The sought compound is presented in the form of a clear yellow solid m.p. >250° C.

NMR-$^1$H (DMSO): 0.90 (t, 3H); 1.85 (m, 2H); 3.08 (d, 1H); 3.50 (d, 1H); 5.25 (s, 2H); 5.30 (s, 2H); 5.50 (dd, 2H); 6.05 (s, 1H); 7.30–7.70 (m, 8H); 8.10 (d, 1H); 8.55 (s, 1H). NMR-C$^{13}$ (DMSO): 8.43; 36.48; 38.28; 50.65; 61.42; 70.00; 73.32; 99.05; 107.71; 122.05; 123.42; 128.18; 128.26; 128.70; 129.40; 130.19; 130.48; 130.63; 136.65; 144.18; 144.90; 150.53; 155.91; 157.31; 159.24; 172.06.

Example 13

3-[2-(benzyloxy)-8-(hydroxymethyl)-9-oxo-9,11-dihydroindolizino[1,2-b]quinolin-7-yl]-3-hydroxypentanoic acid (E)

This compound is prepared in a similar manner to that indicated in Example 4, but by using 10-(benzyloxy)-5-ethyl-5-hydroxy-1,4,5,13-tetrahydro-3H,15H-oxepino[3',4':6,7]indolizino[1,2-b]quinoline-3,15-dione instead of 5-ethyl-5-hydroxy-1,4,5,13-tetrahydro-3H,15H-oxepino[3',4':6,7]indolizino[1,2-b]quinoline-3,15-dione. It is presented in the form of a yellow solid, m.p. 171–173° C.

NMR-$^1$H (DMSO): 0.80 (t, 3H); 2.00 (m, 2H); 2.85 (d, 1H); 3.15 (d, 1H); 4.80 (s, 2H); 5.25 (s, 2H); 5.30 (s, 2H); 5.75 (se, 1H); 7.30 (s, 1H); 7.35–7.70 (m, 7H); 8.10 (d, 1H); 8.55 (s, 1H). NMR-C$^{13}$ (DMSO): 8.11; 34.75; 46.68; 50.35; 55.70; 69.97; 76.51; 99.45; 107.78; 123.28; 127.64; 128.18 (2C); 128.26; 128.70 (2C); 129.33; 130.17; 130.47; 130.57; 136.69; 142.79; 144.17; 150.93; 156.03; 157.19; 161.20.

Example 14

5-ethyl-5,10-dihydroxy-1,4,5,13-tetrahydro-3H,15H-oxepino[3',4':6,7]indolizino[1,2-b]quinoline-3,15-dione 10-(benzyloxy)-5-ethyl-5-hydroxy-1,4,5,13-tetrahydro-3H,15H-oxepino[3',4':6,7]indolizino[1,2-b]quinoline-3,15- dione (370 mg, 0.79 mmol) is treated with hydrogen under atmospheric pressure and at ambient temperature using 10% palladium on carbon as catalyst (60 mg) and trifluoroacetic acid as solvent (15 ml). Once the reaction is terminated (16 hours), dichloromethane (50 ml) and methanol (50 ml) are added to the reaction mixture, the catalyst is filtered out and the volatile components are evaporated off under reduced pressure which allows the sought crude compound to be obtained containing traces of trifluoroacetic acid. These traces are eliminated by co-distillation with 1,4-dioxan. The product is obtained in the form of an orange solid, m.p. 150° C. (d), of a sufficient purity for a subsequent synthetic use.

NMR-$^1$H (DMSO): 0.89 (t, 3H); 1.85 (q, 2H); 3.02 (d, 1H); 3.45 (d, 1H); 5.19 (s, 2H); 5.37 (d, 1H); 5.50 (d, 1H); 5.98 (se, 1H); 7.26 (s, 1H); 7.31 (s, 1H); 7.40 (d, 1H); 8.00 (d, 1H); 8.42 (s, 1); 10.32 (s, 1H). NMR-$C^{13}$ (DMSO): 8.47; 36.50; 42.61; 50.57; 61.46; 73.35; 98.84; 109.02; 121.83; 123.18; 129.50; 129.85; 130.12; 130.80; 143.39; 145.10; 149.69; 155.97; 156.82; 159.30; 172.11.

Example 15

11-[(dimethylamino)methyl]-5-ethyl-5,10-dihydroxy-1,4,5,13-tetrahydro-3H,15H-oxepino[3',4':6,7]indolizino[1,2-b]quinoline-3,15-dione hydrochloride 15.a. 11-[(dimethylamino)methyl]-5-ethyl-5,10-dihydroxy-1,4,5,13-tetrahydro-3H,15H-oxepino[3',4':6,7]indolizino[1,2-b]quinoline-3,15-dione A suspension of 5-ethyl-5,10-dihydroxy-1,4,5,13-tetrahydro-3H,15H-oxepino[3',4':6,7]indolizino[1,2-b] quinoline-3,15-dione (260 mg, 0,69 mmol) in acetic acid (15 ml) is treated with aqueous formaldehyde at 37% (500 µl) and aqueous dimethylamine at 40% (500 µl) and the resultant mixture is agitated at ambient temperature for 16 hours. The reaction mixture is concentrated to dryness and the residue is purified by column chromatography (SiO$_2$, CH$_2$Cl$_2$/MeOH: 100/0 to 90/10) followed by crystallization from acetonitrile, which produces 102 mg of sought compound.

15.b. 11-[(dimethylamino)methyl]-5-ethyl-5,10-dihydroxy-1,4,5,13-tetrahydro-3H,15H-oxepino[3',4':6,7]indolizino[1,2-b]quinoline-3,15-dione hydrochloride Dilute hydrochloric acid (1N) is added dropwise to a suspension of 11-(dimethylamino)methyl-5-ethyl-4,5-dihydro-5,10-dihydroxy-1H-oxepino[3',4':6,7]-indolizino [1,2-b]quinoline-3,15(4H,13H)-dione (102 mg) in water until complete dissolution. The water is evaporated off under reduced pressure and the residue is suspended in acetonitrile (5 ml) and filtered, which produces 103 mg of the sought salt m.p. 248° C. (d).

NMR-$^1$H (DMSO): 0.88 (t, 3H); 1.85 (m, 2H); 2.84 (s, 6H); 3.08 (d, 1H); 3.5 (d, 1H); 4.73 (s, 2H); 5.25 (s, 2H); 5.47 (dd, 2H); 7.33 (s, 1H); 7.38 (s, 1H); 7.72 (d, 1H); 8.19 (d, 1H); 8.99 (s, 1H); 9.92 (se, 1H); 11.45 (s, 1H). NMR-$C^{13}$ (DMSO): 8.46; 34.36; 42.44 (3C); 50.61 (2C); 61.42; 73.35; 99.19; 108.63; 122.21; 122.36; 126.86; 129.13; 130.61; 133.09; 143.53; 144.70; 149.76; 155.98; 157.17; 159.27; 172.06.

Example 16

5-ethyl-9-fluoro-5-hydroxy-10-methoxy-1,4,5,13-tetrahydro-3H,15H-oxepino[3',4':6,7]indolizino[1,2-b]quinoline-3,15-dione This compound is obtained from 3-fluoro-4-methoxyaniline according to the method illustrated in Stages 11i, 11j and 11k of Example 11. Yellow solid, m.p. >250° C.

NMR-$^1$H (DMSO): 0.89 (t, 3H); 1.85 (q, 2H); 3.08 (d, 1H); 3.49 (d, 1H); 4.00 (s, 3H); 5.25 (s, 2H); 5.39 (d, 1H); 5.51 (d, 1H); 6.00 (s, 1H); 7.32 (s, 1H); 7.72 (d, 1H); 7.91 (d, 1H); 8.58 (s, 1H). NMR-$C^{13}$ (DMSO): 8.43; 36.48; 42.51; 50.68; 56.60; 61.42; 73.29; 99.25; 108.68; 113.52; 122.23; 126.33; 129.99; 130.30; 143.79; 144.70; 148.42; 151.18; 153.19; 155.81; 159.20; 172.06. IR (KBr): 1259; 1503; 1602; 1737.

Example 17

9-chloro-5-ethyl-5-hydroxy-10-methyl-1,4,5,13-tetrahydro-3H,15H-oxepino[3',4':6,7]indolizino[1,2-b]quinoline-3,15-dione This compound is obtained from 3-chloro-4-methylaniline according to the method illustrated in Stages 11i, 11j and 11k of Example 11. Yellow solid, m.p. >250° C.

NMR-$^1$H (DMSO): 0.85 (t, 3H); 1.85 (q, 2H); 2.55 (s, 3H); 3.07 (d, 1H); 3.45 (d, 1H); 5.25 (s, 2H); 5.39 (d, 1H); 5.51 (d, 1H); 6.05 (s, 1H); 7.39 (s, 1H); 8.10 (s, 1H); 8.20 (s, 1H); 8.60 (s, 1H). NMR-$C^{13}$ (DMSO): 8.43; 20.20; 36.47; 42.49; 50.67; 61.41; 73.28; 99.87; 122.82; 126.98; 127.99; 129.60; 130.53; 131.08; 135.64; 136.56; 144.39; 147.11; 153.10; 155.85; 159.18; 172.03. IR (KBr): 1208; 1479; 1606; 1656; 1724.

Example 18

5-ethyl-9,10-difluoro-5-hydroxy-1,4,5,13-tetrahydro-3H,15H-oxepino[3',4':6,7]indolizino[1,2-b]quinoline-3,15-dione This compound is obtained from 3,4-difluoroaniline according to the method illustrated in Stages 11i, 11j and 11k of Example 11. Yellow solid; m.p. >250° C.

NMR-$^1$H (DMSO): 0.85 (t, 3H); 1.85 (q, 2H); 3.07 (d, 1H); 3.47 (d, 1H); 5.25 (s, 2H); 5.39 (d, 1H); 5.51 (d, 1H); 6.05 (s, 1H); 7.39 (s, 1H); 8.15 (q, 1H); 8.25 (q, 1H); 8.68 (s, 1H). NMR-$C^{13}$ (DMSO): 8.41; 36.45; 42.48; 50.68; 61.40; 73.25; 99.92; 114.44; 115.42; 115.58; 122.96; 125.52; 130.56; 131.46; 144.21; 145.25; 142.36; 153.41; 155.85; 159.15; 172.00. IR(KBr): 1266; 1512; 1581; 1618; 1751.

Example 19

7-ethyl-7-hydroxy-7,8,11,14-tetrahydro-9H,12H-[1,3]dioxolo[4,5-g]oxepino[3',4':6,7]indolizino[1,2-b]quinoline-9,12-dione This compound is obtained from 3,4-methylenedioxyaniline according to the method illustrated in Stages 11i, 11j and 11k of Example 11. Cream solid; m.p. >2500 C.

NMR-$^1$H (DMSO): 0.85 (t, 3H); 1.85 (q, 2H); 3.07 (d, 1H); 3.45 (d, 1H); 5.20 (s, 2H); 5.39 (d, 1H); 5.51 (d, 1H); 6.00 (s, 1H); 6.30 (s, 2H); 7.30 (s, 1H); 7.49 (d, 2H); 8.45 (s, 1H). NMR-$C^{13}$ (DMSO): 8.43; 36.49; 42.56; 50.58; 61.42; 73.31; 98.87; 102.75; 103.33; 104.92; 121.76; 125.74; 128.59; 130.33; 145.08; 146.69; 148.78; 150.19; 151.49; 155.90; 159.24; 172.08. IR (KBr): 1248; 1459; 1606; 1731.

Example 20

9-chloro-5-ethyl-5-hydroxy-10-methoxy-1,4,5,13-tetrahydro-3H,15H-oxepino[3',4':6,7]indolizino[1,2-b]quinoline-3,15-dione This compound is obtained from 3-chloro-4-methoxyaniline according to the method illustrated in Stages 11i, 11j and 11k of Example 11. White solid; m.p. >250° C.

NMR-¹H (DMSO): 0.85 (t, 3H); 1.85 (q, 2H); 3.07 (d, 1H); 3.45 (d, 1H); 4.01 (s, 3H); 5.22 (s, 2H); 5.39 (d, 1H); 5.51 (d, 1H); 6.02 (s, 1H); 7.31 (s, 1H); 7.68 (s, 1H); 8.20 (s, 1H); 8.55 (s, 1H). NMR-C¹³ (DMSO): 8.22; 36.27; 42.30; 50.48; 56.69; 61.23; 73.08; 99.16; 107.44; 122.16; 127.12; 128.12; 129.25; 130.02; 130.53; 143.29; 144.37; 151.12; 153.29; 155.71; 158.98; 171.84. IR (KBr): 1056; 1256; 1483; 1592; 1657; 1747.

Example 21

5-ethyl-5-hydroxy-10-methoxy-1,4,5,13-tetrahydro-3H,15H-oxepino[3',4':6,7]indolizino[1,2-b]quinoline-3,15-dione This compound is obtained from 4-methoxyaniline according to the method illustrated in Stages 11.i., 11.j. and 11.k. of Example 11. Yellow solid; m.p. >250° C.

NMR-¹H (DMSO): 0.85 (t, 3H); 1.85 (q, 2H); 3.07 (d, 1H); 3.45 (d, 1H); 3.95 (s, 3H); 5.28 (s, 2H); 5.40 (d, 1H); 5.51 (d, 1H); 6.00 (s, 1H); 7.38 (s, 1H); 7.51 (d, 2H); 8.07 (d, 1H); 8.55 (s, 1H). NMR-C¹³ (DMSO): 8.45; 36.48; 42.51; 50.64; 55.92; 61.42; 73.33; 99.01; 106.49; 122.02; 123.19; 129.59; 130.20; 130.43; 144.17; 144.94; 150.40; 155.92; 158.31; 159.26; 172.07. IR (KBr): 1251; 1604; 1655; 1735.

Example 22

9,11-dichloro-5-ethyl-5-hydroxy-1,4,5,13-tetrahydro-3H,15H-oxepino[3',4':6,7]indolizino[1,2-b]quinoline-3,15-dione This compound is obtained from 3,5-dichloroaniline according to the method illustrated in Stages 11.i., 11.j. and 11.k. of Example 11. Yellow solid; m.p. >250° C.

NMR-¹H (DMSO): 0.85 (t, 3H); 1.85 (q, 2H); 3.07 (d, 1H); 3.45 (d, 1H); 5.30 (s, 2H); 5.41 (d, 1H); 5.55 (d, 1H); 6.08 (s, 1H); 7.41 (s, 1H); 8.05 (s, 1H); 8.21 (s, 1H); 8.91 (s, 1H). NMR-C¹³ (DMSO): 8.39; 36.45; 42.51; 51.03; 61.39; 73.25; 100.62; 123.55; 124.63; 127.60; 128.08; 128.56; 132.06; 132.19; 134.53; 143.77; 148.80; 154.88; 155.82; 159.13; 171.98. IR(KBr): 1064; 1275; 1586; 1651; 1743.

Example 23

5-ethyl-9-fluoro-5-hydroxy-10-methyl-1,4,5,13-tetrahydro-3H,15H-oxepino[3',4':6,7]indolizino[1,2-b]quinoline-3,15-dione This compound is obtained from 3-fluoro-4-methylaniline according to the method illustrated in Stages 11.i., 11.j. and 11.k. of Example 11. Yellow solid; m.p. >250° C.

NMR-¹H (DMSO): 0.89 (t, 3H); 1.85 (q, 2H); 2.49 (s, 3H); 3.08 (d, 1H); 3.49 (d, 1H); 5.21 (s, 2H); 5.39 (d, 1H); 5.51 (d, 1H); 6.05 (s, 1H); 7.39 (s, 1H); 7.87 (d, 1H); 8.05 (d, 1H); 8.61 (s, 1H). NMR-C¹³ (DMSO): 8.40; 15.14; 36.45; 42.52; 50.60; 61.41; 73.28; 99.71; 112.00; 122.66; 125.38; 127.66; 129.59; 130.28; 144.49; 147.88; 152.88; 155.85; 159.18; 162.25; 172.02. IR (KBr): 1054; 1580; 1651; 1760.

Example 24

5-ethyl-10-fluoro-5-hydroxy-1,4,5,13-tetrahydro-3H,15H-oxepino[3',4':6,7]indolizino[1,2-b]quinoline-3,15-dione This compound is obtained from 4-fluoroaniline according to the method illustrated in Stages 11.i., 11.j. and 11.k. of Example 11. White solid; m.p. >250° C.

NMR-¹H (DMSO): 0.85 (t, 3H); 1.85 (q, 2H); 3.07 (d, 1H); 3.45 (d, 1H); 5.29 (s, 2H); 5.39 (d, 1H); 5.55 (d, 1H); 6.30 (s, 1H); 7.39 (s, 1H); 7.80 (q, 1H); 7.99 (q, 1H); 8.23 (q, 1H); 8.68 (s, 1H). NMR-C¹³ (DMSO): 8.40; 36.46; 42.48; 50.66; 61.41; 73.31; 99.68; 111.83; 122.75; 128.93; 130.93; 131.22; 131.93; 144.46; 145.27; 152.60; 155.89; 159.21; 172.04. IR (KBr): 1209; 1589; 1659; 1739.

Example 25

10-chloro-5-ethyl-5-hydroxy-1,4,5,13-tetrahydro-3H,15H-oxepino[3',4':6,7]indolizino[1,2-b]quinoline-3,15-dione This compound is obtained from 4-chloroaniline according to the method illustrated in Stages 11.i., 11.j. and 11.k. of Example 11. Yellow solid. m.p. >250° C.

NMR-¹H (DMSO): 0.85 (t, 3H); 1.85 (q, 2H); 3.07 (d, 1H); 3.47 (d, 1H); 5.25 (s, 2H); 5.39 (d, 1H); 5.51 (d, 1H); 6.05 (s, 1H); 7.39 (s, 1H); 7.89 (d, 1H); 8.19 (d, 1H); 8.29 (s, 1H); 8.67 (s, 1H). NMR-C¹³ (DMSO): 8.40; 36.46; 42.47; 50.70; 61.42; 73.31; 100.00; 122.96; 127.31; 127.42; 128.87; 131.11; 132.12; 144.34; 146.53; 153.38; 155.88; 159.20; 172.04. IR (KBr): 1069;1483; 1606; 1741.

Example 26

9-chloro-5-ethyl-10-fluoro-5-hydroxy-1,4,5,13-tetrahydro-3H,15H-oxepino[3',4':6,7]indolizino[1,2-b]quinoline-3,15-dione This compound is obtained from 3-chloro-4-fluoroaniline according to the method illustrated in Stages 11.i., 11.j. and 11.k. of Example 11. Yellow solid. m.p. >250° C.

NMR-¹H (DMSO): 0.85 (t, 3H); 1.85 (q, 2H); 3.07 (d, 1H); 3.45 (d, 1H); 5.25 (s, 2H); 5.39 (d, 1H); 5.51 (d, 1H); 6.05 (s, 1H); 7.40 (s, 1H); 8.20 (d, 1H); 8.40 (d, 1H); 8.68 (s, 1H). NMR-C¹³ (DMSO): 8.38; 36.47; 42.58; 50.71; 61.40; 73.26; 99.99; 113.59; 123.09; 124.28; 127.74; 130.64; 131.31; 144.13; 145.08; 153.57; 154.13; 155.84; 156.61; 159.14; 172.00. IR (KBr): 1488; 1583; 1655; 1743.

Example 27

5-ethyl-5,10-dihydroxy-11-(4-morpholinylmethyl)-1,4,5,13-tetrahydro-3H,15H-oxepino[3',4':6,7]indolizino[1,2-b]quinoline-3,15-dione This compound is obtained from morpholine according to the method illustrated in Example 15.a. White solid, m.p. >250° C.

NMR-¹H (DMSO): 0.85 (t, 3H); 1.87 (q, 2H); 2.53 (s, 4H); 3.03 (d, 1H); 3.45 (d, 1H); 3.57 (s, 4H); 4.02 (s, 2H); 5.01 (s, 2H); 5.38 (d, 1H); 5.52 (d, 1H); 6.0 (se, 1H); 7.30 (s, 1H); 7.42 (d, 1H); 7.95 (d, 1H); 8.82 (s, 1H). NMR-C¹³ (DMSO): 8.45; 3.49; 42.58; 53.04; 61.44; 66.33; 73.33; 98.81; 113.78; 121.81; 122.74; 126.80; 129.05; 129.91; 143.72; 145.07; 149.24; 155.06; 156.92; 159.28; 172.08. IR (KBr): 1515; 1595; 1654; 1736.

Example 28

5,12-diethyl-9-fluoro-5-hydroxy-10-methoxy-1,4,5,13-tetrahydro-3H,15H-oxepino[3',4':6,7]indolizino[1,2-b]quinoline-3,15-dione 28.a. 1-(2-amino-4-fluoro-5-methoxyphenyl)-1-propanone (This product is obtained according to Sugasawa T; Toyoda T; Adachi M; Sasakura K, *J. Am. Chem. Soc.*, 100

(1978), p.4842–4852). Boron trichloride (1M in heptane, 156 ml, 156 mmol) is added dropwise, under an argon atmosphere at 0° C. to a solution of 3-fluoro-4-methoxy-aniline (20 g, 142 mmol) in anhydrous dichloromethane (200 ml). The pink suspension thus obtained is maintained under agitation for 5 minutes, then propionitrile (33 ml, 420 mmol) is added dropwise followed by aluminium trichloride (20.8 g, 156 mmol) in small portions. The reaction medium is heated under reflux for 3 hours, cooled down to 0° C., hydrolyzed by cautiously adding 2N hydrochloric acid (100 ml), then heated at reflux for 45 minutes. After cooling down to 0° C. a precipitate is obtained which is filtered out, washed with dichloromethane, then taken up in water (300 ml). The aqueous phase is basified to an alkaline pH, extracted with dichloromethane then ethyl acetate. The organic phase is dried ($MgSO_4$) then evaporated to produce a crude product which is purified by column chromatography ($SiO_2$, AcOEt/Hpt: 1/99 to 20/80). 15.3 g of a yellow solid is obtained.

NMR-$^1$H (CDCl$_3$): 1.20 (t, 3H); 2.92 (q, 2H); 3.83 (s, 3H); 6.2 (s, 2H); 6.40 (d, 2H); 7.32 (d, 2H). IR (KBr): 857; 1148; 1240; 1561; 1583; 1662.

28.b. ethyl 4-ethyl-7-fluoro-6-methoxy-2-oxo-1,2-dihydro-3-quinolinecarboxylate A solution of ethylmalonyl chloride (12.9 ml, 100 mmol) in anhydrous acetonitrile (30 ml) is added dropwise, under argon and at 0° C. to a solution of 1-(2-amino-4-fluoro-5-methoxyphenyl)-1-propanone (15.3 g, 77.5 mmol) and triethylamine (13.9 ml, 100 mmol) in anhydrous acetonitrile (110 ml). The reaction medium is left to return to ambient temperature, a solution of sodium ethylate (obtained by 1.8 g, 78 mmol of sodium in 80 ml of ethanol) is cannulated dropwise and under argon, then the reaction medium is left under agitation for 12 hours at ambient temperature. The reaction mixture is poured into ice-cooled water (100 ml) and agitation is carried out for two hours, then the precipitate is filtered out and washed with water, with ethanol and with ether. 19.4 g of a white solid is obtained.

NMR-$^1$H (DMSO): 1.25 (m, 6H); 2.78 (q, 2H); 3.92 (s, 3H); 4.30 (q, 2H); 7.15 (d, 2H); 7.40 (d, 2H); 11.93 (s, 1H). IR (KBr): 786; 1083; 1410; 1521; 1644; 1725.

28.c. ethyl 2-chloro-4-ethyl-7-fluoro-6-methoxy-3-quinolinecarboxylate

A suspension of ethyl 4-ethyl-7-fluoro-6-methoxy-2-oxo-1,2-dihydro-3-quinolinecarboxylate (19 g, 0.066 mol) in phosphoryl chloride (243 ml) is heated at reflux for 6 hours. The phosphoryl chloride is distilled off. The reaction mixture is decanted into ice-cooled water, then taken up in dichloromethane to solubilize. The organic phase is washed with water, then with a saturated solution of sodium chloride. The organic phase is dried over magnesium sulphate and the solvent is evaporated off. The residue is suspended in ether and the non-converted starting product (4 g) is filtered out. The filtrate is evaporated and the residue is purified by column chromatography ($SiO_2$, AcOEt/Hpt: 5/95 to 20/80). 10.9 g of a white solid is obtained.

NMR-$^1$H (DMSO): 1.30 (t, 3H); 1.39 (t, 3H); 3.08 (q, 2H); 4.09 (s, 3H); 4.49 (q, 2H); 7.64 (d, 2H); 7.86 (d, 2H). IR (KBr): 865; 1016; 1082; 1190; 1224; 1253; 1272; 1508; 1571; 1732.

28.d. (2-chloro-4-ethyl-7-fluoro-6-methoxy-3-quinolinyl)methanol

A solution of ethyl 2-chloro-4-ethyl-7-fluoro-6-methoxy-3-quinolinecarboxylate (10.8 g, 35 mmol) in anhydrous dichloromethane (200 ml) is treated dropwise at ambient temperature under an inert atmosphere with diisobutylaluminium hydride (1M in dichloromethane, 65 ml, 65 mmol), then heated at 40° C. for 4 hours. After cooling down to 0° C., a 20% aqueous solution of Rochelle salt (105 ml) and dichloromethane (200 ml) are added cautiously and the reaction mixture is maintained under agitation for 1 hour, followed by decanting and washing three times with water. The organic phase is dried over magnesium sulphate and the solvent is evaporated off. The residue is purified by column chromatography ($SiO_2$, AcOEt/Hpt: 5/95 to 50/50). 6 g of a white solid is obtained.

NMR-$^1$H (DMSO): 1.28 (t, 3H); 3.25 (q, 2H); 4.04 (s, 3H); 4.77 (d, 2H); 5.27 (t, 1H); 7.55 (d, 2H); 7.73 (d, 2H). IR (KBr): 840; 864; 1023; 1232; 1267; 1317; 1444; 1511; 1569.

28.e. 5,12-diethyl-9-fluoro-5-hydroxy-10-methoxy-1,4,5,13-tetrahydro-3H,15H-oxepino[3',4':6,7]indolizino[1,2-b]quinoline-3,15-dione (2-chloro-4-ethyl-7-fluoro-6-methoxy-3-quinolinyl)methanol is coupled with compound (M) as described in Stage 11.j. of Example 11. The resultant coupled product is cyclized according to the procedure described in Stage 11.k. A yellow solid is obtained, m.p. >275° C.

NMR-$^1$H (CF3COOD): 1.07 (m, 3H); 1.62 (m, 3H); 2.27 (m, 2H); 3.44 (d, 1H); 3.54 (m, 2H); 3.91 (d, 1H); 4.25 (s, 3H); 5.60 (d, 1H); 5.74 (s, 2H); 5.98 (d, 1H); 7.85 (m, 1H); 8.16 (m, 1H); 8.31 (s, 1H). NMR-C$^{13}$ (CF3COOD): 9.03; 14.20; 26.68; 38.77; 43.98; 53.79; 58.27; 64.73; 77.93; 106.85; 109.24; 110.15; 128.99; 129.20; 131.61; 137.32; 141.23; 144.13; 154.79; 158.32; 160.25; 160.81; 179.30. IR (KBr): 1013; 1068; 1265; 1466; 1514; 1601; 1655; 1748.

Example 29

5-ethyl-5-hydroxy-12-methyl-1,4,5,13-tetrahydro-3H,15H-oxepino[3',4':6,7]indolizino[1,2-b]quinoline-3,15-dione The procedure described in Examples 28.b., 28.c. and 28.d. is applied to 2-acetylaniline in order to produce (2-chloro-4-methyl-3-quinolinyl)methanol. The latter coupled to compound (M) as described in Stage 11.j. of Example 11. The resultant coupled product is cyclized according to the procedure of Stage 11.k. A yellow solid is obtained, m.p. >260° C.

NMR $^1$H (DMSO): 0.87 (t, 3H); 1.87 (q, 2H); 2.78 (s, 3H); 2.80 (d, 1H); 3.55 (d, 1H); 5.27 (s, 2H); 5.42 (d, 1H); 5.52 (d, 1H); 6.04 (s, 1H); 7.39 (s, 1H); 7.75 (t, 1H); 7.88 (t, 1H); 8.13 (d, 1H); 8.25 (d, 1H). NMR-C$^{13}$ (DMSO): 8.23; 36.26; 42.36; 62.00; 73.11; 78.65; 79.13; 79.25; 99.52; 122.36; 124.30; 127.67; 129.54; 129.55; 129.56; 140.11; 145.06; 148.07; 152.00; 155.79; 159.09; 171.89. IR (KBr): 1649; 1751; 3404.

Example 30

9-chloro-5-ethyl-5-hydroxy-10-methoxy-12-[(4-methyl-1-piperazinyl)methyl]-1,4,5,13-tetrahydro-3H,15H-oxepino[3',4':6,7]indolizino[1,2-b]quinoline-3,15-dione 30.a. 5-chloro-2-chloroacetyl-4-metboxyaniline This product is obtained according to Sugasawa T; Toyoda T; Adachi M; Sasakura K, *J. Am. Chem. Soc.*, 100 (1978), p.4842–4852. A molar solution of boron trichloride in hexane (164 ml, 164 mmol), chloroacetonitrile (11,4 ml, 180 mmol), and a molar solution of diethylaluminium chloride in hexane (164 ml, 164 mmol). are added dropwise and successively under an inert atmosphere at 0° C. to a solution of 3-chloro-4-methoxyaniline (23.6 g, 150 mmol). The reaction medium is heated under reflux for 1 hour, cooled down to 0° C., hydrolyzed by cautiously adding 2N hydrochloric acid (90 ml), then beating to reflux for 1 hour. The reaction medium is cooled down and a concentrated soda solution is added until pH 14. Extraction is carried out with ethyl acetate, the organic phase is washed with water, then with salt water. Followed by drying over magnesium sulphate, filtering and evaporating under reduced pressure. The residue is taken up in isopentane, followed by decanting, then the insoluble part is taken up in the minimum amount of isopropyl ether, isopentane is added in order to precipitate the product, followed by filtering and drying under vacuum. 17.26 g of a brown solid is obtained.

NMR-$^1$H (CDCl$_3$): 3.82 (s, 3H); 4.60 (s, 2H); 6.11 (s, 2H); 6.78 (s, 1H); 7.11 (s, 1H).

30.b. ethyl 7-chloro-4-(chloromethyl)-6-methoxy-2-oxo-1,2-dihydro-3-quinolinecarboxylate A solution of ethylmalonyl chloride (17 ml, 131 mmol) is added dropwise under argon and at 0° C. to a solution of 5-chloro-2-chloroacetyl-4-methoxyaniline (17 g, 73 mmol) and triethylamine (18.5 ml, 131 mmol) in anhydrous acetonitrile (310 ml). Agitation is carried out for 2 hours at ambient temperature, then a solution of sodium ethanolate in ethanol (obtained by 1.88 g, 80 mmol, of sodium in 90 ml of ethanol) is added dropwise at 0° C. Agitation is carried out for 12 hours at ambient temperature. 300 ml of water is added, and agitation is again carried out for 20 minutes. The precipitate is filtered out; washed with water, with ethanol, and with ethyl ether. After drying under vacuum 16.7 g of a yellowish solid is obtained.

NMR-$^1$H (DMSO): 1.31 (t, 3H); 3.95 (s, 3H); 4.36 (q, 2H); 4.95 (s, 2H); 7.46 (s, 1H); 7.49 (s, 1H).

30.c. ethyl 2,7-dichloro-4-(chloromethyl)-6-methoxy-3-quinolinecarboxylate

A suspension of ethyl 7-chloro-4-(chloromethyl)-6-methoxy-2-oxo-1,2-dihydro-3-quinolinecarboxylate (116.7 g, 50 mmol) in phosphoryl chloride (100 ml) is heated to reflux for 6 hours. The phosphoryl chloride is distilled off. The residue is taken up in water and agitation is carried out for 30 min. The precipitate is filtered out and washed with water until neutrality. The precipitate is taken up in dichloromethane and with a saturated solution of sodium chloride. After filtering through a bed of celite the filtrate is decanted. The organic phase is washed again with a saturated solution of sodium chloride, followed by drying over magnesium sulphate, filtering and evaporating under reduced pressure. 15.88 g of a brown oil is obtained.

NMR-$^1$H (CDCl$_3$): 1.47 (t, 3H); 4.08 (t, 3H); 4.55 (q, 2H); 4.87 (s, 2H); 7.35 (s, 1H); 8.09 (s, 1H).

30.d. ethyl 2,7-dichloro-6-methoxy-4-[(4-methyl-1-piperazinyl)methyl]-3-quinolinecarboxylate A mixture of ethyl 2,7-dichloro-4-(chloromethyl)-6-methoxy-3-quinolinecarboxylate (6.9 g, 20 mmol) and N-methylpiperazine (9 ml, 80 mmol) is heated to 60° C. for 30 min. The reaction mass is diluted with water and extraction is carried out with ethyl acetate. After decanting, the organic phase is washed with water, followed by drying over magnesium sulphate, filtering and evaporating under reduced pressure. The residue is taken up in water, agitated for 15 minutes, filtered, washed with water and dried under vacuum. The residue is purified by column chromatography (SiO$_2$, MeOH/CH$_2$Cl$_2$: 5/95 to 8/92). 6.7 g of product, a beige solid, is obtained.

NMR-$^1$H (CDCl$_3$): 1.45 (t, 3H); 2.28 (s, 3H); 2.35–2.70 (m, 8H); 3.86 (s, 2H); 4.04 (s, 3H); 4.48 (q, 2H); 7.77 (s, 1H); 8.05 (s, 1H).

30.e. {2,7-dichloro-6-methoxy-4-[(4-methyl-1-piperazinyl)methyl]-3-quinolinyl}methanol ethyl 2,7-dichloro-6-methoxy+[(4-methyl-1-piperazinyl)methyl]-3-quinolinecarboxylate (6 g, 14.5 mmol) is dissolved in methylene chloride (120 ml). A molar solution of diisobutylaluminium hydride in methylene chloride (60 ml, 60 mmol) is added slowly. Agitation is carried out for one hour at ambient temperature. The reaction mass is slowly poured into 300 ml of a 20% solution of Rochelle salt. Agitation is carried out for one hour, followed by filtering on celite and decanting; the organic phase is washed with a saturated solution of sodium chloride, dried over magnesium sulphate, filtered and evaporated under reduced pressure. The solid is taken up in isopropyl ether, filtered and dried under vacuum. 4.3 g of sought product (80%) is obtained, in the form of a yellow solid.

NMR-$^1$H (CDCl$_3$): 2.27 (s, 3H); 2.30–2.80 (m, 8H); 4.03 (s, 3H); 4.08 (s, 2H); 4.96 (s, 2H); 5.95 (s, 1H); 7.37 (s, 1H); 8.05 (s, 1H).

30.f. 9-chloro-5-ethyl-5-hydroxy-10-methoxy-12-[(4-methyl-1-piperazinyl)methyl]-1,4,5,13-tetrahydro-3H,15H-oxepino[3',4':6,7]indolizino[1,2-b]quinoline-3,15-dione {2,7-dichloro-6-methoxy-4-[(4-methyl-1-piperazinyl)methyl]-3-quinolinyl}-methanol is coupled to compound (M) as described in Stage 11.j. of Example 11. The resultant coupled product is cyclized according to the procedure of Stage 11.k. A yellow solid is obtained, m.p. >250° C.

NMR-$^1$H (DMSO): 0.87 (t, 3H); 1.84 (q, 2H); 2.53 (s, 4H); 3.08 (d, 1H); 3.47 (d, 1H); 3.58 (s, 4H); 4.06 (s, 5H); 5.30 (s, 2H); 5.42 (q, 2H); 6.03 (s, 1H); 7.31 (s, 1H); 7.91 (s, 1H); 8.16 (s, 1H). NMR-C$^{13}$ (DMSO): 8.42; 36.53; 50.65; 53.30; 56.67; 62.00; 66.50; 73.32; 99.31; 104.86; 122.32; 126.94; 127.70; 129.83; 130.44; 138.89; 144.22; 144.85; 151.05; 153.17; 155.92; 159.19; 172.06. IR (KBr): 862; 1063; 1116; 1248; 1595; 1655; 1744; 3449.

Example 31

9-chloro-5-ethyl-5-hydroxy-10-methoxy-12-(4-morpholinylmethyl)-1,4,5,13-tetrahydro-3H,15H-oxepino[3',4':6,7]indolizino[1,2-b]quinoline-3,15-dione The procedure described in Examples 30.a., 30.b. and 30.c. is applied to 3-chloro-4-methoxyaniline in order to produce ethyl 2,7-dichloro-4-chloromethyl-6-methoxy-3-quinoline-carboxylate which is treated according to the procedure of Example 30.d., by using morpholine instead of N-methylpiperazine, then reduced according to the method of Example 30.e. into the corresponding quinolinemethanol. The latter is coupled to compound (M) as described in Stage 11.j. of Example 11. The resultant coupled product is cyclized according to the procedure of Stage 11.k. A beige solid is obtained, m.p. >250° C.

NMR-¹H (DMSO): 0.87 (t, 3H); 1.84 (q, 2H); 2.15 (s, 3H); 2.32 (s, 4H); 2.50 (s, 4H); 3.08 (d, 1H); 3.47 (d, 1H); 4.06 (s, 5H); 5.29 (s, 2H); 5.46 (q, 2H); 6.06 (s, 1H); 7.31 (s, 1H); 7.92 (s, 1H); 8.17 (s, 1H). NMR-C¹³ (DMSO): 8.42; 36.51; 42.57; 45.93; 50.66; 52.83; 55.05; 56.09; 56.72; 61.44; 73.29; 99.30; 104.89; 122.32; 126.89; 127.63; 129.85; 130.16; 138.78; 144.18; 144.81; 151.03; 153.10; 155.10; 159.17; 172.07. IR (KBr): 1055; 1252; 1596; 1655; 1747; 3449.

Example 32

5-ethyl-5-hydroxy-12-[(4-methyl-1-piperazinyl)methyl]-1,4,5,13-tetrahydro-3H,15H-oxepino[3',4':6,7]indolizino[1,2-b]quinoline-3,15-dione The procedure described in Examples 30.a., 30.b. and 30.c. is applied to aniline in order to produce ethyl 2-chloro-4-chloromethyl-3-quinolinecarboxylate which is treated according to the procedure of Example 30.d., with N-methylpiperazine, then reduced according to the method of Example 30.e. into the corresponding quinolinemethanol. The latter is coupled to compound (M) as described in Stage 11.j. of Example 11. The resultant coupled product is cyclized according to the procedure of Stage 11.k. A yellow solid is obtained, m.p. >260° C.

NMR-¹H (DMSO): 0.86 (t, 3H); 1.87 (q, 2H); 2.14 (s, 3H); 2.32–2.60 (m, 8H); 3.05 (d, 1H); 3.48 (d, 1H); 4.09 (q, 2H); 5.42 (d, 1H); 5.52 (d, 1H); 6.03 (se, 1H); 7.40 (s, 1H); 7.72 (t, 1H); 7.85 (t, 1H); 8.16 (d, 1H); 8.45 (d, 1H). IR (KBr): 1652; 1735; 3424.

Example 33

5-ethyl-5-hydroxy-12-(1-piperidinylmethyl)-1,4,5,13-tetrahydro-3H,15H-oxepino[3',4':6,7]indolizino[1,2-b]quinoline-3,15-dione The procedure described in Examples 30.a., 30.b. and 30.c. is applied to aniline in order to produce ethyl 2-chloro-4-chloromethyl-3-quinoline carboxylate which is treated according to the procedure of Example 30.d., by using piperidine instead of N-methylpiperazine, then reduced according to the method of Example 30.e. into the corresponding quinolinemethanol. The latter is coupled to compound (M) as described in Stage 11.j. of Example 11. The resultant coupled product is cyclized according to the procedure of Stage 11.k. A yellow solid is obtained, m.p. >260° C.

NMR-¹H (DMSO): 0.86 (t, 3H); 1.40 (se, 2H); 1.48 (se, 4H); 1.87 (q, 2H); 2.50 (s, 4H); 3.05 (d, 1H); 3.48 (d, 1H); 4.04 (q, 2H); 5.33 (s, 2H); 5.42 (d, 1H); 5.51 (d, 1H); 6.07 (se, 1H); 7.75 (t, 1H); 7.85 (t, 1H); 8.15 (d, 1H); 8.45 (d, 1H). NMR-C¹³ (DMSO): 8.47; 23.50; 25.82; 36.50; 42.50; 50.68; 54.47; 58.00; 61.42; 73.35; 99.55; 122.61; 125.31; 127.58; 129.54; 129.55; 129.56; 129.57; 140.49; 144.95; 148.63; 152.41; 155.90; 159.23; 172.07. IR (KBr): 1659; 1727; 3408.

Example 34

5-ethyl-5-hydroxy-12-(4-morpholinylmethyl)-1,4,5,13-tetrahydro-3H,15H-oxepino[3',4':6,7]indolizino[1,2-b]quinoline-3,15-dione The procedure described in Examples 30.a., 30.b. and 30.c. is applied to aniline in order to produce ethyl 2-chloro-4-chloromethyl-3-quinolinecarboxylate which is treated according to the procedure of Example 30.d., by using morpholine instead of N-methylpiperazine, then reduced according to the method of Example 30.e. into the corresponding quinolinemethanol. The latter is coupled to compound (M) as described in Stage 11.j. of Example 11. The resultant coupled product is cyclized according to the procedure of Stage 11.k. A yellow solid is obtained, m.p. >260° C.

NMR-¹H (DMSO): 0.86 (t, 3H); 1.87 (q, 2H); 3.05 (d, 1H); 3.30 (s, 4H); 3.49 (d, 1H); 3.55 (se, 4H); 4.10 (q, 2H); 5.35 (s, 2H); 5.40 (d, 1H); 5.54 (d, 1H); 6.04 (s, 1H); 7.72 (t, 1H); 7.85 (t, 1H); 8.16 (d, 1H); 8.47 (d, 1H). NMR-C¹³ (DMSO): 8.42; 36.51; 42.57; 50.68; 53.51; 56.06; 61.42; 66.41; 73.34; 99.56; 122.64; 125.25; 127.56; 129.81; 139.55; 144.92; 148.62; 152.39; 155.89; 159.21; 172.05. IR (KBr): 1657; 1729; 3347.

Example 35

5-ethyl-10-fluoro-5-hydroxy-12-[(4-methyl-1-piperazinyl)methyl]-1,4,5,13-tetrahydro-3H,15H-oxepino[3',4':6,7]indolizino[1,2-b]quinoline-3,15-dione The procedure described in Examples 30.a., 30.b. and 30.c. is applied to 4-fluoroaniline in order to produce ethyl 2-chloro-4-chloromethyl-6-fluoro-3-quinolinecarboxylate which is treated according to the procedure of Example 30.d. with N-methylpiperazine, then reduced according to the method of Example 30.e. into the corresponding quinolinemethanol. The latter is coupled to compound (M) as described in Stage 11.j. of Example 11. The resultant coupled product is cyclized according to the procedure of Stage 11.k. A yellow solid is obtained, m.p. >275° C.

NMR-¹H (DMSO): 0.87 (t, 3H); 1.85 (q, 2H); 2.15 (s, 3H); 2.31 (m, 4H); 2.50 (m, 4H); 3.07 (d, 1H); 3.48 (d, 1H); 4.04 (m, 2H); 5.31 (s, 2H); 5.40 (d, 1H); 5.53 (d, 1H); 6.05 (s, 1H); 7.38 (s, 1H); 7.77 (m, 1H); 8.19 (m, 2H). NMR-C¹³ (DMSO): 8.43; 36.51; 42.54; 45.89; 50.67; 52.92; 54.93; 55.92; 73.32; 99.56; 122.69; 130.43; 132.40; 139.69; 144.70; 145.84; 152.19; 155.90; 159.17; 172.05. IR (KBr): 836; 1051; 1217; 1291; 1612; 1662; 1726.

Example 36

5-ethyl-10-fluoro-5-hydroxy-12-(4-morpholinylmethyl)-1,4,5,13-tetrahydro-3H,15H-oxepino[3',4':6,7]indolizino[1,2-b]quinoline-3,15-dione The procedure described in Examples 30.a., 30.b. and 30.c. is applied to 4-fluoroaniline in order to produce ethyl 2-chloro-4-chloromethyl-6-fluoro-3-quinolinecarboxylate which is treated according to the procedure of Example 30.d., by using morpholine instead of N-methylpiperazine, then reduced according to the method of Example 30.e. into the corresponding quinolinemethanol. The latter is coupled to compound (M) as described in Stage 11.j. of Example 11. The resultant coupled product is cyclized according to the procedure of Stage 11.k. A beige solid is obtained, m.p. >2500 C.

NMR-¹H (DMSO): 0.87 (m, 3H); 1.85 (m, 2H); 2.51 (m, 4H); 3.06 (d, 1H); 3.48 (d, 1H); 3.56 (m, 4H); 4.05 (m, 2H); 5.34 (s, 2H); 5.40 (d, 1H); 5.53 (d, 1H); 6.04 (s, 1H); 7.38 (s, 1H); 7.77 (m, 1H); 8.21 (m, 2H). NMR-C¹³ (DMSO): 8.40; 36.47; 42.52; 50.59; 53.40; 56.14; 61.44; 66.41; 73.29; 99.58; 109.05; 109.28; 120.11; 120.37; 122.68; 128.53; 130.53; 132.43; 139.13; 144.62; 145.79; 152.07; 155.94; 159.14; 161.59; 172.04. IR (KBr): 834; 860; 1061; 1118; 1215; 1286; 1516; 1609; 1658; 1734.

Example 37

5-ethyl-9-fluoro-5-hydroxy-10-methyl-12-[(4-methyl-1-piperazinyl)methyl]-1,4,5,13-tetrahydro-3H,15H-oxepino[3',4':6,7]indolizino[1,2-b]quinoline-3,15-dione The procedure described in Examples 30.a., 30.b. and 30.c. is applied to 3-fluoro-4-methylaniline in order to produce ethyl 2-chloro-4-chloromethyl-7-fluoro-6-methyl-3-quinolinecarboxylate which is treated according to the procedure of Example 30.d. with N-methylpiperazine, then reduced according to the method of Example 30.e. into the corresponding quinolinemethanol. The latter is coupled to compound (M) as described in Stage 11.j. of Example 11. The resultant coupled product is cyclized according to the procedure of Stage 11.k. A yellow solid is obtained, m.p. >260° C.

NMR-$^1$H (CDCl$_3$): 1.00 (t, 3H); 2.00 (q, 2H); 2.35 (s, 3H); 2.50 (s, 3H); 2.61 (m, 8H); 3.33 (d, 1H); 3.39 (d, 1H); 3.97 (d, 1H); 4.07 (d, 1H); 5.17 (d, 1H); 5.38 (d, 1H); 5.52 (d, 1H); 5.63 (d, 1H); 7.13 (d, 1H); 7.28 (s, 1H); 7.99 (d, 1H). IR (KBr): 1652; 1747; 3430.

Example 38

5-ethyl-9-fluoro-5-hydroxy-10-methyl-12-(4-morpholinylmethyl)-1,4,5,13-tetrahydro-3H,15H-oxepino[3',4':6,7]indolizino[1,2-b]quinoline-3,15-dione The procedure described in Examples 30.a., 30.b. and 30.c. is applied to 3-fluoro-4-methylaniline in order to produce ethyl 2-chloro-4-chloromethyl-7-fluoro-6-methyl-3-quinolinecarboxylate which is treated according to the procedure of Example 30.d., by using morpholine instead of N-methylpiperazine, then reduced according to the method of Example 30.e. into the corresponding quinolinemethanol. The latter is coupled to compound (M) as described in Stage 11.j. of Example 11. The resultant coupled product is cyclized according to the procedure of Stage 11.k. A yellow solid is obtained, m.p. >260° C.

NMR-$^1$H (DMSO+CDCl$_3$): 1.00 (t, 3H); 2.02 (q, 2H); 2.57 (s, 3H); 2.60 (s, 4H); 3.23 (d, 1H); 3.45 (d, 1H); 3.75 (s, 4H); 4.11 (s, 2H); 5.44 (s, 2H); 5.47 (d, 1H); 5.65 (d, 1H); 7.62 (s, 1H); 7.73 (d, 1H); 8.24 (d, 1H). NMR-C$^{13}$ (CF$_3$CO$_2$D): 8.35; 13.93; 16.01; 22.24; 25.29; 38.18; 43.42; 54.19; 56.04; 56.74; 64.16; 65.09; 77.48; 108.29; 108.57; 128.07; 128.70; 129.90; 135.64; 138.03; 139.86; 141.10; 141.56; 147.78; 158.30; 161.87; 178.72. IR (KBr): 117; 1609; 1654; 1750; 3437.

Example 39

5-ethyl-9-fluoro-5-hydroxy-10-methyl-12-(1-piperidinylmethyl)-1,4,5,13-tetrahydro-3H,15H-oxepino[3',4':6,7]indolizino[1,2-b]quinoline-3,15-dione The procedure described in Examples 30.a., 30.b. and 30.c. is applied to 3-fluoro-4-methylaniline in order to produce ethyl 2-chloro-4-chloromethyl-7-fluoro-6-methyl-3-quinolinecarboxylate which is treated according to the procedure of Example 30.d., by using piperidine instead of N-methylpiperazine, then reduced according to the method of Example 30.e. into the corresponding quinolinemethanol. The latter is coupled to compound (M) as described in Stage 11.j. of Example 11. The resultant coupled product is cyclized according to the procedure of Stage 11.k. A yellow solid is obtained, m.p. >260° C.

NMR-$^1$H (CF$_3$CO$_2$D): 1.09 (s, 3H); 1.70 (t, 1H); 2.03 (m, 5H); 2.25 (s, 2H); 2.70 (s, 3H); 3.54 (d, 3H); 3.88 (d, 1H); 4.01 (se, 2H); 5.30 (q, 2H); 5.65 (d, 1H); 5.96 (d, 1H); 6.10 (s, 2H); 8.16 (d, 1H); 8.35 (s, 1H); 8.61 (s, 1H). NMR-C$^{13}$ (CF$_3$CO$_2$D): 8.47; 16.07; 20.93; 22.18; 24.76; 38.28; 43.53; 54.30; 56.12; 58.33; 64.24; 77.56; 108.37; 111.30; 128.20; 129.02; 129.98; 135.60; 138.29; 139.90; 141.60; 142.26; 147.57; 158.28; 161.90; 167.63; 170.31; 178.82. IR (KBr): 1605; 1657; 1728; 3399.

Example 40

8-ethyl-8-hydroxy-16-[(4-methyl-1-piperazinyl)methyl]-2,3,8,9,12,15-hexahydro-10H,13H-[1,4]dioxino[2,3-g]oxepino[3',4':6,7]indolizino[1,2-b]quinoline-10,13-dione The procedure described in Examples 30.a., 30.b. and 30.c. is applied to 3,4-ethylenedioxyaniline in order to produce ethyl 2-chloro-4-chloromethyl-6,7-ethylenedioxy-3-quinolinecarboxylate which is treated according to the procedure of Example 30.d. with N-methylpiperazine, then reduced according to the method of Example 30.e. into the corresponding quinolinemethanol. The latter is coupled to compound (M) as described in Stage 11.j. of Example 11. The resultant coupled product is cyclized according to the procedure of Stage 11.k. A yellow solid is obtained, m.p. >260° C.

NMR-$^1$H (DMSO): 0.92 (t, 3H); 1.89 (q, 2H); 2.16 (s, 3H); 2.50 (m, 8H); 3.12 (d, 1H); 3.50 (d, 1H); 3.95 (s, 2H); 4.47 (s, 4H); 5.19 (q, 2H); 5.43 (d, 1H); 5.56 (d, 1H); 7.35 (s, 1H); 7.54 (s, 1H); 7.76 (s, 1H). NMR-C$^{13}$ (DMSO): 8.45; 24.80; 36.51; 42.48; 45.90; 50.45; 52.98; 54.91; 56.10; 61.44; 64.43; 73.30; 99.03; 109.46; 113.51; 121.95; 123.51; 127.76; 137.99; 145.00; 145.14; 145.27; 147.24; 150.53; 155.99; 159.18; 172.27; 177.00. IR (KBr): 1656; 1743; 3422.

Example 41

9-chloro-5-ethyl-10-fluoro-5-hydroxy-12-(4-morpholinylmethyl)-1,4,5,13-tetrahydro-3H,15H-oxepino[3',4':6,7]indolizino[1,2-b]quinoline-3,15-dione The procedure described in Examples 30.a., 30.b. and 30.c. is applied to 3-chloro-4-fluoroaniline in order to produce ethyl 2,7-dichloro-4-chloromethyl-6-fluoro-3-quinolinecarboxylate which is treated according to the procedure of Example 30.d., by using morpholine instead of N-methylpiperazine, then reduced according to the method of Example 30.e. into the corresponding quinolinemethanol. The latter is coupled to compound (M) as described in Stage 11.j. of Example 11. The resultant coupled product is cyclized according to the procedure of Stage 11.k. A beige solid is obtained, m.p. >250° C.

NMR-$^1$H (CF$_3$COOD): 1.09 (t, 3H); 2.30 (m, 2H); 3.50 (d, 1H); 3.90 (d, 1H); 3.98 (d, 4H); 4.36 (s, 4H); 5.38 (q, 2H); 5.64 (d, 1H); 5.96 (d, 1H); 6.23 (q, 2H); 8.57 (d, 1H); 8.60 (s, 1H); 8.85 (d, 1H). NMR-C$^{13}$ (CF$_3$COOD): 8.10; 37.80; 43.11; 54.31; 55.78; 63.75; 65.11; 77.06; 128.28; 129.55; 130.33; 136.26; 137.11; 138.40; 139.67; 139.85; 148.58; 157.54; 159.74; 161.31; 178.00. IR (KBr): 848; 1042; 1230; 1609; 1658; 1750; 3310; 3387.

Example 42

Resolution of 5-ethyl-5-hydroxy-1,4,5,13-tetrahydro-3H,15H-oxepino[3',4':6,7]indolizino[1,2-b]quinoline-3,15-dione A mixture of 3-hydroxy-3-[8-(hydroxymethyl)-9-oxo-9,11-dihydroindolizino[1,2-b]quinolin-7-yl]pentanoic acid (19.5 g, 51 mmol) and L-(−)-α-methylbenzylamine (12.12 g, 100 mmol) in absolute ethanol (1 l) is heated to boiling, followed by filtering while warm and leaving at rest for 68 hours. The precipitate is filtered and washed with ethanol and with ether to produce 9.8 g of a white solid. Analysis by high pressure liquid chromatography on the chiral stationary phase ("Chiral HPLC" on Chiral-AGP column (Chromtech, Stockholm, Sweden) 100×4 mm, eluant 2% acetonitrile in 10 mM phosphate buffer at pH 6.9, peaks eluting at 4.5 and 7.5 min) reveals two peaks integrating respectively 24% and 76% of the total area of the two peaks. The solid is taken up in 93% ethanol (350 ml) under reflux, then left at rest for 48 hours. The precipitate is filtered out then washed with ethanol and with ether in order to obtain 4.8 g of a white solid which produces two peaks integrating respectively 9% and 91% of the total area of the two peaks using chiral HPLC. The solid is taken up in 50% ethanol (48 ml) under reflux then left at rest for 48 hours. The precipitate is filtered out then washed with ethanol and with ether in order to produce 2.7 g of a white solid which produces two peaks integrating respectively 3% and 97% of the total area of the two peaks using chiral HPLC. The solid is taken up in 50% ethanol (22 ml) under reflux then left at rest for 48 hours. The precipitate is filtered out then washed with ethanol and with ether in order to produce 1.6 g of a white solid which produces two peaks integrating respectively 1% and 99% of the total area of the two peaks using chiral HPLC. The resultant salt, diastereoisomerically enriched, taken up in distilled water (20 ml), is treated with acetic acid (0.35 ml, 6.4 mmol) for 15 minutes. The precipitate obtained is filtered out, washed with water, with acetone and with ether, then dried under vacuum at 80° C. in order to obtain 1.1 g of a white solid. The latter is taken up in absolute ethanol (55 ml) with concentrated hydrochloric acid (11.5 N, 11 ml) added to it in order to obtain a yellow solution which is maintained under agitation at ambient temperature for 68 hours. The precipitate thus obtained is filtered out and washed with water, with ethanol and with ether, then dried under vacuum at 80° C. in order to obtain 770 mg of 5-ethyl-5-hydroxy-1,4,5,13-tetrahydro-3H,15H-oxepino[3',4':6,7]indolizino[1,2-b]quinoline-3,15-dione which is enantiomerically enriched. Analysis by chiral HPLC (Chiral-AGP column, eluted with a 2 to 5% gradient of acetonitrile in 10 mM phosphate buffer at pH 6.9, peaks eluting at 15 and 20 minutes) reveals an enantiomeric excess of 98%. The procedure described above is carried out again replacing the L-(−)-α-methylbenzylamine with D-(+)-α-methylbenzylamine. In this way the other enantiomer of 5-ethyl-5-hydroxy-1,4,5,13-tetrahydro-3H,15H-oxepino[3',4':6,7]indolizino[1,2-b]quinoline-3,15-dione is obtained.

Example 43

12-[3,6-dihydro-1(2H)-pyridinylmethyl]-5-ethyl-9,10-difluoro-5-hydroxy-1,4,5,13-tetrahydro-3H,15H-oxepino[3',4':6,7]indolizino[1,2-b]quinoline-3,15-dione The procedure described in Examples 30.a., 30.b. and 30.c. is applied to 3,4-difluoroaniline in order to produce ethyl 2-chloro4-chloromethyl-6,7-difluoro-3-quinoline carboxylate, which is treated according to the procedure of Example 30.d., using 1,2,3,6-tetrahydropyridine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. The free base thus obtained is suspended in absolute ethanol (50 ml/mmol) then treated with ethanolic hydrogen chloride (2.5N, 5 equ.). Initially a yellow solution forms, then a precipitate which is collected by filtering after concentration to 40% of initial volume, and washed with ether. A light orange solid is obtained, m.p. 264° C.

NMR-1H (DMSO): 0.87 (t, 3H); 1.85 (q, 2H); 2.26–2.30 (m, 1H); 2.50 (m, 1H); 3.09 (d, 1H); 3.40 (m, 2H); 3.48 (d, 1H); 3.87 (m, 2H); 5.05 (m, 2H); 5.48 (q, 2H); 5.65 (m, 2H); 5.89 (m, 1H); 7.42 (s, 1H); 8.24–8.30 (m, 1H); 8.76–8.82 (m, 1H); 10.86 (s, 1H). NMR-C13 (DMSO): 8.44; 22.36; 36.5; 42.7; 48.71; 50.30; 51.49; 61.42; 73.23; 100.16; 112.64; 112.83; 116.05; 120.26; 123.31; 125.29; 125.40; 131.17; 133.97; 144.15; 146.26; 146.37; 148.74; 150.52; 151.23; 153.20; 153.53; 155.99; 159.04; 172.02. IR (KBr): 662; 1064; 1268; 1452; 1523; 1598; 1652; 1743; 2936; 3027; 3418.

Example 44

5-ethyl-9,10-difluoro-5-hydroxy-12-[(4-methyl-1-piperidinyl)methyl]-1,4,5,13-tetrahydro-3H,15H-oxepino[3',4':6,7]indolizino[1,2-b]quinoline-3,15-dione hydrochloride The procedure described in Examples 30.a., 30.b. and 30.c. is applied to 3,4-difluoroaniline in order to produce ethyl 2-chloro-4-chloromethyl-6,7-difluoro-3-quinolinecarboxylate which is treated according to the procedure of Example 30.d., using 4-methylpiperidine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A beige solid is obtained, m.p. >250° C.

NMR-1H (DMSO): 0.9 (m, 6H); 1.1 (m, 2H); 1.4 (m, 1H); 1.55 (d, 2H); 1.85 (q, 2H); 2.1 (t, 2H); 2.85 (m, 2H); 3.25 (dd, 2H); 4 (s, 2H); 5.3 (s, 2H); 5.45 (dd, 2H); 6.05 (s, 1H); 7.35 (s, 1H); 8.15 (dd, 1H); 8.45 (dd, 1H). IR (KBr): 1454; 1518; 1608; 1658; 1733; 2804; 2926; 3311.

Suspension of the above free base in absolute ethanol (50 ml/mmol) followed by treatment with ethanolic hydrogen chloride (2.5 N, 5 equ.) allows the corresponding hydrochloride to be obtained. Initially, a yellow solution forms, then a precipitate which is collected by filtering after concentration to 40% of the initial volume, then washed with ether. A vivid orange solid is obtained, m.p. >250° C.

NMR-1H (DMSO): 0.85 (m, 6H); 1.7 (m, 5H); 1.85 (q, 2H); 3.15 (s, 1H); 3.25 (dd, 2H); 3.3 (m, 2H); 4.9 (s, 2H); 5.45 (dd, 2H); 5.6 (s, 2H); 6.1 (s, 1H); 7.4 (s, 1H); 8.25 (dd, 1H); 8.75 (dd, 1H); 10.35 (s, 1H). IR (KBr): 1270; 1455; 1523; 1606; 1653; 1742; 2943; 3419.

Example 45

5-ethyl-9,10-difluoro-5-hydroxy-12-(1-pyrrolidinylmethyl)-1,4,5,13-tetrahydro-3H,15H-oxepino[3',4':6,7]indolizino[1,2-b]quinoline-3,15-dione hydrochloride The procedure described in Examples 30.a., 30.b. and 30.c. is applied to 3,4-difluoroaniline in order to produce ethyl 2-chloro-4-chloromethyl-6,7-difluoro-3-quinolinecarboxylate which is treated according to the procedure of Example 30.d., using pyrrolidine instead of N-methylpiperazine, then reduced according to the method of Example 30.e. into the corresponding quinolinemethanol.

The latter is coupled with compound (M) as described in Stage 11.j. of Example 11. The resultant coupled product is cyclized according to the procedure of Stage 11.k. A beige solid is obtained, m.p. >250° C.

NMR-1H (DMSO): 0.85 (t, 3H); 1.7 (s, 4H); 1.85 (q, 2H); 2,55 (s, 4H); 3.25 (dd, 2H); 4.15 (d, 2H); 5.35 (s, 2H); 5.45 (dd, 2H); 6.05 (s, 1H); 7.35 (s, 1H); 8.15 (dd, 1H); 8.45 (dd, 1H). IR (KBr): 1455; 1518; 1605; 1657; 1731; 2801; 2970; 3422.

Suspension of the above free base in absolute ethanol (50 ml/mmol) followed by treatment with ethanolic hydrogen chloride (2.5 N, 5 equ.) allows the corresponding hydrochloride to be obtained. Initially, a yellow solution forms, then a precipitate which is collected by filtering after concentration to 40% of the initial volume, then washed with ether. A light orange solid is obtained, m.p. >250° C.

NMR-1H (DMSO): 0.85 (t, 3H); 1.9 (m, 4H); 2.1 (s, 2H); 3.25 (dd, 2H); 3.3 (m, 2H); 3.55 (m, 2H); 5.05 (s, 2H); 5.45 (dd, 2H); 5.6 (s, 2H); 6.1 (s, 1H); 7.4 (s, 1H); 8.3 (dd, 1H); 8.75 (dd, 1H); 10.75 (s, 1H). IR (KBr): 1454; 1522; 1603; 1653; 1743; 2970; 3394.

Example 46

5-ethyl-9,10-difluoro-5-hydroxy-12-[(4-methyl-1-piperazinyl)methyl]-1,4,5,13-tetrahydro-3H,15H-oxepino[3',4':6,7]indolizino[1,2-b]quinoline-3,15-dione The procedure described in Examples 30.a., 30.b. and 30.c. is applied to 3,4-difluoroaniline in order to produce ethyl 2-chloro-4-chloromethyl-6,7-difluoro-3-quinolinecarboxylate which is treated according to the procedure of Example 30.d., then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A yellow solid is obtained, m.p. >250° C.

NMR-1H (CDCl$_3$+CD$_3$OD): b 0.99(t, 3H); 2.00 (q, 2H); 2.32 (s, 3H); 3.24 (d, 1H); 3.37 (s, 1H); 3.42 (d, 1H); 4.04 (s, 2H); 5.37 (s, 2H); 5.43 (d, 1H); 5.64 (d, 1H); 7.56 (s, 1H); 7.84 (dd, 1H); 8.22 (dd, 1H). NMR-C13 (CDCl$_3$+CD$_3$OD): 7.87; 36.11; 42.16; 45.33; 52.67; 54.52; 56.47; 61.97; 73.26; 101.17; 110.81; 115.49; 122.93; 128.63; 139.83; 144.28; 146.40; 149.27; 151.27; 151.64; 152.31; 153.82; 156.50; 159.71; 172.56. IR (KBr): 1607; 1656; 1732; 2795; 3411.

Example 47

5-ethyl-9,10-difluoro-5-hydroxy-12-(1-piperidinylmethyl)-1,4,5,13-tetrahydro-3H,15H-oxepino[3',4':6,7]indolizino[1,2-b]quinoline-3,15-dione The procedure described in Examples 30.a., 30.b. and 30.c. is applied to 3,4-difluoroaniline in order to produce ethyl 2-chloro-4-chloromethyl-6,7-difluoro-3-quinolinecarboxylate which is treated according to the procedure of Example 30.d., using piperidine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A light green solid is obtained, m.p. 266–268° C.

NMR-1H (DMSO): 0.86 (t, 3H); 1.42–1.49 (m, 6H); 1.85 (q, 2H); 2.47 (m, 4H); 3.06 (d, 1H); 3.48 (d, 1H); 4.00 (q, 2H); 5.31 (s, 2H); 5.46 (dd, 2H); 6.04 (s, 1H); 7.37 (s, 1H); 8.14 (m, 1H); 8.46 (m, 1H). NMR-C13 (DMSO): 8.43; 24.01; 25.8; 36.52; 42.56; 50.60; 54.29; 56.91; 61.41; 73.30; 99.81; 111.86; 115.67; 122.94; 130.10; 140.66; 144.49; 146.12; 153.18; 155.86; 159.14; 172.03. IR (KBr): 1258; 1452; 1517; 1607; 1661; 1731; 2950; 3480.

Example 48

12-[(dimethylamino)methyl]-5-ethyl-9,10-difluoro-5-hydroxy-1,4,5,13-tetrahydro-3H,15H-oxepino[3',4':6,7]indolizino[1,2-b]quinoline-3,15-dione The procedure described in Examples 30.a., 30.b. and 30.c. is applied to 3,4-difluoroaniline in order to produce ethyl 2-chloro-4-chloromethyl-6,7-difluoro-3-quinolinecarboxylate which is treated according to the procedure of Example 30.d., using dimethylamine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A light beige solid is obtained, m.p. >270° C.

NMR-1H (DMSO): 0.86 (t, 3H); 1.85 (q, 2H); 2.25 (s, 6H); 3.08 (d, 1H); 3.47 (d, 1H); 3.95 (q, 2H); 5.28 (s, 2H); 5.46 (dd, 2H); 6.06 (s, 1H); 7.37 (s, 1H); 8.14 (s, 1H); 8.42 (s, 1H). NMR-C13 (DMSO): 8.42; 14.06; 33.36; 45.44; 50.57; 61.40; 65.14; 72.05; 72.93; 73.30; 99.82; 99.95; 115.78; 115.85; 122.96; 125.01; 130.08; 140.56; 144.54; 146.16; 155.86; 159.19; 172.03. IR (KBr): 1516; 1613; 1654; 1731; 3450.

Example 49

9-chloro-5-ethyl-5-hydroxy-10-methyl-12-(4-morpholinylmethyl)-1,4,5,13-tetrahydro-3H,15H-oxepino[3',4':6,7]indolizino[1,2-b]quinoline-3,15-dione The procedure described in Examples 30.a., 30.b. and 30.c. is applied to 3-chloro-4-methylaniline in order to produce ethyl 2,7-dichloro-4-chloromethyl-6-methyl-3-quinolinecarboxylate which is treated according to the procedure of Example 30.d., using morpholine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A yellow solid is obtained, m.p. >300° C.

NMR-1H (DMSO): 0.87 (t, 3H); 1.84 (q, 2H); 2.50 (s, 4H); 2.58 (s, 3H); 3.07 (d, 1H); 3.46 (d, 1H); 3.57 (s, 4H); 4.08 (dd, 2H); 5.30 (s, 2H); 5.51 (dd, 2H); 6.06 (s, 1H); 7.35 (s, 1H); 8.15 (s, 1H): 8.41 (s, 1H). NMR-C13 (DMSO): 8.42; 20.57; 36.51; 42.55; 50.76; 53.46; 55.86; 61.42; 66.42; 73.29; 99.73; 122.78; 128.40; 130.10; 135.31; 136.26; 139.36 144.61; 147.79; 152.81; 155.86; 159.16; 172.04. IR (Br): 1613; 1657; 1736; 3432.

Example 50

9-chloro-5-ethyl-5-hydroxy-10-methyl-12-[(4-methyl-1-piperazinyl)methyl]-1,4,5,13-tetrahydro-3H,15H-oxepino[3',4':6,7]indolizino[1,2-b] quinoline-3,15-dione The procedure described in Examples 30.a., 30.b. and 30.c. is applied to 3-chloro4-methylaniline in order to produce ethyl 2,7-dichloro-4-chloromethyl-6-methyl-3-quinolinecarboxylate which is treated according to the procedure of Example 30.d., then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A yellow solid is obtained, m.p. 262–268° C.

NMR-1H (DMSO): 0.87 (t, 3H); 1.86 (q, 2H); 2.15 (s, 3H); 2.20–260 (m, 8H); 2.60 (s, 3H); 3.05 (d, 1H); 3.49 (d, 1H); 4.09 (dd, 2H); 5.32 (s, 2H); 5.50 (dd, 2H); 6.05 (s, 1H); 7.37 (s, 1H); 8.21 (s, 1H); 8.43 (s, 1H). NMR-C13 (DMSO): 8.42; 20.56; 36.50; 42.55; 45.91; 50.81; 53.00; 54.94; 55.65; 61.43; 73.29; 79.36; 99.69; 122.75; 126.32; 128.37; 129.84; 135.25; 136.23; 139.87; 144.57; 147.75; 152.76; 155.87; 159.15; 172.04. IR (KBr): 1607; 1658; 1733; 3424.

Example 51

12-{[benzyl(methyl)amino]methyl}-9-chloro-5-ethyl-5-hydroxy-10-methyl-1,4,5,13-tetrahydro-3H,15H-oxepino[3',4':6,7]indolizino[1,2-b]quinoline-3,15-dione The procedure described in Examples 30.a., 30.b. and 30.c. is applied to 3-chloro-4-methylaniline in order to produce ethyl 2,7-dichloro-4-chloromethyl-6-methyl-3-quinolinecarboxylate which is treated according to the procedure of Example 30.d., using N-methylbenzylamine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A yellow solid is obtained, m.p. 275–278° C.

NMR-1H (DMSO): 0.88 (t, 3H); 1.85 (m, 2H); 2.13 (s, 3H); 2.55 (s, 3H); 3.10 (d, 1H); 3.50 (d, 1H); 3.67 (s, 2H); 4.05 (dd, 2H); 5.30 (s, 2H); 5.39–5.57 (dd, 2H); 6.05 (s, 1H); 7.36 (m, 6H); 8.15 (s, 1H); 8.31 (s, 1H). NMR-C13 (DMSO): 9.10; 21.15; 37.20; 42.86; 43.23; 51.32; 55.78; 62.10; 62.88; 73.99; 80.05; 100.44; 123.47; 126.99; 127.32; 128.09; 129.17; 129.96; 130.86; 135.75; 136.84; 139.51; 140.67; 145.38; 148.54; 153.50; 156.54; 159.85; 172.73. IR (KBr): 1609; 1655; 1729; 3395.

Example 52

12-[(4-benzyl-1-piperazinyl)methyl]-9-chloro-5-ethyl-5-hydroxy-10-methyl-1,4,5,13-tetrahydro-3H,15H-oxepino[3',4':6,7]indolizino[1,2-b]quinoline-3,15-dione The procedure described in Examples 30.a., 30.b. and 30.c. is applied to 3-chloro-4-methylaniline in order to produce ethyl 2,7-dichloro4-chloromethyl-6-methyl-3-quinolinecarboxylate which is treated according to the procedure of Example 30.d., using N-benzylpiperazine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A beige solid is obtained, m.p. 244–249° C.

NMR-1H (DMSO): 0.86 (t, 3H); 1.83 (m, 2H); 2.38–2.60 (m, 8H); 2.57 (s, 3H); 3.08 (d, 1H); 3.46 (s, 2H); 4.08 (m, 2H); 5.30 (s, 2H); 5.51 (dd, 2H); 6.05 (s, 1H); 7.30 (m, 6H); 8.16 (s, 1H); 8.40 (s, 1H). NMR-C13 (DMSO): 9.10; 21.23; 37.19; 43.21; 51.48; 53.54; 53.80; 56.35; 62.09; 62.84; 73.97; 97.67; 100.39; 123.45; 127.05; 127.75; 129.02 129.63; 130.61; 135.95; 136.93; 139.14; 140.52; 145.27; 148.45; 153.47; 156.52; 159.83; 172.72. IR (KBr): 1567; 1587; 1652; 1748; 3422.

Example 53

9-chloro-5-ethyl-5-hydroxy-10-methyl-12-(1-piperidinylmethyl)-1,4,5,13-tetrahydro-3H,15H-oxepino[3',4':6,7]indolizino[1,2-b]quinoline-3,15-dione The procedure described in Examples 30.a., 30.b. and 30.c. is applied to 3-chloro-4-methylaniline in order to produce ethyl 2,7-dichloro-4-chloromethyl-6-methyl-3-quinolinecarboxylate which is treated according to the procedure of Example 30.d., using piperidine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A yellow solid is obtained, m.p. 255° C. (dec).

NMR-1H (DMSO): 0.86 (t, 3H); 1.50 (m, 6H); 1.84 (m, 2H); 2.50 (m, 4H); 2.58 (s, 3H); 3.05 (d, 1H); 3.45 (d, 1H); 4.04 (m, 2H); 5.32 (s, 2H); 5.51 (dd, 2H); 6.10 (s, 1H); 7.37 (s, 1H); 8.20 (s, 1H); 8.42 (s, 1H). NMR-C13 (DMSO): 9.11; 21.24; 24.70; 26.50; 37.20; 43.23; 51.43; 55.10; 57.21; 62.09; 73.99; 98.05; 100.38; 123.44; 127.10; 129.12; 130.59; 135.89; 136.91; 140.99; 145.31; 148.50; 153.52; 156.51; 159.85; 172.73. IR (KBr): 1601; 1654; 1728; 3436.

Example 54

12-[(4-benzyl-1-piperazinyl)methyl]-5-ethyl-10-fluoro-5-hydroxy-1,4,5,13-tetrahydro-3H,15H-oxepino[3',4':6,7]indolizino[1,2-b]quinoline-3,15-dione The procedure described in Examples 30.a., 30.b. and 30.c. is applied to 4-fluoroaniline in order to produce ethyl 2-chloro-4-chloromethyl-6-fluoro-3-quinolinecarboxylate which is treated according to the procedure of Example 30.d., using N-benzylpiperazine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A white solid is obtained, m.p. 262° C.

NMR-1H (DMSO): 0.87 (t, 3H); 1.85 (q, 2H); 2.37 (s, 4H); 2.37 (s, 4H); 3.07 (d, 1H); 3.45 (s, 2H); 3.47 (d, 1H); 4.08 (q, 2H); 5.32 (s, 2H); 5.46 (dd, 2H); 6.03 (s, 1H); 7.35 (m, 5H); 7.38 (s, 1H); 7.77 (m, 1H); 8.20 (m, 2H). NMR-C13 (DMSO): 8.41; 36.49; 42.53; 50.65; 52.82; 53.03; 55.95; 61.41; 62.14; 72.3; 99.55; 109.31; 120.14; 120.40; 122.70; 127.05; 128.32 128.55; 128.96; 130.40; 138.42; 139.65; 144.66; 145.83; 152.15; 155.89; 159.15; 161.57; 172.02. IR (KBr): 740; 834; 1071; 1193; 1220; 1288; 1360; 1451; 1516; 1592; 1655; 1749; 2813; 2950; 3434.

Example 55

12-[(4-benzyl-1-piperazinyl)methyl]-5-ethyl-9-fluoro-5-hydroxy-10-methyl-1,4,5,13-tetrahydro-3H,15H-oxepino[3',4':6,7]indolizino[1,2-b]quinoline-3,15-dione The procedure described in Examples 30.a., 30.b. and 30.c. is applied to 3-fluoro-4-methylaniline in order to produce ethyl 2-chloro-4-chloromethyl-7-fluoro-6-methyl-3-quinolinecarboxylate which is treated according to the procedure of Example 30.d., using N-benzylpiperazine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A light beige solid is obtained, m.p. 259° C.

NMR-1H (DMSO): 0.86 (t, 3H); 1.85 (q, 2H); 2.38 (m, 4H); 2.50 (s, 4H); 3.06 (d, 1H); 3.36 (s, 3H); 3.46 (s, 2H); 3.47 (d, 1H); 4.07 (q, 2H); 5.29 (s, 2H); 5.46 (dd, 2H); 6.02 (s, 1H); 7.23–7.35 (m, 6H); 7.8 (d, 1H); 8.35 (d, 1H). NMR-C13 (DMSO): 8.40; 15.45; 36.47; 42.54; 50.7; 52.84; 53.13; 55.81; 61.4; 62.14; 73.29; 99.57; 112.45; 122.61; 124.73; 127.05; 128.32; 128.96; 138.45; 139.81; 1444.68; 152.63; 155.85; 159.15; 172.02. IR(KBr): 1013; 1069; 1169; 1241; 1266; 1475; 1577; 1594; 1655; 1744.

Example 56

12-[(dimethylamino)methyl]-5-ethyl-9-fluoro-5-hydroxy-10-methyl-1,4,5,13-tetrahydro-3H,15H-oxepino[3',4':6,7]indolizino[1,2-b]quinoline-3,15-dione The procedure described in Examples 30.a., 30.b. and 30.c. is applied to 3-fluoro-4-methylaniline in order to produce ethyl 2-chloro-4-chloromethyl-7-fluoro-6-methyl-3-quinolinecarboxylate which is treated according to the procedure of Example 30.d., using dimethylamine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A light beige solid is obtained, m.p. 184–190° C.

NMR-1H (DMSO): 0.86 (t, 3H); 1.85 (q, 2H); 2.26 (s, 6H); 2.5 (s, 3H); 3.05 (d, 1H); 3.48 (d, 1H); 3.98 (q, 2H); 5.28 (s, 2H); 5.46 (dd, 2H); 6.06 (s, 1H); 7.37 (s, 1H); 7.84 (d, 1H); 8.35 (d, 1H). NMR-C13 (DMSO): 8.45; 15.50; 36.52; 45.59; 50.62; 57.36; 61.43; 73.33; 99.66; 112.29; 112.50; 122.67; 124.71; 126.99; 127.20; 127.44; 129.08; 140.16; 144.80; 148.82; 152.71; 155.89; 159.22; 160.75; 172.07. IR (KBr): 1448; 1595; 1653; 1749; 2950; 3438.

Example 57

12-[(diethylamino)methyl]-5-ethyl-9-fluoro-5-hydroxy-10-methyl-1,4,5,13-tetrahydro-3H,15H-oxepino[3',4':6,7]indolizino[1,2-b]quinoline-3,15-dione The procedure described in Examples 30.a., 30.b. and 30.c. is applied to 3-fluoro-4-methylaniline in order to produce ethyl 2-chloro-4-chloromethyl-7-fluoro-6-methyl-3-quinolinecarboxylate which is treated according to the procedure of Example 30.d., using diethylamine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A light beige solid is obtained, m.p. >270° C.

NMR-1H (DMSO): 0.87 (t, 3H); 1.04 (t, 6H); 1.86 (q, 2H); 2.50 (q, 2H); 2.54 (s, 3H); 2.56 (q, 2H); 3.08 (d, 1H); 3.48 (d, 1H); 4.11 (q, 2H); 5.25 (s, 2H); 5.46 (dd, 2H); 6.05 (s, 1H); 7.35 (s, 1H); 7.80 (d, 1H); 8.36 (d, 1H). NMR-C13 (DMSO): 8.45; 11.68; 11.78; 15.43; 15.57; 36.5; 42.5; 46.68; 46.83; 46.99; 50.77; 51.85; 52.08; 61.44; 73.30; 99.60; 112.18; 112.36; 122.6; 124.6; 126.9; 127.1; 128.8; 141.45; 144.6; 148.6; 148.7; 152.65 155.9; 159.1; 160.7; 163.2; 172.1. IR (KBr): 1217; 1295; 1448; 1463; 1507; 1609; 1660; 1725; 2971; 3559.

Suspension of the above free base in absolute ethanol (50 ml/mmol) followed by treatment with ethanolic hydrogen chloride (2.5 N, 5 equ.) allows the corresponding hydrochloride to be obtained. Initially, a yellow solution forms, then a precipitate which is collected by filtering after concentration to 40% of the initial volume, then washed with ether. A vivid yellow solid is obtained, m.p. 269–272° C.

NMR-1H (DMSO): 0.87 (t, 3H); 1.34 (m, 1H); 1.86 (q, 2H); 2.56 (s, 3H); 3.07 (d, 1H); 3.19 (m, 2H); 3.39 (m, 2H); 3.49 (d, 1H); 4.97 (m, 2H); 5.41 (d, 1H); 5.54 (d, 1H); 5.58 (s, 2H); 6.08 (s, 1H); 7.42 (s, 1H); 7.96 (d, 1H); 8.43 (d, 1H); 10.38 (s, 1H). IR (KBr): 1039; 1070; 1226; 1282; 1509; 1654; 1724; 1744; 2921; 3409; 3489.

Example 58

5-ethyl-9-fluoro-5-hydroxy-10-methyl-12-[(4-methyl-1-piperidinyl)methyl]-1,4,5,13-tetrahydro-3H,15H-oxepino[3',4':6,7]indolizino[1,2-b] quinoline-3,15-dione The procedure described in Examples 30.a., 30.b. and 30.c. is applied to 3-fluoro-4-methylaniline in order to produce ethyl 2-chloro-4-chloromethyl-7-fluoro-6-methyl-3-quinolinecarboxylate which is treated according to the procedure of Example 30.d., using 4-methylpiperidine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A yellow solid is obtained, m.p. >250° C.

NMR-1H (DMSO): 1.00–0.80 (complex, 6H); 1.12 (q, 1H); 1.37 (s, 1H); 1.57 (d, 3H); 1.85 (q, 2H); 2.13 (t, 2H); 2.82 (s, 1H); 2.85 (s, 1H); 3.05 (d, 1H); 3.25 (s, 3H); 3.48 (d, 1H); 4.04 (q, 2H); 5.28 (s, 2H); 5.39 (d, 1H); 5.52 (d, 1H); 6.03 (s, 1H); 7.36 (s, 1H); 7.82 (d, 1H); 8.40 (d, 1H). NMR-C13 (DMSO): 0.29; 8.43; 13.68; 15.48; 19.40; 21.93; 23.23; 30.39; 34.20; 36.52; 42.55; 50.67; 53.84; 56.29; 57.67; 61.40; 73.32; 99.59; 112.49; 122.62; 124.80; 127.18; 129.10; 140.31; 144.58; 148.64; 152.69; 155.84; 159.19; 172.05. IR (KBr): 1597; 1653; 1747; 3446.

Example 59

5-ethyl-9-fluoro-5-hydroxy-10-methyl-12-(1-pyrrolidinylmethyl)-1,4,5,13-tetrahydro-3H,15H-oxepino[3',4':6,7]indolizino[1,2-b]quinoline-3,15-dione The procedure described in Examples 30.a., 30.b. and 30.c. is applied to 3-fluoro-4-methylaniline in order to produce ethyl 2-chloro-4-chloromethyl-7-fluoro-6-methyl-3-quinolinecarboxylate which is treated according to the procedure of Example 30.d., using pyrrolidine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A yellow solid is obtained, m.p. >250° C.

NMR-1H (DMSO): 0.86 (t, 3H); 1.72 (s, 4H); 1.85 (q, 2H); 2.57 (s, 4H); 3.05 (d, 1H); 3.28 (s, 3H); 3.48 (d, 1H);

4.18 (q, 2H); 5.28 (s, 2H); 5.39 (d, 1H); 5.52 (d, 1H); 6.03 (s, 1H); 7.36 (s, 1H); 7.82 (d, 1H); 8.35 (d, 1H). NMR-C13 (DMSO): 0.37; 8.47; 15.57; 23.48; 36.53; 42.61; 50.61; 53.45; 54.09; 61.42; 73.33; 99.59; 112.37; 122.64; 124.51; 127.00; 127.25; 128.63; 140.65; 144.77; 148.65; 152.73; 155.87; 159.20; 162.00; 167.00; 172.07. IR (Kflr): 1608; 1656; 1729; 3400.

Example 60

12-[3,6-dihydro-1(2H)-pyridinylmethyl]-5-ethyl-9-fluoro-5-hydroxy-10-methyl-1,4,5,13-tetrahydro-3H, 15H-oxepino[3',4':6,7]indolizino[1,2-b]quinoline-3, 15-dione The procedure described in Examples 30.a., 30.b. and 30.c. is applied to 3-fluoro-4-methylaniline in order to produce ethyl 2-chloro-4-chloromethyl-7-fluoro-6-methyl-3-quinolinecarboxylate which is treated according to the procedure of Example 30.d., using 1,2,3,6-tetrahydropyridine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A yellow solid is obtained, m.p. >250° C.

NMR-1H (DMSO): 0.86 (t, 3H); 1.85 (q, 2H); 2.08 (s, 2H); 3.03 (s, 2H); 3.05 (d, 1H); 3.28 (s, 3H); 3.48 (d, 1H); 4.12 (d, 1H); 5.28 (s, 2H); 5.39 (d, 1H); 5.52 (d, 1H); 5.64 (d, 1H); 6.03 (s, 1H); 7.36 (s, 1H); 7.83 (d, 1H); 8.36 (d, 1H). NMR-C13 (DMSO): 8.45; 15.54; 25.84; 36.54; 42.55; 49.78; 50.68; 52.52; 55.81; 61.42; 73.33; 99.62; 112.53; 122.66; 124.78; 125.03; 127.09; 127.19; 131.73; 139.98; 144.76; 148.79; 152.73; 155.86; 159.19; 160.76; 163.25; 172.07. IR (KBr): 1605; 1656; 1733; 3451.

Example 61

12-[(diisobutylamino)methyl]-5-ethyl-9-fluoro-5-hydroxy-10-methyl-1,4,5,13-tetrahydro-3H,15H-oxepino[3',4':6,7]indolizino[1,2-b]quinoline-3,15-dione The procedure described in Examples 30.a., 30.b. and 30.c. is applied to 3-fluoro-4-methylaniline in order to produce ethyl 2-chloro-4-chloromethyl-7-fluoro-6-methyl-3-quinolinecarboxylate which is treated according to the procedure of Example 30.d., using diisobutylamine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A yellow solid is obtained, m.p. >250° C.

NMR-1H (DMSO): 0.75 (d, 12H); 0.87 (t, 3H); 1.83 (m, 4H); 2.15 (d, 1H); 2.48 (s, 3H); 3.06 (d, 1H); 3.47 (d, 1H); 4.01 (q, 2H); 5.28 (s, 2H); 5.39 (d, 1H); 5.53 (d, 1H); 6.03 (s, 1H); 7.37 (s, 1H); 7.83 (d, 1H); 8.49 (d, 1H). NMR-C13 (DMSO): 9.09; 16.14; 21.73; 26.57; 26.70; 37.15; 43.14; 51.05; 55.49; 62.08; 64.74; 73.98; 100.42; 113.03; 123.38; 125.58; 127.12; 127.32; 128.59; 130.27; 141.32; 145.51; 149.38; 149.51; 153.20; 156.62; 159.86; 161.31; 163.79; 172.72. IR (KBr): 1599; 1656; 1747; 2796; 3448.

Example 62

5-ethyl-9-fluoro-5-hydroxy-10-methoxy-12-[(4-methyl-1-piperazinyl)methyl]-1,4,5,13-tetrahydro-3H,15H-oxepino[3',4':6,7]indolizino[1,2-b] quinoline-3,15-dione The procedure described in Examples 30.a., 30.b. and 30.c. is applied to 3-fluoro-4-methoxyaniline in order to produce ethyl 2-chloro4-chloromethyl-7-fluoro-6-methoxy-3-quinolinecarboxylate which is treated according to the procedure of Example 30.d., then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A light yellow solid is obtained, m.p. 274° C.

NMR-1H (DMSO): 0.86 (t, 3H); 1.85 (q, 2H); 2.15 (s, 3H); 2.31 (m, 4H); 2.47 (m, 4H); 3.06 (d, 1H); 3.47 (d, 1H); 4.05 (m, 2H); 4.05 (s, 3H); 5.28 (s, 2H); 5.45 (dd, 2H); 6.05 (s, 1H); 7.35 (s, 1H); 7.87 (d, 1H); 7.94 (d, 1H). NMR-C13 (DMSO): 8.44; 36.53; 45.58; 45.95; 50.68; 52.86; 55.07; 56.20; 56.47; 61.45; 73.32; 99.19; 105.90; 113.74; 113.91; 122.22; 125.60; 129.46; 138.83; 144.51; 144.62; 144.94; 147.85; 147.98; 150.96; 152.82; 155.34; 155.96; 159.19; 172.09. IR (KBr): 1270; 1515; 1594; 1648; 1747; 2950; 3438.

Example 63

5-ethyl-9-fluoro-5-hydroxy-10-methoxy-12-(1-piperidinylmethyl)-1,4,5,13-tetrahydro-3H,15H-oxepino[3',4':6,7]indolizino[1,2-b]quinoline-3,15-dione The procedure described in Examples 30.a., 30.b. and 30.c. is applied to 3-fluoro-4-methoxyaniline in order to produce ethyl 2-chloro4-chloromethyl-7-fluoro-6-methoxy-3-quinolinecarboxylate which is treated according to the procedure of Example 30.d., using piperidine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A light green solid is obtained, m.p. >275° C.

NMR-1H (DMSO): 0.86 (t, 3H); 1.42–1.50 (m, 6H); 1.84 (q, 2H); 2.50 (m, 4H); 3.05 (d, 1H); 3.48 (d, 1H); 4.03 (s, 2H); 4.05 (s, 3H); 5.30 (s, 2H); 5.45 (dd, 2H); 6.02 (s, 1H); 7.35 (s, 1H); 7.9 (d, 1H) 7.99 (d, 1H). NMR-C13 (DMSO): 8.44; 24.07; 25.9; 36.54; 42.57; 50.60; 54.26; 56.40; 57.11; 61.42; 73.33; 99.17; 105.97; 113.75; 113.92; 122.21; 125.66; 129.46; 139.23; 144.54; 144.98; 147.94; 151.0; 152.82; 155.34; 155.89; 159.20; 172.07. IR (KBr): 860; 1057; 1270; 1514; 1656; 1748; 2857; 2932; 3397.

Suspension of the above free base in absolute ethanol (50 ml/mmol) followed by treatment with ethanolic hydrogen chloride (2.5 N, 5 equ.) allows the corresponding hydrochloride to be obtained. Initially, a yellow solution forms, then a precipitate which is collected by filtering after concentration to 40% of the initial volume, then washed with ether. A light yellow solid is obtained, m.p. 264° C.

NMR-1H (DMSO): 0.86 (t, 3H); 1.42 (m, 1H); 1.70–1.85 (m, 7H); 3.06 (d, 1H); 3.33 (m, 4H); 3.47 (m, 1H); 4.19 (s, 3H); 5.00 (s, 2H); 5.40 (d, 1H); 5.54 (d, 1H); 5.61 (s, 2H); 6.02 (s, 1H); 7.37 (s, 1H); 7.95–8.04 (m, 2H); 10.46 (s, 1H). NMR-C13 (DMSO): 9.12; 22.11; 22.91; 37.63; 43.20; 52.27; 53.20; 54.00; 54.75; 57.91; 58.15; 62.12; 62.78; 73.97; 100.06; 106.96; 107.14; 114.80; 123.20; 126.58; 130.48; 134.14; 145.33; 145.48; 149.49; 149.62; 151.76; 153.84; 156.36; 156.69; 159.76; 172.73. IR (KBr): 1010; 1072; 1240; 1271; 1469; 1511; 1574; 1598; 1648; 1734; 2525; 2944; 3430; 3507.

Example 64

9-chloro-12-[(dimethylamino)methyl]-5-ethyl-5-hydroxy-10-methoxy-1,4,5,13-tetrahydro-3H,15H-oxepino[3',4':6,7]indolizino[1,2-b]quinoline-3,15-dione The procedure described in Examples 30.a., 30.b. and 30.c. is applied to 3-chloro-4-methoxyaniline in order to produce ethyl 2,7-dichloro-4-chloromethyl-6-methoxy-3-quinolinecarboxylate which is treated according to the procedure of Example 30.d., using dimethylamine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A yellow solid is obtained, m.p. >250° C.

NMR-1H (DMSO): 0.86 (t, 3H); 1.84 (q, 2H); 2.29 (s, 6H); 3.06 (d, 1H); 3.42 (d, 1H); 3.98 (q, 2H); 4.05 (s, 3H); 5.27 (s, 2H); 5.45 (s, 2H); 5.95 (s, 1H); 7.32 (s, 1H); 7.82 (s, 1H); 8.19 (s, 1H). NMR-C13 (DMSO): 8.41; 36.50; 42.55; 45.58; 50.62; 56.70; 57.42; 61.42; 73.29; 99.28; 104.66; 122.34; 126.92; 127.55; 129.89; 130.04; 139.19 144.20; 144.81; 151.08; 153.15; 155.91; 159.18; 172.04. IR (KBr): 1048; 1242; 1482; 1611; 1659; 1730; 3301; 3417.

Example 65

9-chloro-5-ethyl-5-hydroxy-10-methoxy-12-(1-piperidinylmethyl)-1,4,5,13-tetrahydro-3H,15H-oxepino[3',4':6,7]indolizino[1,2-b]quinoline-3,15-dione The procedure described in Examples 30.a., 30.b. and 30.c. is applied to 3-chloro-4-methoxyaniline in order to produce ethyl 2,7-dichloro-4-chloromethyl-6-methoxy-3-quinolinecarboxylate which is treated according to the procedure of Example 30.d., using piperidine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. The free base thus obtained is suspended in absolute ethanol (50 ml/mmol) then treated with ethanolic hydrogen chloride (2.5 N, 5 equ.). Initially a yellow solution forms, then a precipitate which is collected by filtering after concentration to 40% of initial volume, and washed with ether. An orange solid is obtained, m.p. >250° C.

NMR-1H (DMSO): 0.86 (t, 3H); 1.43 (q, 1H); 1.70 (d, 1H); 1.76 (m, 2H); 1.86 (m, 4H); 3.07 (d, 1H); 3.28 (m, 2H); 3.47 (m, 3H); 4.20 (s, 3H); 5.00 (q, 2H); 5.41 (d, 1H); 5.54 (d, 1H); 5.62 (s, 1H); 6.10 (s, 1H); 7.36 (s, 1H); 7.88 (s, 1H); 8.31 (s, 1H). NMR-C13 (CF3COOD): 8.44; 22.11; 24.79; 38.27; 43.51; 54.28; 56.01; 58.51; 58.75; 64.23; 77.59; 104.22; 110.49; 124.68; 129.44; 131.91; 136.61; 140.01; 141.33; 144.72; 158.25; 161.10; 161.89; 178.85. IR (KBr): 1079; 1288; 1488; 1562; 1578; 1648; 1747; 2936; 3406.

Example 66

12-[3,6-dihydro-1(2H)-pyridinylmethyl]-5-ethyl-5-hydroxy-10-methoxy-1,4,5,13-tetrahydro-3H,15H-oxepino[3',4':6,7]indolizino[1,2-b]quinoline-3,15-dione The procedure described in Examples 30.a., 30.b. and 30.c. is applied to 4-methoxyaniline in order to produce ethyl 2-chloro-4-chloromethyl-6-methoxy-3-quinolinecarboxylate which is treated according to the procedure of Example 30.d., using 1,2,3,6-tetrahydropyridine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. The free base thus obtained is suspended in absolute ethanol (50 ml/nmmol) then treated with ethanolic hydrogen chloride (2.5 N, 5 equ.). Initially a yellow solution forms, then a precipitate which is collected by filtering after concentration to 40% of initial volume, and washed with ether. A yellow solid is obtained, m.p. >250° C.

NMR-1H (DMSO): 0.86 (t, 3H); 1.87 (q, 2H); 2.32 (m, 1H); 3.07 (d, 1H); 3.48 (m, 3H); 3.89 (m, 8H); 4.06 (s, 3H); 5.08 (m, 2H); 5.40 (d, 1H); 5.54 (d, 1H); 5.63 (q, 2H); 5.67 (d, 2H); 5.93 (d, 2H); 7.37 (s, 1H); 7.59 (q, 1H); 7.79 (d, 1H); 8.19 (d, 1H); 10.80 (s, 1H). NMR-C13 (DMSO): 8.47; 25.97; 36.40; 42.55; 49.75; 50.25; 50.61; 52.36; 56.05; 61.44; 73.36; 98.95; 103.74; 121.99; 122.29; 124.98; 125.50; 128.84; 129.84; 131.18; 138.47; 144.63; 145.18; 150.01; 155.93; 159.24; 172.10. IR (KBr): 827; 1065; 1228; 1289; 1592; 1653; 1746; 2363; 3373.

Example 67

5-ethyl-5-hydroxy-10-methoxy-12-[(4-methyl-1-piperidinyl)methyl]-1,4,5,13-tetrahydro-3H,15H-oxepino[3',4':6,7]indolizino[1,2-b]quinoline-3,15-dione The procedure described in Examples 30.a., 30.b. and 30.c. is applied to 4-methoxyaniline in order to produce ethyl 2-chloro-4-chloromethyl-6-methoxy-3-quinolinecarboxylate which is treated according to the procedure of Example 30.d., using 4-methylpiperidine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A yellow solid is obtained, m.p. >250° C.

NMR-1H (CF3COOD): 1.17 (m, 6H); 1.62 (m, 2H); 1.89 (s, 1H); 2.07 (q, 2H); 2.25 (m, 2H); 3.54 (m, 3H); 3.89 (d, 1H); 4.02 (s, 2H); 4.19 (s, 3H); 7.94 (s, 1H); 8.10 (m, 1H); 8.29 (s, 1H); 8.50 (m, 1H). NMR-C13 (CF3COOD): 8.43; 13.79; 17.43; 20.89; 30.01; 32.85; 38.26; 43.50; 54.13; 56.09; 57.87; 58.27; 64.22; 77.57; 107.37; 110.56; 125.75 129.36; 129.42; 132.78; 136.04; 136.65; 139.91; 140.38; 144.31; 158.30; 161.94; 164.90; 178.84. IR (KBr): 825; 1056; 1230; 1260; 1516; 1641; 1655; 1736; 2921; 3395.

Example 68

5-ethyl-5-hydroxy-10-methoxy-12-[(4-methyl-1-piperazinyl)methyl]-1,4,5,13-tetrahydro-3H,15H-oxepino[3',4':6,7]indolizino[1,2-b]quinoline-3,15-dione The procedure described in Examples 30.a., 30.b. and 30.c. is applied to 4-methoxyaniline in order to produce ethyl 2-chloro-4-chloromethyl-6-methoxy-3-quinolinecarboxylate which is treated according to the procedure of Example 30.d., then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A yellow solid is obtained, m.p. 215–219° C.

NMR-1H (DMSO): 0.85 (t, 3H); 1.85 (m, 2H); 2.15 (s, 3H); 2.35 (m, 4H); 2.5 (m, 4H); 3.25 (dd, 2H); 3.95 (s, 3H); 4.05 (s, 2H); 5.3 (s, 2H); 5.45 (dd, 2H); 6 (s, 1H); 7.3 (s, 1H); 7.5 (d, 1H); 7.7 (s, 1H); 8.05 (d, 1H). NMR-C13 (DMSO): 9.12; 14.36; 20.08; 23.93; 46.61; 51.35; 53.58; 55.71; 56.34; 56.73; 58.37; 62.11; 74.03; 99.62; 104.49; 122.66; 123.11;

129.54; 130.53; 131.82; 139.05; 145.3; 145.86; 150.67; 156.62; 158.71; 159.91; 172.77. IR (KBr): 1590; 1624; 1655; 1744; 2801; 2935; 3423.

Example 69

5-ethyl-5-hydroxy-10-methoxy-12-(1-pyrrolidinylmethyl)-1,4,5,13-tetrahydro-3H,15H-oxepino[3',4':6,7]indolizino[1,2-b]quinoline-3,15-dione The procedure described in Examples 30.a., 30.b. and 30.c. is applied to 4-methoxyaniline in order to produce ethyl 2-chloro-4-chloromethyl-6-methoxy-3-quinolinecarboxylate which is treated according to the procedure of Example 30.d., using pyrrolidine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A yellow solid is obtained, m.p. >250° C.

NMR-1H (DMSO): 0.85 (t, 3H); 1.7 (s, 4H); 1.85 (q, 2H); 2.55 (s, 4H); 3.25 (dd, 2H); 3.9 (s, 3H); 4.15 (s, 2H); 5.25 (s, 2H); 5.45 (dd, 2H); 6 (s, 1H); 7.35 (s, 1H); 7.5 (d, 1H); 7.7 (s, 1H); 8.05 (d, 1H). NMR-C13 (DMSO): 9.68; 24.74; 51.8; 54.71; 55.25; 56.3; 56.87; 62.3; 62.64; 74.5; 100.14; 104.8; 104.92; 123.19; 123.45; 129.79; 130.49; 132.32; 132.50; 140.5; 145.83; 146.4; 151.27; 157.15; 159.25; 160.45; 173.3. IR (KBr): 1255; 1516; 1535; 1613; 1655; 1735; 3438; 3762; 3830.

Example 70

12-[(4-benzyl-1-piperazinyl)methyl]-5-ethyl-5-hydroxy-10-methoxy-1,4,5,13-tetrahydro-3H,15H-oxepino[3',4':6,7]indolizino[1,2-b]quinoline-3,15-dione The procedure described in Examples 30.a., 30.b. and 30.c. is applied to 4-methoxyaniline in order to produce ethyl 2-chloro-4-chloromethyl-6-methoxy-3-quinolinecarboxylate which is treated according to the procedure of Example 30.d., using N-benzylpiperazine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A beige solid is obtained, m.p. >250° C.

NMR-1H (DMSO): 0.85 (t, 3H); 1.85 (q, 2H); 3.45 (s, 2H); 2.4 (m, 4H); 2.55 (m, 4H); 3.25 (dd, 2H); 3.45 (s, 2H); 3.95 (s, 3H); 4.05 (s, 2H); 5.3 (s, 2H); 5.45 (dd, 2H); 6 (s, 1H); 7.3 (m, 6H); 7.5 (d, 1H); 7.75 (s, 1H); 8 (d, 1H). NMR-C13 (DMSO): 7.38; 49.56; 51.89; 54.46; 54.82; 54.98; 55.1; 60.1; 60.35; 61.11; 72.26; 97.86; 102.6; 102.76;;120.9; 121; 121.2; 121.4; 126; 127.25; 127.77; 127.88; 128.76; 130.13; 130.2; 137.25; 137.36; 143.53 144.08; 148.86; 156.86; 156.95; 158.15; 171.02. IR (KBr): 1235; 1259; 1517; 1586; 1614; 1654; 1747; 2927; 3450; 3762; 3848.

Suspension of the above free base in absolute ethanol (50 ml/mmol) followed by treatment with ethanolic hydrogen chloride (2.5 N, 5 equ.) allows the corresponding hydrochloride to be obtained. Initially, a yellow solution forms, then a precipitate which is collected by filtering after concentration to 40% of the initial volume, then washed with ether. A yellow solid is obtained, m.p. >250° C.

NMR-1H (DMSO): 0.85 (t, 3H); 1.85 (q, 2H); 2.5 (s, 2H); 2.65 (m, 2H); 3 (m, 2H); 3.2 (m, 2H); 3.35 (dd, 2H); 3.35 (s, 2H); 3.95 (s, 3H); 4.15 (s, 2H); 4.3 (s, 2H); 5.3 (s, 2H); 5.45 (dd, 2H); 7.3 (s, 1H); 7.4 (s, 2H); 7.55 (m, 2H); 7.7 (s, 1H); 8.05 (d, 1H); 10.45 (s, 1H). IR (KBr): 1207; 1233; 1439; 1449; 1458; 1508; 1610; 1620; 1655; 1727; 3398.

Example 71

9-chloro-5-ethyl-5-hydroxy-10-methyl-12-[(4-methyl-1-piperidinyl)methyl]-1,4,5,13-tetrahydro-3H,15H-oxepinol3',4':6,7]indolizino[1,2-b]quinoline-3,15-dione The procedure described in Examples 30.a., 30.b. and 30.c. is applied to 3-chloro-4-methylaniline in order to produce ethyl 2,7-dichloro-4-chloromethyl-6-methyl-3-quinolinecarboxylate which is treated according to the procedure of Example 30.d., using 4-methylpiperidine instead of N-methylpiperazine, then reduced according to the method of Example 30.e. into the corresponding quinolinemethanol. The latter is coupled with compound (M) as described in Stage 11.j. of Example 11. The resultant coupled product is cyclized according to the procedure of Stage 11.k. A yellow solid is obtained, m.p. >275° C.

NMR-1H (DMSO): 0.86 (m, 6H); 1.15 (m, 2H); 1.37 (m, 1H); 1.60 (m, 2H); 1.80 (m, 2H); 2.10 (m, 2H); 2.60 (s, 3H); 2.80 (m, 2H); 3.05 (d, 1H); 3.48 (d, 1H); 4.02 (s, 2H); 5.30 (s, 2H); 5.45 (dd, 2H); 6.02 (s, 1H); 7.40 (s, 1H); 8.20 (s, 1H); 8.40 (s, 1H). NMR-C13 (DMSO): 9.10; 21.28; 22.61; 31.07; 34.89; 37.18; 43.22; 54.53 56.83; 62.10; 73.94; 80.06; 100.43; 123.41; 127.08; 129.11; 130.58; 135.88; 136.89; 141.00; 145.28; 148.49; 153.51; 156.60; 159.85; 172.77; 174.05. IR (KBr): 1605; 1657; 1734; 3342.

Example 72

10-(benzyloxy)-5-ethyl-9-fluoro-5-hydroxy-1,4,5,13-tetrahydro-3H,15H-oxepino[3',4':6,7]indolizino[1,2-b]quinoline-3,15-dione The procedure described in Stage 11.i. is applied to 3-fluoro-4-methoxy-acetanilide in order to produce 2-chloro-7-fluoro-6-methoxy-3-quinolinecarbaldehyde which is treated with an excess of boron tribromide in dichloromethane at ambient temperature for 24 hours. 2-chloro-7-fluoro-6-hydroxy-3-quinolinecarbaldehyde is obtained, which is O-benzylated in dimethylformamide in the presence of benzyl bromide and of potassium carbonate in order to produce 6-(benzyloxy)-2-chloro-7-fluoro-3-quinolinecarbaldehyde, which is reduced with sodium borohydride in methanol in order to produce the corresponding quinolinemethanol. The latter is coupled with compound (M) as described in Stage 11.j. of Example 11. The resultant coupled product is cyclized according to the procedure of Stage 11.k. A yellow solid is obtained, m.p. >275° C.

NMR-1H (DMSO): 0.86 (t, 3H); 1.85 (q, 2H); 3.05 (d, 1H); 5.25 (s, 2H); 5.37 (s, 2H); 5.45 (dd, 2H); 6.05 (s, 1H); 7.4–7.6 (m, 5H); 7.88 (d, 1H); 7.95 (d, 1H); 8.56 (s, 1H).

Example 73

5-ethyl-9-fluoro-5,10-dihydroxy-1,4,5,13-tetrahydro-3H,15H-oxepino[3',4':6,7]indolizino[1,2-b]quinoline-3,15-dione The hydrogenolysis procedure of Example 14 is applied to the compound of Example 72. A yellow solid is obtained, m.p. >275° C.

NMR-1H (DMSO): 0.86 (t, 3H); 1.85 (q, 2H); 3.05 (d, 1H); 5.25 (s, 2H); 5.37 (s, 2H); 5.45 (dd, 2H); 6.05 (s, 1H); 7.8 (d, 1H); 7.90 (d, 1H); 8.56 (s, 1H).

Example 74

5-ethyl-9,10-difluoro-3,15-dioxo-4,5,13,15-tetrahydro-1H,3H-oxepino[3',4':6,7]indolizino[1,2-b]quinolin-5-yl 2-aminoacetate hydrochloride 74a. 5-ethyl-9,10-difluoro-3,15-dioxo-4,5,13,15-tetrahydro-1H,3H-oxepino[3',4':6,7]indolizino[1,2-b]quinolin-5-yl 2-[(tert-butoxycarbonyl)amino]acetate A mixture of 5-ethyl-9,10-difluoro-5-hydroxy-1,4,5,13-tetrahydro-3H,15H-oxepino[3',4':6,7]indolizino[1,2-b]quinoline-3,15-dione (200 mg, 0.526 mmol, example 18), N-Boc-glycine (185 mg, 1.051 mmol) and a catalytic quantity of 4-dimethylaminopyridine (20 mg) in anhydrous pyridine (10 ml) is treated at 0° C. and under argon with dicyclohexylcarbodiimide (239 mg, 1.16 mmol), then agitated at ambient temperature for 48 hours. The volatiles are driven off under vacuum and the residue is chromatographed (SiO$_2$, 1% methanol in chloroform) in order to produce the desired intermediate (40 mg, 14%), a yellow solid.

NMR-1H (CDCl$_3$): 1.20 (t, 3H); 1.38 (s, 9H); 1.40–1.70 (m, 2H); 3.10 (d, 1H); 4.00 (d, 2H); 4.30 (d, 1H); 5.00 (t, 1H); 5.20 (s, 2H); 5.30–5.90 (dd, 2H); 7.20 (s, 1H); 7.50–8.10 (m, 2H); 8.30 (s, 1H).

74b. 5-ethyl-9,10-difluoro-3,15-dioxo-4,5,13,15-tetrahydro-1H,3H-oxepino[3',4':6,7]indolizino[1,2-b]quinolin-5-yl 2-aminoacetate hydrochloride The intermediate obtained above (40 mg, 0.072 mmol) in solution in dichloromethane (10 ml) is maintained at 0° C. and dioxan saturated with hydrogen chloride (8 ml) is added dropwise. The yellow suspension thus formed is maintained under agitation for 2 hours, then the volatiles are driven off under vacuum. The residue, taken up in water (5 ml), is washed with dichloromethane (3×30 ml). The aqueous phase is frozen and lyophilized in order to produce the expected salt, a hygroscopic yellow solid (20 mg, 50%).

NMR-1H (CDCl$_3$): 1.00 (t, 3H); 2.15 (m, 1H); 2.30 (m, 1H); 3.60 (d, 1H); 3.90 (d, 1H); 4.15 (s, 2H); 5.10 (s, 2H); 5.40 (d, 1H); 5.70 (d, 2H); 7.40 (s, 1H); 7.80 (m, 2H); 8.50 (s, 1H).

Example 75

5-ethyl-9,10-difluoro-3,15-dioxo-4,5,13,15-tetrahydro-1H,3H-oxepino[3',4':6,7]indolizino[1,2-b]quinolin-5-yl 3-aminopropanoate The procedure of Example 74 is applied to 5-ethyl-9,10-difluoro-5-hydroxy-1,4,5,13-tetrahydro-3H,15H-oxepino[3',4':6,7]indolizino[1,2-b]quinoline-3,15-dione using N-Boc-β-alanine instead of N-Boc-glycine, then the Boc protector of the intermediate thus obtained is cleaved by treatment with trifluoroacetic acid in dichloromethane. The volatiles are evaporated off under vacuum and the residue is taken up in dichloromethane. The resultant solution is washed with dilute bicarbonate, dried and evaporated. A yellow solid is obtained.

By applying the method of Examples 74 and 75 to other compounds, for example to those disclosed in the present application, similar results are obtained. In this way an entire class of campothecin analogues is accessible in "pro-drug" form.

Example 76

2,9-diethyl-9-hydroxy-1,2,3,9,10,16-hexahydro-13H-[1,3]oxazino[5,6-f]oxepino[3',4':6,7]indolizino[1,2-b]quinoline-11,14-dione A suspension of 5-ethyl-5,10-dihydroxy-1,4,5,13-tetrahydro-3H,15H-oxepino[3',4':6,7]indolizino[1,2-b]quinoline-3,15-dione (84 mg, example 14) in acetic acid (2.5 ml) is treated with 1,3,5-triethylhexahydrotriazine (0.5 ml). The reaction mixture is agitated at 70° C. for 30 minutes, then evaporated under vacuum. The residue is taken up in ethanol, filtered and washed with ether. A solid is obtained, m.p. >275° C.

NMR-1H (DMSO): 0.87 (t, 3H); 1.50 (t, 3H); 1.85 (q, 2H); 2.77 (q, 2H); 3.05 (d, 1H); 3.47 (d, 1H); 4.37 (s, 2H); 5.00 (s, 2H); 5.22 (s, 2H); 5.45 (dd, 2H); 6.00 (s, 1H); 7.34 (s, 1H); 7.36 (d, 1H); 7.93 (d, 1H); 8.53 (s, 1H). NMR-C13 (DMSO): 8.46; 13.48; 36.46; 42.49; 45.49; 46.44; 50.75; 61.43; 73.33; 82.06; 99.02; 112.90; 122.00; 122.98; 125.42; 127.04; 129.04; 130.20; 144.09; 144.97; 149.87; 152.92; 155.98; 172.07. IR (KBr): 1045; 1215; 1502; 1604; 1657, 1722.

Example 77

9-ethyl-9-hydroxy-2-methyl-1,2,3,9,10,16-hexahydro-13H-[1,3]oxazino[5,6-f]oxepino[3',4':6,7]indolizino[1,2-b]quinoline-11,14-dione A suspension of 5-ethyl-5,10-dihydroxy-1,4,5,13-tetrahydro-3H,15H-oxepino[3',4':6,7]indolizino[1,2-b]quinoline-3,15-dione (200 mg, example 14) in acetic acid (5 ml) is treated with hexahydro-1,3,5-trimethyltriazine (110 mg). The reaction mixture is agitated at 70° C. for 30 minutes, then evaporated under vacuum. The residue is taken up in ethanol, filtered and washed with ether. A solid is obtained, m.p. >275° C.

NMR-1H (DMSO): 0.87 (t, 3H); 1.85 (q, 2H); 3.04 (d, 1H); 3.48 (d, 1H); 4.33 (s, 2H); 4.93 (s, 2H); 5.28 (s, 2H); 5.45 (dd, 2H); 6.01 (s, 1H); 7.35 (s, 1H); 7.38 (d, 1H); 7.94 (d, 1H); 8.49 (s, 1H). NMR-C13 (DMSO): 8.46; 36.43; 37.85; 42.55; 48.68; 50.79; 61.43; 73.35; 83.82; 99.04; 112.49; 122.04; 123.00; 125.46; 127.14; 129.07; 130.27; 144.99; 149.95; 152.46; 155.99; 172.09. IR (KBr): 1047; 1058; 1219; 1246; 1295; 1439; 1504; 1604, 1655, 1735.

Example 78

2-benzyl-9-ethyl-9-hydroxy-1,2,3,9,10,16-hexahydro-13H-[1,3]oxazino[5,6-f]oxepino[3',4':6,7]indolizino[1,2-b]quinoline-11,14-dione A suspension of 5-ethyl-5,10-dihydroxy-1,4,5,13-tetrahydro-3H,15H-oxepino[3',4':6,7]indolizino[1,2-b]quinoline-3,15-dione (200 mg, example 14) in acetic acid (5 ml) is treated with 1,3,5-tribenzylhexahydrotriazine (285 mg). The reaction mixture is agitated at 70° C. for 30 minutes, then evaporated under vacuum. The residue is taken up in ethanol, filtered and washed with ether. A solid is obtained, m.p. >275° C.

NMR-1H (DMSO): 0.85 (t, 3H); 1.85 (q, 2H); 3.05 (d, 1H); 3.47 (d, 1H); 3.96 (s, 2H); 4.33 (s, 2H); 5.04 (s, 2H); 5.17 (s, 2H); 5.44 (dd, 2H); 6.01 (s, 1H); 7.38 (m, 6H); 7.42 (d, 1H); 7.97 (d, 1H); 8.42 (s, 1H). NMR-C13 (DMSO): 8.42; 19.96; 36.45; 42.51; 46.36; 50.78; 55.38; 61.39; 73.31; 99.00; 112.55; 122.01; 123.08; 125.38; 127.09; 127.47; 128.70; 129.14; 130.35; 128.40; 139.19; 144.18; 149.99: 152.84; 155.92; 159.24; 172.05. IR (KBr): 1056; 1205; 1225; 1248; 1504; 1535; 1599; 1655; 1726.

Example 79

2-benzyl-9-ethyl-5-fluoro-9-hydroxy-1,2,3,9,10,16-hexahydro-13H-11,3]oxazino[5,6-f]oxepino[3',4':6,7]indolizino[1,2-b]quinoline-11,14-dione A suspension of 5-ethyl-9-fluoro-4,5-dihydro-5,10-dihydroxy-1H-oxepino[3',4':6,7]indolizino[1,2-b]quinoline-3,15(4H,13H)-dione (200 mg, example 73) in acetic acid (5 ml) is treated with 1,3,5-tribenzylhexahydrotriazine (285 mg). The reaction mixture is agitated at 70° C. for 30 minutes, then evaporated under vacuum. The residue is taken up in ethanol, filtered and washed with ether. A solid is obtained, m.p. >250° C.

NMR-1H (DMSO): 0.85 (t, 3H); 1.85 (q, 2H); 3.05 (d, 1H); 3.48 (d, 1H); 3.95 (s, 2H); 4.45 (s, 2H); 5.20 (s, 4H); 5.45 (dd, 2H); 6.05 (s, 1H); 7.40 (s, 7H); 7.90 (d, 1H); 8.45 (s, 1H). IR (KBr): 1248; 1451; 15001; 1598; 1657; 1727.

Example 80

(+)-5-Ethyl-5-hydroxy-1,3,4,5,8,9-hexahydrooxepino[3,4-c]pyridin-3,9-dione[(+)-EHHOPD]

80.a. Quinidine salt of 3-(3-benzyloxymethyl-2-methoxy-4-pyridyl)-3-hydroxy-pentanoic acid Tertiobutyl 3-(3-benzyloxymethyl-2-methoxy-4-pyridyl)-3-hydroxy-pentanoate (40 g; 100 mmol) is treated with trifluoroacetic acid (150 ml) and the reaction medium is agitated for 18 hours at 20° C. After evaporation of the trifluoroacetic acid, methylene chloride (200 ml) is poured in and a saturated solution of sodium bicarbonate is introduced until the pH=7.5–8. After decantation, the aqueous phase is washed with 100 ml of methylene chloride. The pH of the aqueous phase is then adjusted to 1 by the addition of a solution of 6N hydrochloric acid. The product is then extracted from the aqueous phase with methylene chloride (2 times 200 ml). The solution is dried over magnesium sulphate and concentrated. The 3-(3-benzyloxymethyl-2-methoxy-4-pyridyl)-3-hydroxy-pentanoic acid (31.1 g; 90 mmol) thus obtained, taken up in isopropyl alcohol (30 ml), is treated with a solution of quinidine (29.2 g; 90 mmol) in isopropyl alcohol (30 ml) at 50° C. under agitation until complete dissolution. Then the reaction medium is left so that temperature reduces to 40° C., the agitation is stopped and the temperature allowed to drop to 20° C. The medium is taken to 0° C. without agitation then maintained at this temperature for 16 hours. Then the temperature is allowed to rise to 20° C. and agitation is carried out until crystallization. The medium is diluted with isopropyl alcohol then filtered. The precipitate is rinsed with isopropyl alcohol. The salt of the (+) enantiomer precipitates (m=26.6 g) while the salt of the (−) enantiomer remains in solution in the isopropyl alcohol. Thus the filtrate is recovered which is concentrated in order to produce an oil (34 g) which is used without other purification in the following stage.

The products are analyzed by HPLC on a 5 μ CHIRAL AGP column (10 cm×4 mm) eluted with a 30/920/50 isopropyl alcohol/water/phosphate buffer mixture, pH=6.5, at a flow rate of 1.2 ml/min, UV detection at 280 nm. The retention times obtained are 6.4 minutes for the (−) enantiomer and 2.8 minutes for the (+) enantiomer. The (−) enantiomer/(+) enantiomer ratio is 83/17.

80.b. (−)-3-(3-benzyloxymethyl-2-methoxy-4-pyridyl)-3-hydroxy-pentanoic acid The solution in isopropyl alcohol of the quinidine salt of the (−) enantiomer of 3-(3-benzyloxymethyl-2-methoxy-4-pyridyl)-3-hydroxy-pentanoic acid (Stage 80.a) is concentrated. The concentrate is taken up in 270 ml of methylene chloride and 270 ml of a 1N solution of hydrochloric acid. The reaction medium is agitated for 16 hours at 20° C. After decantation, the organic phase is concentrated, the concentrate is taken up in methanol in order to be used in the following stage.

13.5 g of product (yield of 87%) and a (−)enantiomer/(+) enantiomer proportion of 85/15 are obtained.

The HPLC retention times (same protocol as in 1.a.) are:
(−) enantiomer: 6.4 minutes
(+) enantiomer: 2.8 minutes

80.c. (+)-5-Ethyl-5-hydroxy-1,3,4,5,8,9-hexahydrooxepino[3,4-c]pyridin-3,9-dione (−)-3-(3-benzyloxymethyl-2-methoxy-4-pyridyl)-3-hydroxy-pentanoic acid (13.5 g; 39 mmol; Stage 80.b) is put in solution in 87 ml of methanol. This solution is poured under nitrogen onto 10% Palladium on damp carbon at 50% (27.7 g; 13 mmol). The reaction medium is agitated for 5 minutes, then it is poured into a solution of ammonium formate (11.5 g; 183 mmol) in 135 ml of methanol. The reaction medium is agitated for 30 minutes while allowing the temperature to rise, then it is heated at 40° C. for 30 minutes. The medium is then filtered on a bed of Clarcel followed by concentrating. 40 ml of toluene is poured in which is evaporated off; this operation is repeated in order to eliminate the methanol. The residue thus obtained is taken up in 45 ml of THF. Then a solution of dicyclohexylcarbodiimide (7.180 g; 34.5 mmol) in 20 ml of THF is then poured in. The reaction medium is heated to 50° C. for 1 hour. The mixture is taken to 20° C. then the dicyclohexylurea is filtered. The filtrate is concentrated to dryness. The residue is put in solution in 46 ml of acetonitrile, 6.0 g (40.5 mmol.) of sodium iodide then 5.13 ml (40.5 mmol) of trimethylsilyl chloride are added. The reaction medium is maintained under agitation at ambient temperatue for 5 hours. Then 28 ml of acetonitrile and 5.6 ml of water are added. The precipitate obtained is filtered then taken up in 1 ml of water, and the pH is adjusted to 7.5 by the addition of a solution of ammonium hydroxide. The solid obtained is filtered and dried. M=4.2 g of final product is obtained with a yield of 34% and a (+) enantiomer/(−) enantiomer proportion of 88.4/11.6.

HPLC analysis is carried out on a Chiralcel OD column 25 cm×4.6 mm the eluants used are heptane 600 and ethanol 400, the flow rate is 1 ml/min 210 nm. The retention times obtained are
(−) enantiomer: 7.1 minutes
(+) enantiomer: 9 minutes.

The product is taken up in acetone (40 ml), then water (150 ml) is added. The reaction is left to precipitate and 3 g of product is obtained with a (+) enantiomer/(−) enantiomer proportion of 99.4/0.6.

NMR $^1$H (250 MHz, DMSO D6): 0.8 (t, 3H, $CH_3$—$CH_2$); 1.65 (m, 2H, $CH_2$—$CH_3$); 3.00–3.35 (q, 1H+1H, —$CH_2$—C=O); 5.3 (q, 2H, $CH_2$—O); 5.7 (s, —OH); 6.35 (d, aromatic 1H); 7.3 (d, aromatic 1H); 11.7 (s, N—H).

Example 81

(+)-5-ethyl-9,10-difluoro-5-hydroxy-4,5,13,15-tetrahydro-1H,3H-oxepino[3',4':6,7]indolizino[1,2-b]quinoline-3,15-dione

81.a. N-(3,4-difluorophenyl)acetamide

A mixture of 3,4-difluoroaniline (50 ml; 0.5 mole) and triethylamine (70 ml; 0.5 mol) in dichloromethane (1.5 l) is cooled down using an ice bath. Acetic anhydride (71.5 ml; 0.75 mol) is added dropwise and the reaction mixture is then agitated for 1 hour at ambient temperatue. The mixture obtained is then washed successively with water, a 10% solution of sodium bicarbonate and saturated salt water. The organic fraction is dried over sodium sulphate and concentrated under reduced pressure. The residue is suspended in pentane, filtered and dried under reduced pressure in order to produce the product in the title (78 g; 91% yield) in the form of a whitish solid (M.p. 126–127.5° C.).

NMR $^1$H (DMSO): 2.15 (s, 3H); 7.10–7.65 (m, 2H); 7.65–8.10 (m, 1H); 10.30 (wide peak, 1H).

81.b. 2-chloro-6,7-difluoro-3-quinoline-3-carbaldehyde

The general procedure described by Meth-Cohn et al., *J. Chem. Soc. Perkin Trans. I*, 1981, 1520 and 2509 is used.

The product of Stage 81.a (32 g; 220 mmol) is added to a Vilsmeyer reagent, obtained by the dropwise addition under an argon atmosphere of phosphorus oxychloride (103 ml; 1.1 mol) in anhydrous DMF (34 ml; 440 mmol) cooled down in an ice bath and agitated for 30 minutes before leaving the temperature to rise to ambient temperature. The mixture thus obtained is agitated at 70° C. for 16 hours. After returning the reaction medium to ambient temperature, it is added dropwise to a water-ice mixture (400 ml) and agitated for 2 hours. The precipitate obtained is filtered and washed with water, then dried in order to produce the product in the title (9 g; 18% yield) in the form of a yellow solid (M.p. 226.5–229° C.).

NMR 1H (DMSO): 8.17 (dd, 1H); 8.39 (dd, 1H); 8.97 (d, 1H); 10.34 (d, 1H). IR (KBr): 888, 1061, 1262, 1507, 1691 cm$^{-1}$.

81.c. 2-chloro-6,7-difluoro-3-quinolylmethanol

A suspension of the product of Stage 81.b (9 g; 39 mmol) in methanol (400 ml) is treated with sodium borohydride (2 g; 53 mmol) at ambient temperature for half an hour. The excess borohydride is destroyed with acetic acid (2 ml). The volatile substances are eliminated under reduced pressure. The residue is dissolved in ethyl acetate (500 ml), the mixture obtained then being washed successively with a dilute solution of sodium bicarbonate, water and saturated salt water, followed by drying over magnesium sulphate and concentration under reduced pressure. The residue is recrystallized from 1,2-dichloroethane in order to produce the product in the title (8 g; 80% yield) in the form of a beige solid (M.p. 166.5–167° C.).

NMR IH (DMSO): 4.67 (d, 2H); 5.80 (t, 1H); 8.01 (dd, 1H); 8.22 (dd, 1H); 8.48 (s, 1H). IR (KBr): 871, 1038, 1253,1513 cm$^{-1}$.

81.d. (+)-8-(2-chloro-6,7-difluoro-3-quinolinemethanol)-5-ethyl-5-hydroxy-1,3,4,5,8,9-hexahydrooxepino[3,4-c]pyridine-3,9-dione:

Diethylazodicarboxylate (1.24 ml; 7.87 mmol) is added dropwise at ambient temperature and under an argon atmosphere to a solution in anhydrous DMF (30 ml) of (+)-EHHOPD (1.58 g; 7.08 mmol; Stage 80.c.), the product of Stage 81.c (1.62 g; 7.06 mmol) and tributylphosphine (1.91 ml; 7.87 mmol). The mixture thus obtained is then agitated for 16 hours. The reaction medium is then evaporated to dryness under reduced pressure. The residue is purified by chromatography on a silica column (eluant: ethyl acetate). The solid obtained is taken up in diethylether, filtered and dried in order to produce the product in the title (1.56 g; 51% yield) in the form of a whitish solid (M.p. 196° C.).

NMR $^1$H (DMSO): 0.84 (t, 3H); 1.74 (m, 2H); 3.02 (d, 1H); 3.34 (d, 1H);5.29 (s, 2H); 5.31 (dd, 2H); 5.75 (s, 1H); 6.51 (d, 1H); 7.80 (d, 1H); 8.03 (dd, 1H); 8.07 (s, 1H); 8.17 (dd, 1H). IR (KBr): 875,1057, 1360, 1507, 1574, 1647, 1749 cm$^{-1}$.

81.e. (+)-5-ethyl-9,10-difluoro-5-hydroxy-4,5,13,15-tetrahydro-1H,3H-oxepino[3',4':6,7]indolizino[1,2-b]quinoline-3,15-dione:

A mixture of the product of Stage 81.d (1.53 g; 3.52 mmol; Stage 2.d.), tetrabutylammonium bromide (1.25 g; 3.87 mmol), potassium acetate (520 mg; 5.28 mmol), triphenylphosphine (180 mg; 0.70 mmol) and palladium (II) acetate (79 mg; 0,35 mmol) is agitated under an argon atmosphere in anhydrous acetonitrile heated at reflux for 22 hours. After the reaction medium has returned to ambient temperature, concentration under reduced pressure is carried out before chromatography on a silica column (eluant: CH$_2$Cl$_2$/MeOH mixture 98/2). The product in the title is then obtained (960 mg; yield 68%; purity determined by HPLC: 97.1%). This product is taken up in anhydrous CH$_2$Cl$_2$ (100 ml) and agitation is carried out for 24 hours, followed by filtering and drying under reduced pressure in order to produce the purified product of the title (850 mg; yield 61%; purity determined by HPLC: 99.6%) in the form of a white solid.

NMR $^1$H (DMSO): 0.87 (t, 3H); 1.85 (m, 2H); 3.08 (d, 1H); 3.44 (d, 1H); 5.26 (s, 2H); 5.39 (d, 2H); 5.52 (d, 2H); 5.99 (wide peak, 1H); 7.39 (s, 1H); 8.15 (dd, 1H); 8.23 (dd, 1H); 8.68 (s, 1H). IR (KBr): 871, 1261, 1512, 1579, 1654, 1746 cm$^{-1}$.

Example 82

(+)-1-[9-chloro-5-ethyl-5-hydroxy-10-methyl-3,15-dioxo-4,5,13,15-tetrahydro-1H,3H-oxepino[3',4':6,7]indolizino[1,2-b]quinolin-12-ylmethyl]-4-methyl-hexahydropyridinium chloride

82.a. 1-(2-amino-4-chloro-5-methylphenyl)-2-chloro-ethanone 3-chloro-4-methylaniline (44.4 ml; 0.366 mol) in 1,2-dichloroethane (440 ml), under an argon atmosphere, is cooled down in an ice bath. The following are added dropwise and in the order of this mixture: boron trichloride (1M in heptane; 400 ml; 0.4 mol), chloroacetonitrile (28 ml; 0.44 mol) and diethylaluminium chloride (1M in heptane; 400 ml; 0.4 mol). For the addition, the temperature is maintained below 20° C. The resultant mixture is then heated at reflux for 3 hours, then cooled down to 10° C. The hydrolysis of the reaction medium is then carried out cautiously using 2N hydrochloric acid (240 ml) and it is heated at reflux for 1 hour. Water (1 l) and ethyl acetate (1 l) are added, the mixture obtained is agitated for 15 minutes before separating the phases. The aqueous phase is again extracted with ethyl acetate (200 ml), and the combined organic phases are washed with water (500 ml). After drying over magnesium sulphate the organic phase is concentrated. The residue is taken up in petroleum ether (fraction having a boiling point of 45 to 60° C.; 150 ml) and the mixture thus obtained is left for 16 hours at 4° C. The resultant precipitate is collected by filtration, washed with petroleum ether and dried under reduced pressure in order to produce the product in the title (25 g; 31% yield). M.p. 129–130° C.

NMR $^1$H (DMSO): 2.20 (s, 3H); 4.98 (s, 2H); 6.90 (s, 1H); 7.15 (wide peak, 2H); 7.70 (s, 1H). IR (KBr): 871, 1018, 1183, 1225, 1270, 1533,1577, 1619, 1662 cm$^{-1}$.

82.b. Ethyl 7-chloro-4-chloromethyl-6-methyl-2-oxo-1,2-dihydro-3-quinolinecarboxylate The product of Stage 82.a (25 g; 0.11 mol) and triethylamine (30.6 ml; 0.22 mol) are mixed together in acetonitrile (520 ml). Ethylmalonyl chloride (28.1 ml; 0.22 mol) is added at ambient temperature and under an argon atmosphere. The mixture obtained is agitated for 3 hours. Sodium ethanolate (prepared by the dissolution of 3 g, i.e. 0.13 mol, of sodium in 140 ml of absolute ethanol) is then added dropwise and the resultant mixture is agitated at ambient temperature for 16 hours. The precipitate is collected by filtration, washed successively with ethanol, water, ethanol and ether. It is then dried under reduced pressure at 70° C. over phosphorus pentoxide in order to produce the product in the title (28.6 g; 83% yield) in the form of a whitish powder.

NMR $^1$H (DMSO): 1.30 (t, 3H); 2.40 (s, 3H); 4.35 (q, 2H); 4.85 (s, 2H); 7.41 (s, 1H); 7.91 (s, 1H); 12.15 (wide peak, 1H). IR (KBr): 879,1108, 1250, 1288, 1483, 1664, 1721 cm$^{-1}$.

82.c. Ethyl 2,7-dichloro-4-chloromethyl-6-methyl-3-quinolinecarboxylate

The product of Stage 82.b (28.4 g; 90 mmol) is heated for 4 hours at reflux in phosphorus oxychloride (400 ml). The mixture obtained is concentrated under reduced pressure (20 mm Hg) at 80° C. The residue is taken up in diisopropylether (400 ml). The resultant precipitate is collected by filtration, washed with ether and petroleum ether, then dried under reduced pressure in order to produce the product in the title (25.4 g; 85% yield) in the form of a whitish powder (M.p. 126–127° C.).

NMR $^1$H (DMSO): 1.37 (t, 3H); 2.58 (s, 3H); 4.49 (q, 2H); 5.14 (s, 2H); 8.16 (s, 1H); 8.35 (s, 1H). IR (KBr): 874, 1006, 1163, 1243, 1278, 1577, 1723 cm$^{-1}$.

82.d. 2,7-dichloro-4-chloromethyl-6-methyl-3-quinolylmethanol

The product of Stage 82.c (25.2 g; 76.5 mmol) is mixed under an argon atmosphere with dichloroethane (630 ml). Diisobutylaluminium hydride (1M in dichloromethane; 307 ml; 307 mmol) is added dropwise while the reaction mixture is agitated and the temperature is maintained below 20° C. The reaction mixture is then agitated at ambient temperature for 3 hours, then poured into an aqueous solution of potassium tartrate (concentrated to 20% by weight; 1.5 l). The emulsion thus obtained is agitated vigorously for 1 hour, filtered on celite and the two phases are then separated. The aqueous phase is extracted with ethyl acetate (200 ml) and the combined organic phases are washed with an aqueous solution of sodium chloride (concentrated to 20% by weight; 500 ml). The organic phase obtained is dried over magnesium sulphate, filtered and concentrated under reduced pressure. The residue is taken up in diethylether (50 ml) and the resultant precipitate is collected by filtration. By drying under reduced pressure, the product in the title is obtained (18.3 g; 93% yield) in the form of a whitish powder (M.p. 169–170° C.).

NMR $^1$H (DMSO): 2.57 (t, 3H); 4.84 (s, 2H); 5.36 (s, 2H); 8.06 (s, 1H); 8.27 (s, 1H). IR (KBr): 870, 1022, 1102, 1304, 1482, 1567 cm$^{-1}$.

82.e. 2,7-dichloro-6-methyl-4-(4-methylpiperidinomethyl)-3-quinolylmethanol

A solution of the product of Stage 82.d (16.2 g; 55.7 mmol) in THF (70 ml) is treated with a solution of 4-methylpiperidine (23 ml; 195 mmol). The mixture obtained is agitated at ambient temperature for 2 hours. Water (200 ml) and dichloroethane (200 ml) are added. The organic phase is washed with an aqueous solution of sodium chloride (concentrated to 20% by weight; 100 ml), dried over magnesium sulphate and concentrated under reduced pressure. By crystallization of the residue from diethylether, the product in the title is obtained (18.3 g; 93% yield) in the form of a white crystalline solid (M.p. 170–171.5° C.).

NMR $^1$H (CDCl$_3$): 0.88 (d, 3H); 1.17 (m, 2H); 1.42 (m, 1H); 1.60 (m, 2H); 2.19 (t, 2H); 2.56 (s, 3H); 2.82 (d, 2H); 4.02 (s, 2H); 4.93 (s, 2H); 6.36 (wide peak, 1H); 7.95 (s, 1H); 8.02 (s, 1H). IR (KBr): 971, 1013, 1105, 1293, 1479, 1559 cm$^{-1}$.

82.f. (+)-8-[2,7-dichloro-6-methyl-4-(4-methylpiperidinomethyl)-3-quinolylmethyl]-5-ethyl-5-hydroxy-1,3,4,5,8,9-hexahydrooxepino[3,4-c]pyridine-3,9-dione A suspension of (+)-EHHOPD (obtained in Stage 80.c.; 1.56 g; 7.0 mmol) in anhydrous dioxane (70 ml) is treated successively, under an argon atmosphere, with the product of Stage 82.e (2.47 g; 7.0 mmol), triphenylphosphine (2.02 g; 7.7 mmol) and diisopropyl azodicarboxylate (1.07 ml; 10.5 mmol). The mixture is agitated at ambient temperature for 16 hours. The volatile substances are then evaporated off under reduced pressure. The residue is purified by chromatography on a silica column (eluant: ethyl acetate). The solid obtained is taken up in diethylether, filtered and dried in order to produce the product in the title (1.96 g; 50% yield) in the form of a whitish solid (M.p. 182° C.).

NMR $^1$H (DMSO): 0.89 (m, 8H); 1.23 (m, 1H); 1.41 (t, 2H); 1.64 (m, 2H); 2.09 (q, 2H); 2.59 (m, 5H); 3.15 (dd, 2H); 4.06 (dd, 2H); 5.31 (dd, 2H); 5.35 (dd, 2H); 5.75 (s, 1H); 6.29 (d, 1H); 7.17 (d, 1H); 8.06 (s, 1H); 8.46 (s, 1H). IR (KBr): 878, 1053, 1275, 1474, 1572, 1648, 1747 cm$^{-1}$.

82.g. (+)-9-chloro-5-ethyl-5-hydroxy-10-methyl-12-(4-methylpiperidinomethyl)-4,5,13,15-tetrahydro-1H,3H-oxepino[3',4':6,7]indolizino[1,2-c]quinoline-3,15-dione A mixture of the product of Stage 82.f (3.80 g; 6.80 mmol), tetrabutylammonium bromide (2.42 g; 7.5 mmol), potassium acetate (1.00 g; 10.2 mmol), triphenylphosphine (890 mg; 3.4 mmol) and palladium (II) acetate (220 mg; 0.68 mmol) is agitated under an argon atmosphere in anhydrous acetonitrile (85 mg) at reflux for 24 hours. After cooling down to ambient temperature, the resultant precipitate is collected by filtration and washed successively with acetonitrile, water, acetone and diethylether in order to produce, after drying under reduced pressure, the product in the title (2.5 g; 70% yield) in the form of a whitish powder.

NMR $^1$H (DMSO): 0.86 (m, 6H); 1.12 (q, 2H); 1.36 (m, 1H); 1.56 (d, 2H); 1.84 (q, 2H); 2.12 (t, 2H); 2.56 (s, 3H); 2.83 (dd, 2H); 3.26 (dd, 2H); 4.03 (dd, 2H); 5.28 (dd, 2H); 5.45 (dd, 2H); 6.04 (s, 1H); 7.34 (s, 1H); 8.14 (s, 1H); 8.38 (s, 1H). IR (KBr): 870, 1058, 1208, 1280, 1477, 1593, 1655, 1749 cm$^{-1}$.

82.h. (+) 1-[(5R)-9-chloro-5-ethyl-5-hydroxy-10-methyl-3,15-dioxo-4,5,13,15-tetrahydro-1H,3H-oxepino[3',4':6,7]indolizino[1,2-c]quinolin-12-ylmethyl]-4-methyl-hexahydropyridinium chloride A mixture of the product of Stage 82.g (2.3 g; 7.7 mmol) and absolute ethanol (300 ml) is subjected to ultrasound for 2 minutes. The milky suspension obtained is agitated and treated with hydrochloric acid (1N solution; 13.2 ml; 13.2 mmol) in order to produce a light yellow solution which, at rest, forms a gel-type precipitate. The precipitate is collected by filtration on a BŸchner and washed successively with ethanol and ether, then dried under reduced pressure in order to produce the product in the title (2.1 g; 85% yield).

NMR $^1$H (DMSO): 0.87 (m, 6H); 1.59 (m, 5H); 1.84 (q, 2H); 2.64 (s, 3H); 3.28 (dd, 2H); 3.45 (s, 2H); 4.93 (s, 2H); 5.47 (dd, 2H); 5.61 (s, 2H); 6.04 (wide peak, 1H); 7.41 (s, 1H); 8.28 (s, 1H); 8.63 (s, 1H); 10.30 (wide peak, 1H). IR (KBr): 1043, 1212, 1479, 1585, 1655, 1751 cm$^{-1}$.

Pharmacological Study of the Products According to the Invention

1. Relaxation Activity Test of DNA Induced by Topoisomerase 1.

All the reactions are carried out in a 20 μl reaction buffer constituted by 50 mM of Tris-HCl (pH 7.5), 50 mM of KCl, 0.5 mM of dithiothreitol, 10 mM of MgCl$_2$, 0.1 mM of ethyldiamine tetraacetic acid (EDTA), 30 μg/ml of bovine serum albumin and 300 ng of supercoiled pUC19 (Pharmacia Biotech, Orsay, France) with or without the compounds to be tested at defined concentrations. All the compounds to be tested are initially dissolved in dimethylsulphoxide (DMSO) at 50 mM, the other dilutions being carried out with distilled water. The final concentration of DMSO does not exceed 1% (v/v). The reaction is initiated by the addition of a unit of DNA topoisomerase 1 of purified calf thymus (Gibco-BRL, Paisley, United Kingdom) and is carried out for 15 minutes at 37° C. The reactions are stopped by the addition of 3 μl of a mixture containing 1% dodecyl sodium sulphate at 1%, 20 mM of EDTA and 500 μg/ml of K proteinase (Boehringer Mannheim, Meylan, France). After an additional incubation period of 30 minutes at 37° C., 2 μl of a loading buffer containing 10 mM of Na$_2$HPO$_4$, 0.3% of bromophenol blue et 16% Ficoll are added to samples which are subjected to electrophoresis in agarose gels at 1.2% at 1 V/cm for 20 hours in a buffer containing 36 mM of Tris-HCl at pH 7.8, 30 mM of Na$_2$HPO$_4$, 1 mM of EDTA and 2 μg/ml of chloroquine. The gels are stained with 2 μg/ml of ethidium bromide, photographed under UV light at 312 nm with a camera and the fluorescent intensity is measured with a bioProfil camera (Vilber Lourmat, Lyon, France) with a view to determining the percentage of relaxed DNA. Each experiment is carried out at least three times in duplicate.

In each experiment, the supercoiled plasmid DNA is incubated alone or with topoisomerase 1. The reaction is completed within 15 minutes. For each compound to be tested or control, the supercoiled plasmid DNA is incubated in the presence of 500 μM of compound to be tested with enzyme or without enzyme plus the compound to be tested, at concentrations of 10 μM, 100 μM, 200 μM and 500 μM. As indicated in Table I, Examples 2 to 4, 9 to 11 and 76 to 79 inhibit the relaxation activity encouraged by topoisomerase 1 in a dose-dependent manner.

TABLE I

| | PERCENTAGE OF RELAXED DNA | | | |
|---|---|---|---|---|
| | CONCENTRATION (μM) | | | |
| EXAMPLE | 10 | 100 | 200 | 500 |
| Example 2 | 97.9 | 78.3 | 73.2 | 51.1 |
| Example 3 | 79.9 | 59.9 | 55.0 | 45.7 |
| Example 4 | 99.1 | 82.2 | 67.6 | 32.9 |
| Example 9 | 77.1 | 33.9 | 29.7 | 20.4 |
| Example 10 | 96.9 | 45.4 | 26.2 | 8.7 |
| Example 11 | 65.0 | 50.3 | 39.8 | 31.0 |
| Example 76 | 79.7 | 33.5 | 23.2 | — |
| Example 77 | 86.2 | 35.1 | 32.1 | — |
| Example 78 | 56.2 | 28.0 | 24.2 | — |
| Example 79 | 55.6 | 38.9 | 30.0 | — |

2. Test on Cell Proliferation a. Eight tumoral cell lines are used in this study: L1210 (mouse lymphocytic leukemia), HCT15 and LOVO (cell lines of human colon adenocarcinoma), A549 (human lung carcinoma), A172, U373 et U87 (human glioblastoma). All these lines are obtained from the American Type Culture Collection (ATCC), Rockville, Md. The L1210 cell cultures in suspension are cultured in Dulbecco's modified Eagle's medium (DMEM) (BioWhitaker, Verviers, Belgium) together with 10% of foetal calf serum inactivated by heating, 2 mM of glutamine, 50 U/ml of penicillin and 50 μg/ml of streptomycin. The HT29 cells are cultured in mono-layer cultures in a McCoy 5a medium (Gibco, Paisley, United Kingdom) together with 10% of foetal calf serum inactivated by beat plus 2 mM of glutamine and 50 μg/lm of gentamycin. The other cells are cultured in an Earle's modified essential medium (EMEM; Gibco, Paisley, United Kingdom) together with 5% foetal calf serum inactivated by heat, 2 mnM of glutamine, 50 U/ml of penicillin and 50 μg/ml of streptomycin. All the cell lines are cultured at 37° C. in a humidified atmosphere containing 95% air and 5% CO$_2$.

Inhibition of the tumor cell line proliferation is determined using an MTT test. 1500 L1210 cells in a culture medium (according to the needs of the cell medium) are seeded in a well of a micro-well plate (tissue culture level: 96 wells, flat bottom) 24 hours before treatment with the compounds to be tested. For these dose-response studies, the cells are incubated with each of the compounds to be tested or their corresponding solvent (controls) for 48 hours over a final concentration range of $1.10^{-10}$ to $1.10^{-4}$ M. All the compounds are dissolved just before use in dimethylsulphoxide (DMSO) at a concentration of 50 mM. Other dilutions of the medicaments are carried out in the culture medium. The final concentration of DMSO never exceeds 0.2% (v/v). As controls, the solutions of medicaments are replaced with the solvent which is diluted successively in the same way as the compounds to be tested.

After the incubation period, the labeling reagent MTT (3-[4,5-dimethylthiazol-2-yl]-2,5-diphenyltetrazolium bromide; Thiazol blue, Sigma M 565, Sigma, St Louis, Mo.) is added at a final concentration of 0.3 mg/ml to each well. The cells are incubated for 4 hours at 37° C. in a humidified atmosphere. This stage allows the mitochondrial dehydrogenase of the living cells to convert the yellow tetrazolium salt MTT into crimson formazan crystals. The supernatant part is eliminated and the formazan crystals formed are solubilized with DMSO. The resultant coloured solution is quantified by absorbance at 570 nm by using a multi-cuvette scanning spectrophotometer. The data concerning the proliferation is expressed as a percentage of living cells in the treated wells, divided by the living cells in the controls. Each point represents the average of three independent experiments, each experiment represents six determinations.

For the other cell lines (HCT15, LOVO, A549, A172, U373, U87), 1000 to 2000 cells are seeded in the well of a micro-well plate 24 hours before medicinal treatment. They are incubated with each of the compounds to be tested or their corresponding solvent (controls) for 72 hours over a final concentration range of $1.10^{-10}$ to $1.10^{-6}$ M.

The results are expressed as percentages of the calculated proliferation by the optical density (OD) of the cells treated with a medicament divided by the OD of the control cells (cells treated with DMSO). As represented in Table II, the compounds to be tested have inhibited the proliferation of cells in a dose-dependent manner.

TABLE II

PERCENTAGE OF CELL PROLIFERATION

| Cell line | CONCENTRATION (nM) | | | | | | |
|---|---|---|---|---|---|---|---|
| | 0.1 | 1 | 10 | 100 | 1 000 | 10 000 | 100 000 |
| Example 3 | | | | | | | |
| L1210 | 87.22 | 68.92 | 42.64 | 26.85 | 10.83 | 2.11 | 2.20 |
| HCT15 | 86.00 | 84.00 | 58.00 | 44.00 | 18.00 | 9.00 | 13.00 |
| LOVO | 108.00 | 86.00 | 54.00 | 31.00 | 23.00 | 10.00 | 12.00 |
| A549 | 132.00 | 111.00 | 75.00 | 39.00 | 35.00 | 10.00 | 11.00 |
| A172 | 89.00 | 101.00 | 68.00 | 37.00 | 27.00 | 10.00 | 7.00 |
| U373 | 99.00 | 98.00 | 40.00 | 24.00 | 17.00 | 13.00 | 9.00 |
| U87 | 108.00 | 85.00 | 42.00 | 23.00 | 15.00 | 5.00 | 6.00 |
| Example 4 | | | | | | | |
| L1210 | 92.14 | 97.14 | 91.08 | 86.28 | 46.79 | 27.80 | 8.09 |
| HCT15 | 91.00 | 92.00 | 86.00 | 78.00 | 54.00 | 20.00 | 7.00 |
| LOVO | 80.00 | 75.00 | 79.00 | 69.00 | 38.00 | 21.00 | 5.00 |
| A549 | 71.00 | 76.00 | 71.00 | 56.00 | 36.00 | 22.00 | 12.00 |
| A172 | 93.00 | 92.00 | 98.00 | 97.00 | 44.00 | 31.00 | 10.00 |
| U373 | 86.00 | 85.00 | 89.00 | 63.00 | 30.00 | 16.00 | 2.00 |
| U87 | 98.00 | 101.00 | 98.00 | 74.00 | 11.00 | 6.00 | 2.00 |
| Example 9 | | | | | | | |
| L1210 | 74.04 | 62.05 | 44.72 | 34.01 | 20.20 | 4.34 | 1.58 |
| HCT15 | 94.00 | 89.00 | 59.00 | 35.00 | 15.00 | 8.00 | 3.00 |
| LOVO | 74.00 | 85.00 | 44.00 | 31.00 | 21.00 | 4.00 | 2.00 |
| A549 | 91.00 | 88.00 | 50.00 | 31.00 | 23.00 | 5.00 | 3.00 |
| A172 | 97.00 | 89.00 | 44.00 | 36.00 | 19.00 | 3.00 | 1.00 |
| U373 | 89.00 | 69.00 | 24.00 | 18.00 | 8.00 | 3.00 | 1.00 |
| U87 | 105.00 | 72.00 | 14.00 | 7.00. | 4.00 | 2.00 | 6.00 |
| Example 10 | | | | | | | |
| L1210 | 91.51 | 97.94 | 89.28 | 67.32 | 31.51 | 19.78 | 3.65 |
| HCT15 | 111.00 | 87.00 | 103.00 | 63.00 | 42.00 | 17.00 | 9.00 |
| LOVO | 71.00 | 76.00 | 77.00 | 52.00 | 29.00 | 18.00 | 4.00 |
| A549 | 71.00 | 76.00 | 71.00 | 56.00 | 36.00 | 22.00 | 7.00 |
| A172 | 93.00 | 92.00 | 91.00 | 60.00 | 39.00 | 15.00 | 3.00 |
| U373 | 96.00 | 104.00 | 87.00 | 35.00 | 20.00 | 10.00 | 2.00 |
| U87 | 96.00 | 79.00 | 89.00 | 17.00 | 6.00 | 5.00 | 2.00 |
| Example 11 | | | | | | | |
| L1210 | 91.99 | 81.37 | 23.16 | 16.83 | 5.59 | 1.45 | 1.04 |
| HCT15 | 71.00 | 63.00 | 45.00 | 23.00 | 12.00 | 9.00 | 9.00 |
| LOVO | 66.00 | 42.00 | 29.00 | 21.00 | 8.00 | 3.00 | 3.00 |
| A549 | 82.00 | 44.00 | 29.00 | 26.00 | 4.00 | 3.00 | 2.00 |
| A172 | 95.00 | 53.00 | 47.00 | 39.00 | 12.00 | 3.00 | 2.00 |
| U373 | 50.00 | 30.00 | 25.00 | 8.00 | 2.00 | 1.00 | 2.00 |
| U87 | 40.00 | 21.00 | 12.00 | 6.00 | 1.00 | 1.00 | 1.00 | b. Nine tumoral cell lines are used in this study: PC3, DU145 (human prostate cell lines), MCF7 and MCF7-ADR (mammary cell lines, the symbol "ADR" is used to indicate that the line has been rendered adriamycin-resistant), A427 (human lung adenocarcinoma), HT29 (human colon adenocarcinoma cell line), T24s, T24r (human bladder cell line, the T24r's are resistant to adriamycin, amongst others). The PC3, DU145 and A427 lines were obtained from the American Type Culture Collection (ATCC, Rockville, Md). The MCF7 and MCF7-ADR cells were graciously donated by Dr Jacques Soudon (Pharmacell, Paris, France). The T24s and T24r cells were graciously donated by Dr Robert Kiss (Free University of Brussels, Belgium). The HT29 cells were cultivated in single-layer cultures in a 4.5 g/l DMEM medium (Gibco, Paisley, United Kingdom) completed with 10% heat-inactivated foetal calf serum plus 2 mM glutamine and 50 g/ml gentamycin (Gibco, Paisley, United Kingdom). The other cells are cultivated in a Earle's modified essential medium DMEM at 4.5 g/l (Gibco, Paisley, United Kingdom) completed with 10% heat-inactivated foetal calf serum, 2 mM glutamin (Gibco, Paisley, United Kingdom), 50 U/ml penicillin and 50 g/ml streptomycin (BioWhitaker, Verviers, Belgium). All the cell lines are cultivated at 37° C. in a humidified atmosphere containing 95% air and 5% $CO_2$.

Inhibition of the tumour cell line proliferation is determined using a WST1 colorimetry test. 500 to 4000 cells in a culture medium (according to the needs of the cell medium) are seeded in a well of a micro-well plate (96 wells, flat bottom) 24 hours before treatment with the compounds to be tested. For these concentration-response studies, the cells are incubated with each of the compounds to be tested or their corresponding solvent (controls) for 72 hours over a final concentration range of 1×10−13 to 1×10−5 M. All the compounds are dissolved in dimethylsulphoxide (DMSO) or in water for the water-soluble compounds. The following dilutions of the compounds of the present invention are carried out in the culture medium such that the final concentration of DMSO, when it is part of the vehicle's composition, is always 0.1% (v/v). As controls, the solutions of the compounds are replaced with the solvent which is diluted successively in the same way as the compounds to be tested.

After incubation, the labelling reagent WST1 (4-[3-(4-iodophenyl)-2-(4-nitrophenyl)-2h-5-tetrazolio-1,3-benzene) (Boehringer Mannheim, Germany) is added at a final concentration of 9% to each well. The cells are incubated for 2 to 4 hours at 37° C. in a humidified atmosphere. This stage allows the mitochondrial dehydrogenase of the living cells to convert the orange tetrazolium salt WST1 into crimson formazan crystals. The resultant coloured solution is quantified by a dual beam reading (450 and 690 nm) using a multi-cuvette scanning spectrophotometer.

The results are expressed in the form of a concentration table, expressed in mol/liter, including the 50% inhibitory concentration ($IC_{50}$). They are shown in Tables III A) and III B). Examples where the number is followed by an "s" correspond to the compound salts. Cpt, Adr and Tpt are the abbreviations respectively for camptothecin, adriamycin and topotecan.

TABLE III A)

| Examples | PC3 | DU145 | A427 | HT29 |
|---|---|---|---|---|
| Cpt | 10-7 to 10-8 | 10-7 to 10-8 | 10-8 to 10-7 | 10-7 to 10-8 |
| Adr | 10-7 to 10-8 | | | |
| Tpt | 10-6 to 10-7 | 10-7 to 10-8 | 10-7 to 10-8 | 10-7 to 10-8 |

TABLE III A)-continued

| Examples | PC3 | DU145 | A427 | HT29 |
|---|---|---|---|---|
| 3 | 10-7 to 10-8 | 10-8 to 10-9 | 10-9 to 10-8 | 10-7 to 10-8 |
| 16 | <10-13 | 10-10 to 10-9 | 10-13 to 10-12 | 10-8 to 10-9 |
| 17 | 10-8 to 10-9 | 10-12 to 10-11 | 10-11 to 10-10 | 10-8 to 10-9 |
| 18 | 10-13 to 10-12 | 10-9 to 10-10 | 10-11 to 10-10 | 10-8 to 10-9 |
| 19 | 10-8 to 10-9 | 10-9 to 10-10 | 10-10 to 10-9 | 10-8 to 10-9 |
| 20 | <10-13 | 10-10 to 10-11 | 10-13 to 10-11 | 10-8 to 10-9 |
| 21 | 10-8 to 10-9 | 10-8 to 10-9 | 10-11 to 10-10 | 10-7 to 10-8 |
| 22 | 10-7 to 10-8 | 10-8 to 10-9 | 10-9 to 10-8 | 10-7 to 10-8 |
| 23 | <10-13 | 10-10 to 10-11 | 10-12 to 10-13 | 10-8 to 10-9 |
| 24 | 10-10 to 10-11 | 10-8 to 10-9 | 10-9 to 10-8 | 10-7 to 10-8 |
| 25 | 10-9 to 10-8 | 10-9 to 10-10 | 10-10 to 10-9 | 10-8 to 10-9 |
| 26 | 10-8 to 10-9 | 10-9 to 10-10 | 10-10 to 10-9 | 10-10 to 10-11 |
| 28 | 10-8 to 10-9 | 10-10 to 10-11 | 10-10 to 10-9 | 10-8 to 10-7 |
| 29 | 10-13 to 10-12 | 10-9 to 10-10 | 10-11 to 10-10 | 10-8 to 10-9 |
| 34 | 10-9 to 10-10 | 10-8 to 10-9 | 10-9 to 10-8 | 10-7 to 10-8 |
| 37 | 10-7 to 10-8 | 10-8 to 10-9 | 10-9 to 10-8 | 10-7 to 10-8 |
| 38 | 10-7 to 10-8 | 10-8 to 10-9 | 10-9 to 10-8 | 10-7 to 10-8 |
| 39 | 10-7 to 10-8 | 10-7 to 10-8 | 10-9 to 10-8 | 10-8 to 10-9 |
| 39s | 10-7 to 10-8 | 10-8 to 10-9 | 10-9 to 10-8 | 10-7 to 10-8 |
| 42 | 10-7 to 10-8 | 10-8 to 10-9 | 10-9 to 10-8 | 10-8 to 10-9 |
| 44s | 10-8 to 10-7 | | 10-8 to 10-7 | 10-7 to 10-8 |
| 49 | 10-7 to 10-8 | 10-8 to 10-9 | 10-11 to 10-10 | 10-8 to 10-9 |
| 50 | 10-8 to 10-7 | 10-10 to 10-11 | 10-8 to 10-7 | 10-7 to 10-8 |
| 53 | 10-7 to 10-8 | 10-8 to 10-9 | 10-9 to 10-8 | 10-7 to 10-8 |
| 54 | 10-7 to 10-8 | 10-8 to 10-9 | 10-8 to 10-7 | 10-7 to 10-8 |
| 57 | | 10-9 to 10-10 | 10-9 to 10-8 | 10-7 to 10-8 |
| 57s | 10-7 to 10-8 | | 10-8 to 10-7 | 10-8 to 10-7 |
| 58 | 10-7 to 10-8 | 10-9 to 10-10 | 10-8 to 10-9 | 10-7 to 10-8 |
| 58s | 10-7 to 10-8 | 10-9 to 10-10 | 10-9 to 10-8 | 10-8 to 10-9 |
| 59 | 10-7 to 10-8 | 10-8 to 10-9 | 10-8 to 10-7 | 10-7 to 10-8 |
| 59s | 10-8 to 10-7 | | 10-9 to 10-8 | 10-8 to 10-9 |
| 60 | 10-7 to 10-8 | 10-9 to 10-10 | 10-9 to 10-10 | 10-8 to 10-9 |
| 63 | 10-7 to 10-8 | 10-8 to 10-9 | 10-9 to 10-8 | 10-7 to 10-8 |
| 63s | 10-8 to 10-7 | | 10-8 to 10-7 | 10-8 to 10-7 |
| 64 | 10-7 to 10-8 | 10-10 to 10-11 | 10-9 to 10-8 | 10-8 to 10-9 |
| 65 | 10-8 to 10-7 | | 10-8 to 10-7 | 10-7 to 10-8 |
| 67 | | 10-8 to 10-9 | 10-9 to 10-8 | 10-7 to 10-8 |
| 81 | 10-8 | 10-9 | | |
| 82 | 3.10-8 | 7.10-9 | | |

TABLE III B)

| Examples | MCF7 | MCF7-ADR | T24S | T24R |
|---|---|---|---|---|
| Cpt | 10-6 to 10-7 | 10-8 to 10-9 | | |
| Adr | 10-5 to 10-6 | >10-4 | | |
| Tpt | 10-5 to 10-6 | 10-5 to 10-6 | | |
| 3 | 10-6 to 10-7 | 10-7 to 10-8 | | |
| 12 | 10-6 to 10-7 | 10-7 to 10-8 | | |
| 16 | 10-7 to 10-8 | 10-8 to 10-9 | | |
| 17 | 10-7 to 10-8 | 10-13 to 10-12 | | |
| 18 | 10-7 to 10-8 | 10-8 to 10-9 | | |
| 19 | 10-7 to 10-8 | 10-9 to 10-10 | | |
| 22 | 10-6 to 10-7 | 10-8 to 10-9 | | |
| 23 | 10-7 to 10-8 | 10-9 to 10-10 | | |
| 25 | 10-6 to 10-7 | 10-8 to 10-9 | | |
| 26 | 10-6 to 10-7 | 10-8 to 10-9 | | |
| 28 | 10-7 to 10-8 | 10-8 to 10-9 | | |
| 39s | 10-6 to 10-7 | | 10-8 to 10-9 | 10-7 to 10-8 |
| 42 | 10-6 to 10-7 | 10-8 to 10-9 | | |
| 43 | | | <10-13 | 10-7 to 10-8 |
| 44 | | | 10-7 to 10-8 | 10-7 to 10-8 |
| 44s | | | 10-8 to 10-9 | 10-8 to 10-9 |
| 45 | | | 10-8 to 10-9 | 10-7 to 10-8 |
| 45s | | | 10-13 to 10-12 | 10-7 to 10-8 |
| 49s | | | 10-8 to 10-9 | 10-7 to 10-8 |
| 57 | 10-6 to 10-7 | | | |
| 57s | | | 10-10 to 10-9 | 10-8 to 10-9 |
| 59 | 10-6 to 10-7 | | | |
| 59s | | | 10-10 to 10-9 | 10-8 to 10-9 |
| 61 | | | 10-7 to 10-8 | 10-6 to 10-7 |
| 63s | | | 10-9 to 10-10 | 10-7 to 10-8 |

TABLE III B)-continued

| Examples | MCF7 | MCF7-ADR | T24S | T24R |
|---|---|---|---|---|
| 65 | | | 10-8 to 10-9 | 10-7 to 10-8 |
| 67 | 10-6 to 10-7 | | | |
| 71 | 10-6 to 10-7 | | 10-7 to 10-8 | 10-7 to 10-8 |

What is claimed is:

1. A compound selected from the group consisting of racemic or enantiomeric forms or mixtures thereof of a compound of the formula (HCPT)

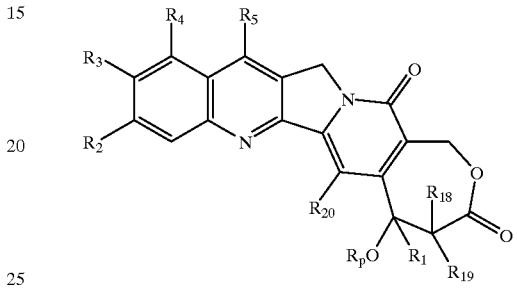

wherein $R_1$ is selected from the group consisting of lower alkyl, lower alkenyl, lower alkynyl, lower haloalkyl, lower alkoxy lower alkyl and lower alkylthio lower alkyl, $R_2$, $R_3$ and $R_4$ are independently selected from the group consisting of hydrogen, halogen, lower alkyl, lower haloalkyl, lower alkenyl, —CN, lower cyanoalkyl, —NO$_2$, lower nitroalkyl, amido, lower amidoalkyl, hydrazino, lower hydrazinoalkyl, azido, lower azidoalkyl,

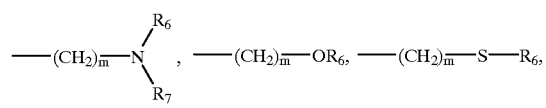

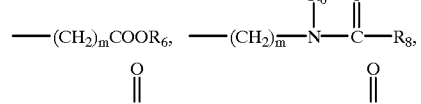

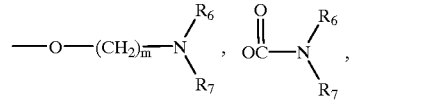

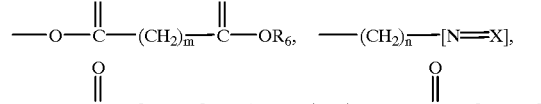

[N═X] is a heterocyclic of 4 to 7 ring members with N and X are the remaining ring members selected from the group consisting of oxygen, sulfur, —CH$_2$, —CH═, ═N—, —NR$_9$—, —COR$_{10}$—, unsubstituted or substituted aryl and unsubstituted or substituted aralkyl with 1 to 4 substituents on the aryl selected from the group consisting of lower alkyl, halogen, —NO$_2$, —NH$_2$, lower alkylamino, lower haloalkyl, lower hydroxyalkyl, lower alkoxy and lower alkoxy lower alkyl or $R_2$ and $R_3$ or $R_3$ and $R_4$ together form a chain of 3 to 4 members selected from the group consisting of —CH═, —CH$_2$—, —O—, —S—, ═N— and —NR$_9$—, $R_5$ is selected from the group consisting of hydrogen, halogen, lower haloalkyl, lower alkyl, lower alkoxy, lower alkoxy lower alkyl, lower alkylthio lower alkyl, cycloalkyl of 3 to 6 carbon atoms, cycloalkyl lower alkyl, —CN, lower cyanoalkyl, lower alkyl lower sulfonylalkyl, lower hydroxyalkyl, —NO$_2$,

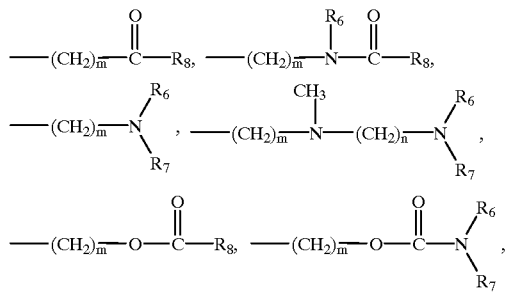

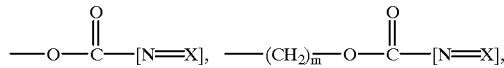

—(CH$_2$)$_m$—S(O)$_q$—R$_{11}$, —(CH$_2$)$_m$—P(O)—R$_{12}$ R$_{13}$, —(CH$_2$)$_2$—P(S)—R$_{12}$ R$_{13}$, unsubstituted or substituted —(CH$_2$)$_n$—[N=X],

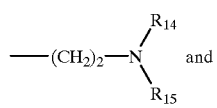

unsubstituted or substituted aryl and unsubstituted or substituted lower aralkyl with 1 to 4 substituents on the aryl selected from the group consisting of lower alkyl, halogen, —OH, —NO$_2$, —NH$_2$, lower alkylamino, lower haloalkyl, lower hydroxyalkyl, lower alkoxy and lower alkoxy lower alkyl, $R_6$ and $R_7$ are individually selected from the group consisting of hydrogen, lower alkyl, lower hydroxyalkyl, lower alkyl lower aminoalkyl, lower aminoalkyl, cycloalkyl of 3 to 6 carbon atoms, cycloalkyl lower alkyl, lower alkenyl, lower haloalkyl, lower alkoxy lower alkyl, unsubstituted or substituted aryl and unsubstituted or substituted aryl lower alkyl with 1 to 4 substituents on the aryl selected from the group consisting of lower alkyl, halogen, —NO$_2$, —NH$_2$, lower alkylamino, lower haloalkyl, lower hydroxyalkyl, lower alkoxy and lower alkoxy lower alkyl, $R_8$ is selected from the group consisting of hydrogen, lower alkyl, lower hydroxyalkyl, —NH$_2$, lower alkylamino, lower alkyl lower aminoalkyl, lower aminoalkyl, cycloalkyl of 3 to 6 carbon atoms, cycloalkyl lower alkyl, lower alkenyl, lower alkoxy, lower alkoxy lower alkyl, lower haloalkyl, unsubstituted or substituted aryl and unsubstituted or substituted aryl lower alkyl with 1 to 4 substituents on the aryl selected from the group consisting of lower alkyl, halogen, —NO$_2$, —NH$_2$, lower alkylamino, lower haloalkyl, lower hydroxyalkyl, lower alkoxy and lower alkoxy lower alkyl, $R_9$ is selected from the group consisting of hydrogen, lower alkyl, lower haloalkyl, unsubstituted or substituted aryl, unsubstituted or substituted lower aralkyl where the aryl has at least one substituent on the aryl selected from the group consisting of lower alkyl, halogen, —NO$_2$, —NH$_2$, lower alkylamino, lower haloalkyl, lower hydroxyalkyl, lower alkoxy and lower alkoxy lower alkyl, $R_{10}$ is selected from the group consisting of hydrogen, lower alkyl, lower haloalkyl, lower alkoxy, aryl and aryl substituted with 1 to 4 members of the group consisting of lower alkyl, lower haloalkyl, lower hydroxyalkyl and lower alkoxy lower alkyl, $R_{11}$ is selected from the group consisting of lower alkyl, aryl, —(CH$_2$)$_m$—, —OR$_{14}$, —(CH$_2$)$_m$—S—R$_{14}$,

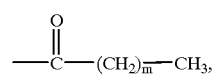

—(CH$_2$)$_m$—[N=X], R$_{12}$ and R$_{13}$ are individually selected from the group consisting of lower alkyl, aryl, lower alkoxy, aryloxy and —NH$_2$, R$_{14}$ and R$_{15}$ are individually selected from the group consisting of hydrogen, lower alkyl and aryl
R$_{18}$ and R$_{19}$ are individually selected from the group consisting of hydrogen, halogen, lower alkyl, lower alkoxy and —OH, R$_{20}$ is hydrogen or halogen, R$_{21}$ is selected from the group consisting of hydrogen, lower alkyl, —CHO and

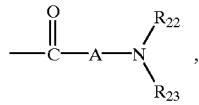

m is an integer from 0 to 6, R$_p$ is selected from the group consisting of hydrogen and an easily cleavable group of the formula

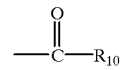

A is alkylene unsubstituted or substituted with at least one member of the group consisting of —OH, salified —OH, acyloxy of an organic carboxylic acid of 1 to 6 carbon atoms, halogen, —COOH, —COOH esterified with an alkanol of 1 to 6 carbon atoms, salified carboxy, —NH$_2$ and mono- and di -lower alkylamino, R$_{22}$ and R$_{23}$ are individually selected from the group consisting of hydrogen, lower alkyl, hydroxy lower alkyl, lower alkyl lower aminoalkyl, lower aminoalkyl, cycloalkyl of 3 to 6 carbon atoms, cycloalkyl lower alkyl, lower alkenyl, lower alkoxy lower alkyl, lower haloalkyl, unsubstituted or substituted aryl and lower aralkyl with 1 to 4 substituents on the aryl selected from the group consisting of lower alkyl, halogen, —NO$_2$, —NH$_2$, lower alkylamino, lower haloalkyl, lower hydroxylalkyl, lower alkoxy and lower alkoxy lower alkyl, n is 1 or 2, qis an integer from 0 to 2, —[N=X] is a heterocycle of 4 to 7 ring members with X being the chain remainder selected from the group consisting of —O—, —S—, —CH$_2$, =CH—, =N—, —NR$_9$— and $$-\overset{O}{\underset{\|}{C}}-R_{10}$$

and its non-toxic, pharmaceutically acceptable salts.

2. A compound of claim 1 wherein the easily cleavable group is

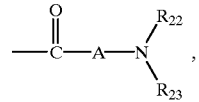

A is unsubstituted or substituted alkylene with a substituent selected from the group consisting of —OH, salified hydroxy, free carboxy, salified carboxy, carboxy esterified with an alcohol of 1 to 6 carbon atoms, halogen, —$NH_2$ and mono and di lower alkylamino and $R_{22}$ and $R_{23}$ are individually selected from the group consisting of hydrogen, lower alkyl, lower hydroxy alkyl, lower alkyl lower aminoalkyl, lower aminoalkyl, cycloalkyl of 3 to 6 carbon atoms, cycloalkyl lower alkyl, lower alkenyl, lower alkoxy lower alkyl, lower haloalkyl, unsubstituted or substituted aryl with 1 to 4 substituents selected from the group consisting of lower alkyl, halogen, —$NO_2$, —$NH_2$, lower alkylamino, lower haloalkyl, lower hydroxy alkyl, lower alkoxy and lower alkoxy lower alkyl.

3. A compound of claim 1 wherein $R_1$ is lower alkyl, $R_2$ is halogen, $R_3$ is selected from the group consisting of hydrogen, halogen and lower haloalkyl, $R_5$ is selected from the group consisting of halogen, lower alkyl, lower haloalkyl, lower aminoalkyl, unsubstituted or substituted —$(CH_2)_n$—[N=X] and unsubstituted or substituted aryl and aralkyl, $R_{18}$ and $R_{19}$ are hydrogen and $R_{20}$ is hydrogen.

4. A compound of claim 3 wherein $R_1$ is ethyl.

5. A compound of claim 1 wherein $R_1$ is lower alkyl, $R_2$, $R_3$ and $R_4$ are independently selected from the group consisting of hydrogen, halogen, lower alkyl, —$(CH_2)_m$—$NR_6R_7$, —$(CH_2)_m OR_6$ and —$(CH_2)_n$[N=X], [N=X] is a heterocyclic of 4 to 7 ring members with N and X being the remaining ring members selected from the group consisting of oxygen, —$CH_2$, —CH= and

or $R_2$ and $R_3$ or $R_3$ and $R_4$ together form a chain of 3 to 4 members selected from the group consisting of —$CH_2$—, —O—, and

, $R_9$ is lower alkyl or unsubstituted aryl lower alkyl, $R_5$ is hydrogen, halogen, lower alkyl, lower alkoxy lower alkyl, cycloalkyl of 3 to 6 carbon atoms, lower hydroxyalkyl, —$(CH_2)_m$—$NR_6R_7$—, —$(CH_2)_n$[N=X], unsubstituted or substituted aryl and unsubstituted or substituted lower aralkyl with 1 to 4 substituents on the aryl selected from the group consisting of lower alkyl or halogen, $R_6$ and $R_7$ are independently selected from the group consisting of hydrogen, lower alkyl, aryl lower alkyl, $R_{18}$, $R_{19}$, $R_{20}$, $R_{22}$ and $R_{23}$ are hydrogen and $R_p$ is hydrogen or a group of formula

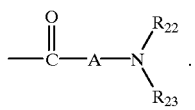

6. A compound according to claim 1, characterized in that is one of the following compounds:

5-ethyl-5-hydroxy-1,4,5,13-tetrahydro-3H,15H-oxepino-[3',4':6,7]indolizino[1,2-b]quinoline-3,15-dione;

5,12-diethyl-5-hydroxy-1,4,5,13-tetrahydro-3H,15H-oxepino[3',4':6,7]indolizino[1,2-b]quinoline-3,15-dione;

8-ethyl-8-hydroxy-2,3,8,9,12,15-hexahydro-10H,13H-[1,4]dioxino[2,3-g]oxepino[3',4':6,7]indolizino[1,2-b]quinoline-10,13-dione;

10-(benzyloxy)-5-ethyl-5-hydroxy-1,4,5,13-tetrahydro-3H,15H-oxepino[3',4':6,7]indolizino[1,2-b]quinoline-3,15-dione;

5-ethyl-5,10-dihydroxy-1,4,5,13-tetrahydro-3H,15H-oxepino[3',4':6,7]indolizino[1,2-b]quinoline-3,15-dione;

11-[(dimethylamino)methyl]-5-ethyl-5,10-dihydroxy-1,4,5,13-tetrahydro-3H,15H-oxepino[3',4':6,7]indolizino[1,2-b]quinoline-3,15-dione;

5-ethyl-9-fluoro-5-hydroxy-10-methoxy-1,4,5,13-tetrahydro-3H,15H-oxepino[3',4':6,7]indolizino[1,2-b]quinoline-3,15-dione;

9-chloro-5-ethyl-5-hydroxy-10-methyl-1,4,5,13-tetrahydro-3H,15H-oxepino[3',4':6,7]indolizino[1,2-b]quinoline-3,15-dione;

5-ethyl-9,10-difluoro-5-hydroxy-1,4,5,13-tetrahydro-3H,15H-oxepino[3',4':6,7]indolizino[1,2-b]quinoline-3,15-dione;

7-ethyl-7-hydroxy-7,8,11,14-tetrahydro-9H,12H-[1,3]dioxolo[4,5-g]oxepino[3',4':6,7]indolizino[1,2-b]quinoline-9,12-dione;

9-chloro-5-ethyl-5-hydroxy-10-methoxy-1,4,5,13-tetrahydro-3H,15H-oxepino[3',4':6,7]indolizino[1,2-b]quinoline-3,15-dione;

5-ethyl-5-hydroxy-10-methoxy-1,4,5,13-tetrahydro-3H,15H-oxepino[3',4':6,7]indolizino[1,2-b]quinoline-3,15-dione;

9,11-dichloro-5-ethyl-5-hydroxy-1,4,5,13-tetrahydro-3H,15H-oxepino[3',4':6,7]indolizino[1,2-b]quinoline-3,15-dione;

5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-10-fluoro-5-hydroxy-1,4,5,13-tetrahydro-3H,15H-oxepino[3',4':6,7]indolizino[1,2-b]quinoline-3,15-dione;

10-chloro-5-ethyl-5-hydroxy-1,4,5,13-tetrahydro-3H,15H-oxepino[3',4':6,7]indolizino[1,2-b]quinoline-3,15-dione;

9-chloro-5-ethyl-10-fluoro-5-hydroxy-1,4,5,13-tetrahydro-3H,15H-oxepino[3',4':6,7]indolizino[1,2-b]quinoline-3,15-dione;

5-ethyl-5,10-dihydroxy-11-(4-morpholinylmethyl)-1,4,5,13-tetrahydro-3H,15H-oxepino[3',4':6,7]indolizino[1,2-b]quinoline-3,15-dione;

5,12-diethyl-9-fluoro-5-hydroxy-10-methoxy-1,4,5,13-tetrahydro-3H,15H-oxepino[3',4':6,7]indolizino[1,2-b]quinoline-3,15-dione;

5-ethyl-5-hydroxy-12-methyl-1,4,5,13-tetrahydro-3H,15H-oxepino[3',4':6,7]indolizino[1,2-b]quinoline-3,15-dione;

9-chloro-5-ethyl-5-hydroxy-10-methoxy-12-[(4-methyl-1-piperazinyl)methyl]-1,4,5,13-tetrahydro-3H,15H-oxepino[3',4':6,7]indolizino[1,2-b]quinoline-3,15-dione;

9-chloro-5-ethyl-5-hydroxy-10-methoxy-12-(4-morpholinylmethyl)-1,4,5,13-tetrahydro-3H,15H-oxepino[3',4':6,7]indolizino[1,2-b]quinoline-3,15-dione;

5-ethyl-5-hydroxy-12-[(4methyl-1-piperazinyl)methyl]1,4,5,13-tetrahydro-3H,15H-oxepino[3',4':6,7]indolizino[1,2-b]quinoline-3,15-dione;

5-ethyl-5-hydroxy-12-(1-piperidinylmethyl)-1,4,5,13-tetrahydro-3H,15H-oxepino[3',4':6,7]indolizino[1,2-b]quinoline-3,15-dione;

5-ethyl-5-hydroxy-12-(4-morpholinylmethyl)-1,4,5,13-tetrahydro-3H,15H-oxepino[3',4':6,7]indolizino[1,2-b]quinoline-3,15-dione;

5-ethyl-10-fluoro-5-hydroxy-12-[(4-methyl-1-piperazinyl)methyl]-1,4,5,13-tetrahydro-3H,15H-oxepino[3',4':6,7]indolizino[1,2-b]quinoline-3,15-dione;

5-ethyl-10-fluoro-5-hydroxy-12-(4-morpholinylmethyl)-1,4,5,13-tetrahydro-3H,15H-oxepino[3',4':6,7]indolizino[1,2-b]quinoline-3,15-dione;

5-ethyl-9-fluoro-5-hydroxy-10methyl-12-[(4-methyl-1-piperazinyl)methyl]1,4,5,13-tetrahydro-3H,15H-oxepino[3',4':6,7]indolizino[1,2-b]quinoline-3,15-dione;

5-ethyl-9-fluoro-5-hydroxy-10-methyl-12-(4-morpholinylmethyl)-1,4,5,13-tetrahydro-3H,15H-oxepino[3',4':6,7]indolizino[1,2-b]quinoline-3,15-dione;

5-ethyl-9-fluoro-5-hydroxy-10-methyl-12-(1-piperidinylmethyl)-1,4,5,13-tetrahydro-3H,15H-oxepino[3',4':6,7]indolizino[1,2-b]quinoline-3,15-dione;

8-ethyl-8-hydroxy-16-[(4-methyl-1-piperazinyl)methyl]-2,3,8,9,12,15-hexahydro-10H,13H-[1,4]dioxino[2,3-g]oxepino[3',4':6,7]indolizino[1,2-b]quinoline-10,13-dione;

9-chloro-5-ethyl-10-fluoro-5-hydroxy-12-(4-morpholinylmethyl)-1,4,5,13-tetrahydro-3H,15H-oxepino[3',4':6,7]indolizino[1,2-b]quinoline-3,15-dione;

12-[3,6-dihydro-1(2H)-pyridinylmethyl]-5-ethyl-9,10-difluoro-5-hydroxy-1,4,5,13-tetrahydro-3H,15H-oxepino[3',4':6,7]indolizino[1,2-b]quinoline-3,15-dione;

5-ethyl-9,10-difluoro-5-hydroxy-12-[(4-methyl-1-piperidinyl)methyl]1,4,5,13-tetrahydro-3H,15H-oxepino[3',4':6,7]indolizino[1,2-b]quinoline-3,15-dione;

5-ethyl-9,10-difluoro-5-hydroxy-12-(1-pyrrolidinylmethyl)-1,4,5,13-tetrahydro-3H,15H-oxepino[3',4':6,7]indolizino[,12-b]quinoline-3,15-dione;

5-ethyl-9,10-difluoro-5-hydroxy-12-[(4-methyl-1-piperazinyl)methyl]1,4,5,13-tetrahydro-3H,15H-oxepino[3',4':6,7]indolizino[1,2-b]quinoline-3,5-dione;

5-ethyl-9,10-difluoro-5-hydroxy-12-(1-piperidinylmethyl)-1,4,5,13-tetrahydro-3H,15H-oxepino[3',4':6,7]indolizino1,2-b]quinoline-3,15-dione;

12-[(dimethylamino)methyl]-5-ethyl-9,10-difluoro-5-hydroxy-1,4,5,13-tetrahydro-3H,15H-oxepino[3',4':6,7]indolizino[1,2-b]quinoline-3,15-dione;

9-chloro-5-ethyl-5-hydroxy-10-methyl-12-(4-morpholinylmethyl)-1,4,5,13-tetrahydro-3H,15H-oxepino[3',4':6,7]indolizino[1,2-b]quinoline-3,15-dione;

9-chloro-5-ethyl-5-hydroxy-10-methyl-12-[(4-methyl-1-piperazinyl)methyl]1,4,5,13-tetrahydro-3H,15H-oxepino[3',4':6,7]indolizino[1,2-b]quinoline-3,15-dione;

12-{[benzyl(methyl)amino]methyl}-9-chloro-5-ethyl-5-hydroxy-10-methyl-1,4,5,13-tetrahydro-3H,15H-oxepino[3',4':6,7]indolizino[1,2-b]quinoline-3,15-dione;

12-[(4-benzyl-1-piperazinyl)methyl]9-chloro-5-ethyl-5-hydroxy-10-methyl-1,4,5,13-tetrahydro-3H,15H-oxepino[3',4':6,7]indolizino[1,2-b]quinoline-3,15-dione;

9-chloro-5-ethyl-5-hydroxy-10-methyl-12-(1-piperidinylmethyl)-1,4,5,13-tetrahydro-3H,15H-oxepino[3',4':6,7]indolizino[1,2-b]quinoline-3,15-dione;

12-[(4-benzyl-1-piperazinyl)methyl]5-ethyl-10-fluoro-5-hydroxy-1,4,5,13-tetrahydro-3H,15H-oxepino[3',4':6,7]indolizino[1,2-b]quinoline-3,15-dione;

12-[(4-benzyl-1-piperazinyl)methyl]5-ethyl-9-fluoro-5-hydroxy-10-methyl-1,4,5,13-tetrahydro-3H,15H-oxepino[3',4':6,7]indolizino[1,2-b]quinoline-3,15-dione;

12-[(dimethylamino)methyl]-5-ethyl-9-fluoro-5-hydroxy-10-methyl-1,4,5,13-tetrahydro-3H,15H-oxepino[3',4':6,7]indolizino[1,2-b]quinoline-3,15-dione;

12-[(diethylamino)methyl]-5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-9-fluoro-5-hydroxy-10-methyl-12-[(4-methyl-1-piperidinyl)methyl]1,4,5,13-tetrahydro-3H,15H-oxepino[3',4':6,7]indolizino[1,2-b]quinoline-3,15-dione;

5-ethyl-9-fluoro-5-hydroxy-10-methyl-12-(1-pyrrolidinylmethyl)-1,4,5,13-tetrahydro-3H,15H-oxepino[3',4':6,7]indolizino[1,2-b]quinoline-3,15-dione;

12-[3,6-dihydro-1(2H)-pyridinylmetbyl]5-etbyl-9-fluoro-5-hydroxy-10-methyl-1,4,5,13-tetrahydro-3H,15H-oxepino[3',4':6,7]indolizino[1,2-b]quinoline-3,15-dione;

12-[(diisobutylamino)methyl]-5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-9-fluoro-5-hydroxy-10-methoxy-12-[(4-methyl-1-piperazinyl)methyl]-1,4,5,13-tetrahydro-3H,15H-oxepino[3',4':6,7]indolizino[1,2-b]quinoline-3,15-dione;

5-ethyl-9-fluoro-5-hydroxy-10-methoxy-12-(1-piperidinylmethyl)-1,4,5,13-tetrahydro-3H,15H-oxepino[3',4':6,7]indolizino[1,2-b]quinoline-3,15-dione;

9-chloro-12-[(dimethylamino)methyl]-5-ethyl-5-hydroxy-10-methoxy-1,4,5,13-tetrahydro-3H,15H-oxepino[3',4':6,7]indolizino[1,2-b]quinoline-3,15-dione;

9-chloro-5-ethyl-5-hydroxy-10-methoxy-12-(1-piperidinylmethyl)-1,4,5,13-tetrahydro-3H,15H-oxepino[3',4':6,7]indolizino[1,2-b]quinoline-3,15-dione;

12-[3,6-dihydro-1(2H)-pyridinylmethyl]-5-ethyl-5-hydroxy-10-methoxy-1,4,5,13-tetrahydro-3H,15H-oxepino[3',4':6,7]indolizino[1,2-b]quinoline-3,15-dione;

5-ethyl-5-hydroxy-10-methoxy-12-[(4-methyl-1-piperidinyl)methyl]-1,4,5,13-tetrahydro-3H,15H-oxepino[3',4':6,7]indolizino[1,2-b]quinoline-3,15-dione;

5-ethyl-5-hydroxy-10-methoxy-12-[(4-methyl-1-piperazinyl)methyl]1,4,5,13-tetrahydro-3H,15H-oxepino[3',4':6,7]indolizino[1,2-b]quinoline-3,15-dione;

5-ethyl-5-hydroxy-10-methoxy-12-(1-pyrrolidinylmethyl)-1,4,5,13-tetrahydro-3H,15H-oxepino[3',4':6,7]indolizino[1,2-b]quinoline-3,15-dione;

12-[(4-benzyl-1-piperazinyl)methyl]-5-ethyl-5-hydroxy-10-methoxy-1,4,5,13-tetrahydro-3H,15H-oxepino[3',4':6,7]indolizino[1,2-b)quinoline-3,15-dione;

9-chloro-5-ethyl-5-hydroxy-10-methyl-12-[(4-methyl-1-piperidinyl)methyl]-1,4,5,13-tetrahydro-3H,15H-oxepino[3',4':6,7]indolizino[1,2-b]quinoline-3,15-dione;

10-(benzyloxy)-5-ethyl-9-fluoro-5-hydroxy-1,4,5,13-tetrahydro-3H,15H-oxepino[3',4':6,7]indolizino(1,2-b]quinoline-3,15-dione;

5-ethyl-9-fluoro-5,10-dihydroxy-1,4,5,13-tetrahydro-3H,15H-oxepino[3',4':6,7]indolizino[1,2-b]quinoline-3,15-dione;

5-ethyl-9,10-difluoro-3,15-dioxo-4,5,13,15-tetrahydro-1H,3H-oxepino[3',4':6,7]indolizino[1,2-b]quinolin-5-yl 2-aminoacetate;

5-ethyl-9,10-difluoro-3,15-dioxo-4,5,13,15-tetrahydro-1H,3H-oxepino[3',4':6,7]indolizino[1,2-b]quinolin-5-yl 3-aminopropanoate;

2,9-diethyl-9-hydroxy-1,2,3,9,10,16-hexahydro-13H-[1,3]oxazino[5,6-f]oxepino[3',4':6,7]indolizino[1,2-b]quinoline-11,14-dione;

9-ethyl-9-hydroxy-2-methyl-1,2,3,9,10,16-hexahydro-13H-[1,3]oxazino[5,6-f]oxepino[3',4':6,7]indolizino[1,2-b]quinoline-11,14-dione;

2-benzyl-9-ethyl-9-hydroxy-1,2,3,9,10,16-hexahydro-13H-[1,3]oxazino[5,6-f]oxepino[3',4':6,7]indolizino[1,2-b]quinoline-11,14-dione;

2-benzyl-9-ethyl-5-fluoro-9-hydroxy-1,2,3,9,10,16-hexahydro-13H-[1,3]oxazino[5,6-j]oxepino[3',4':6,7]indolizino[1,2-b]quinoline-11,14-dione;

(+)-5-ethyl-9,10-difluoro-5-hydroxy-4,5,13,15-tetrahydro-1H,3H-oxepino[3',4':6,7]indolizino[1,2-b]quinoline-3,15-dione;

(+)-1-[9-chloro-5-ethyl-5-hydroxy-10-methyl-3,15dioxo-4,5,13,15-tetrahydro-1H,3H-oxepino[3',4':6,7]indolizino[1,2-b]quinolin-12-ylmethy])4-methylhexahydropyridine;

or a pharmaceutically acceptable salt of the latter.

7. A compound according to claim 6, characterized in that is one of the following compounds:

5-ethyl-5-hydroxy-1,4,5,13-tetrahydro-3H,15H-oxepino[3',4':6,7]indolizino[1,2-b]quinoline-3,15-dione;

5,12-diethyl-5-hydroxy-1,4,5,13-tetrahydro-3H,15H-oxepino[3',4':6,7]indolizino[1,2-b]quinoline-3,15-dione;

8-ethyl-8-hydroxy-2,3,8,9,12,15-hexahydro-10H,13H-[1,4]dioxino[2,3-g]oxepino[3',4':6,7]indolizino[1,2-b]quinoline-10,13-dione;

5-ethyl-5,10-dihydroxy-1,4,5,13-tetrahydro-3H,15H-oxepino[3',4':6,7]-indolizino[1,2-b]quinoline-3,15-dione;

5-ethyl-9-fluoro-5-hydroxy-10-methoxy-1,4,5,13-tetrahydro-3H,15H-oxepino[3',4':6,7]indolizino[1,2-b]quinoline-3,15-dione;

9-chloro-5-ethyl-5-hydroxy-10-methyl-1,4,5,13-tetrahydro-3H,15H-oxepino[3',4':6,7]indolizino[1,2-b]quinoline-3,15-dione;

5-ethyl-9,10-difluoro-5-hydroxy-1,4,5,13-tetrahydro-3H,15H-oxepino[3',4':6,7]indolizino[1,2-b]quinoline-3,15-dione;

7-ethyl-7-hydroxy-7,8,11,14-tetrahydro-9H,12H-[1,3]dioxolo[4,5-g]oxepino[3',4':6,7]indolizino[1,2-b]quinoline-9,12-dione;

9-chloro-5-ethyl-5-hydroxy-10-methoxy-1,4,5,13-tetrahydro-3H,15H-oxepino[3',4':6,7]indolizino[f,2-b]quinoline-3,15dione;

5-ethyl-5-hydroxy-10-methoxy-1,4,5,13-tetrahydro-3H,15H-oxepino[3',4':6,7]indolizino[1,2-b]quinoline-3,15-dione;

9,11-dichloro-5-ethyl-5-hydroxy-1,4,5,13-tetrahydro-3H,1 5H-oxepino[3',4':6,7]indolizino[1,2-b]quinoline-3,15-dione;

5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-10-fluoro-5-hydroxy-1,4,5,13-tetrahydro-3H,15H-oxepino[3',4':6,7]indolizino[1,2-b]quinoline-3,15-dione;

10-chloro-5-ethyl-5-hydroxy-1,4,5,13-tetrahydro-3H,15H-oxepino[3',4':6,7]indolizino[1,2-b]quinoline-3,15-dione;

9-chloro-5-ethyl-10-fluoro-5-hydroxy-1,4,5,13-tetrahydro-3H,15H-oxepino[3',4':6,7]indolizino[1,2-b]quinoline-3,15-dione;

5,12-diethyl-9-fluoro-5-hydroxy-10-methoxy-1,4,5,13-tetrahydro-3H,15H-oxepino[3',4':6,7]indolizino[1,2-b]quinoline-3,15-dione;

5-ethyl-5-hydroxy-12-methyl-1,4,5,13-tetrahydro-3H,15H-oxepino[3',4':6,7]indolizino[1,2-b]quinoline-3,15-dione;

5-ethyl-5-hydroxy-12-(4-morpholinylmethyl)-1,4,5,13-tetrahydro-3H,15H-oxepino[3',4':6,7]indolizino[1,2-b]quinoline-3,15-dione;

5-ethyl-9-fluoro-5-hydroxy-10-methyl-12-[(4-methyl-1-piperazinyl)methyl]1,4,5,13-tetrahydro-3H,15H-oxepino[3',4':6,7]indolizino[1,2-b]quinoline-3,15-dione;

5-ethyl-9-fluoro-5-hydroxy-10-methyl-12-(4-morpholinylmethyl)-1,4,5,13-tetrahydro-3H,15H-oxepino[3',4':6,7]indolizino[1,2-b]quinoline-3,15-dione;

5-ethyl-9-fluoro-5-hydroxy-10-methyl-12-(1-piperidinylmethyl)-1,4,5,13-tetrahydro-3H,15H-oxepino[3',4':6,7]indolizino[1,2-b]quinoline-3,15-dione;

12-[3,6-dihydro-1(2H)-pyridinylmethyl]5-ethyl-9,10-difluoro-5-hydroxy-1,4,5,13-tetrahydro-3H,15H-oxepino[3',4':6,7]indolizino[1,2-b]quinoline-3,15-dione;

5-ethyl-9,10-difluoro-5-hydroxy-12-[(4-methyl-1-piperidinyl)methyl]-1,4,5,13-tetrahydro-3H,15H-oxepino[3',4':6,7]indolizino[1,2-b]quinoline-3,15-dione;

5-ethyl-9,10-difluoro-5-hydroxy-12-(1-pyrrolidinylmethyl)-1,4,5,13-tetrahydro-3H,15H-oxepino[3',4':6,7]indolizino[1,2-b]quinoline-3,15-dione;

5-ethyl-9,10-difluoro-5-hydroxy-12-[(4-methyl-1-piperazinyl)methyl]1,4,5,13-tetrahydro-3H,15H-oxepino[3',4':6,7]indolizino[1,2-b]quinoline-3,15-dione;

5-ethyl-9,10-difluoro-5-hydroxy-12-(1-piperidinylmethyl)-1,4,5,13-tetrahydro-3H,15H-oxepino[3',4':6,7]indolizino[1,2-b]quinoline-3,15-dione;

12-[(dimethylamino)methyl]5-ethyl-9,10-difluoro-5-hydroxy-1,4,5,13-tetrahydro-3H,15H-oxepino[3',4':6,7]indolizino[1,2-b]quinoline-3,15-dione;

9-chloro-5-ethyl-5-hydroxy-10-methyl-12-(4-morpholinylmethyl)-1,4,5,13-tetrahydro-3H,15H-oxepino[3',4':6,7]indolizino[1,2-b]quinoline-3,15-dione;

9-chloro-5-ethyl-5-hydroxy-10-methyl-12-[(4-methyl-1-piperazinyl)methyl]1,4,5,13-tetrahydro-3H,15H-oxepino[3',4':6,7]indolizino[1,2-b]quinoline-3,15-dione;

12-[(4-benzyl-1-piperazinyl)methyl]9-chloro-5-ethyl-5-hydroxy-10-methyl-1,4,5,13-tetrahydro-3H,15H-oxepino[3',4':6,7]indolizino[1,2-b]quinoline-3,15-dione;

12-[(diethylamino)methyl]-5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-9-fluoro-5-hydroxy-10-methyl-12-[(4-methyl-1-piperidinyl)methyl]1,4,5,13-tetrahydro-3H,15H-oxepino[3',4':6,7]indolizino[1,2-b]quinoline-3,15-dione;

5-ethyl-9-fluoro-5-hydroxy-10-methyl-12-(1-pyrrolidinylmethyl)-1,4,5,13-tetrahydro-3H,15H-oxepino[3',4':6,7]indolizino[1,2-b]quinoline-3,15-dione;

12-[3,6-dihydro-1(2H)-pyridinylmethyl]5-ethyl-9-fluoro-5-hydroxy-10-methyl-1,4,5,13-tetrahydro-3H,15H-oxepino[3',4':6,7]indolizino[1,2-b]quinoline-3,15-dione;

12-[(diisobutylamino)methyl]5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-9-fluoro-5-hydroxy-10-methoxy-12-(1-piperidinylmethyl)-1,4,5,13-tetrahydro-3H,15H-oxepino[3',4':6,7]indolizino[1,2-b]quinoline-3,15-dione;

9-chloro-12-[(dimethylamino)methyl]5-ethyl-5-hydroxy-10-methoxy-1,4,5,13-tetrahydro-3H,15H-oxepino[3',4':6,7]indolizino[1,2-b]quinoline-3,15-dione;

9-chloro-5-ethyl-5-hydroxy-10-methoxy-12-(1-piperidinylmethyl)-1,4,5,13-tetrahydro-3H,15H-oxepino[3',4':6,7]indolizino[1,2-b]quinoline-3,15-dione;

5-ethyl-5-hydroxy-10-methoxy-12-[(4-methyl-1-piperidinyl)methyl]1,4,5,13-tetrahydro-3H,15H-oxepino[3',4':6,7]indolizino[1,2-b]quinoline-3,15-dione;

9-chloro-5-ethyl-5-hydroxy-10-methyl-12-[(4-methyl-1-piperidinyl)methyl]1,4,5,13-tetrahydro-3H,15H-oxepino[3',4':6,7]indolizino[1,2-b]quinoline-3,15-dione;

5-ethyl-9-fluoro-5,10-dihydroxy-1,4,5,13-tetrahydro-3H,15H-oxepino[3',4':6,7]indolizino[1,2-b]quinoline-3,15-dione;

2,9-diethyl-9-hydroxy-1,2,3,9,10,16-hexahydro-13H-[1,3]oxazino[5,6-f]oxepino[3',4':6,7]indolizino[1,2-b]quinoline-11,14-dione;

9-ethyl-9-hydroxy-2-methyl-1,2,3,9,10,16-hexahydro-13H-[1,3]oxazino[5,6-f]oxepino[3',4':6,7]indolizino[1,2-b]quinoline-11,14-dione;

2-benzyl-9-ethyl-9-hydroxy-1,2,3,9,10,16-hexahydro-13H-[1,3]oxazino[5,6-f]oxepino[3',4':6,7]indolizino[1,2-b]quinoline-11,14-dione;

2-benzyl-9-ethyl-5-fluoro-9-hydroxy-1,2,3,9,10,16-hexahydro-13H-[1,3]oxazino[5,6-f]oxepino[3',4':6,7]indolizino[1,2-b]quinoline-11,14-dione;

(+)-5-ethyl-9,10-difluoro-5-hydroxy-4,5,13,15-tetrahydro-1H,3H-oxepino[3',4':6,7]indolizino[1,2-b]quinoline-3,15-dione;

(+)-1-[9-chloro-5-ethyl-5-hydroxy-10-methyl-3,15-dioxo-4,5,13,15-tetrahydro-1H,3H-oxepino[3',4':6,7]indolizino[1,2-b]quinolin-12-ylmethyl]4-methylhexahydropyridine;

or a pharmaceutically acceptable salt of the latter.

8. A compound according to claim 7, characterized in that is one of the following compounds:

5-ethyl-5-hydroxy-1,4,5,13-tetrahydro-3H,15H-oxepino[3',4':6,7]indolizino[1,2-b]quinoline-3,15-dione;

5,12-diethyl-5-hydroxy-1,4,5,13-tetrahydro-3H,15H-oxepino[3',4':6,7]indolizino[1,2-b]quinoline-3,15-dione;

8-ethyl-8-hydroxy-2,3,8,9,12,15-hexahydro-10H,13H-[1,4]dioxino[2,3-g]oxepino[3',4':6,7]indolizino[1,2-b]quinoline-10,13-dione;

5-ethyl-5,10-dihydroxy-1,4,5,13-tetrahydro-3H,15H-oxepino[3',4':6,7]indolizino[1,2-b]quinoline-3,15-dione;

5-5-ethyl-9-fluoro-5-hydroxy-10-methoxy-1,4,5,13-tetrahydro-3H,15H-oxepino[3',4':6,7]indolizino[1,2-b]quinoline-3,15-dione;

9-chloro-5-ethyl-5-hydroxy-10-methyl-1,4,5,13-tetrahydro-3H,15H-oxepino[3',4':6,7]indolizino[1,2-b]quinoline-3,15-dione;

5-ethyl-9,10-difluoro-5-hydroxy-1,4,5,13-tetrahydro-3H,15H-oxepino[3',4':6,7]indolizino[1,2-b]quinoline-3,15-dione;

7-ethyl-7-hydroxy-7,8,11,14-tetrahydro-9H,12H-[1,3]dioxolo[4,5-g]oxepino[3',4':6,7]indolizino[1,2-b]quinoline-9,12-dione;

9-chloro-5-ethyl-5-hydroxy-10-methoxy-1,4,5,13-tetrahydro-3H,15H-oxepino[3',4':6,7]indolizino[1,2-b]quinoline-3,15-dione;

5-ethyl-5-hydroxy-10-methoxy-1,4,5,13-tetrahydro-3H,15H-oxepino[3',4':6,7]indolizino[1,2-b]quinoline-3,15-dione;

5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-10-fluoro-5-hydroxy-1,4,5,13-tetrahydro-3H,15H-oxepino[3',4':6,7]indolizino[1,2-b]quinoline-3,15-dione;

10-chloro-5-ethyl-5-hydroxy-1,4,5,13-tetrahydro-3H,15H-oxepino[3',4':6,7]indolizino[1,2-b]quinoline-3,15-dione;

9-chloro-5-ethyl-10-fluoro-5-hydroxy-1,4,5,13-tetrahydro-3H,15H-oxepino[3',4':6,7]indolizino[1,2-b]quinoline-3,15-dione;

5,12-diethyl-9-fluoro-5-hydroxy-10-methoxy-1,4,5,13-tetrahydro-3H,15H-oxepino[3',4':6,7]indolizino[1,2-b]quinoline-3,15-dione;

5-ethyl-5-hydroxy-12-methyl-1,4,5,13-tetrahydro-3H,15H-oxepino[3',4':6,7]indolizino[1,2-b]quinoline-3,15-dione;

5-ethyl-5-hydroxy-12-(4-morpholinylmethyl)-1,4,5,13-tetrahydro-3H,15H-oxepino[3',4':6,7]indolizino[1,2-b]quinoline-3,15-dione;

5-ethyl-9,10-difluoro-5-hydroxy-12-[(4-methyl-1-piperidinyl)methyl]-1,4,5,13-tetrahydro-3H,15H-oxepino[3',4':6,7]indolizino[1,2-b]quinoline-3,15-dione;

5-ethyl-9,10-difluoro-5-hydroxy-12-(1-pyrrolidinylmethyl)-1,4,5,13-tetrahydro-3H,15H-oxepino[3',4':6,7]indolizino[1,2-b]quinoline-3,15-dione;

9-chloro-5-ethyl-5-hydroxy-10-methyl-12-(4-morpholinylmethyl)-1,4,5,13-tetrahydro-3H,15H-oxepino[3',4':6,7]indolizino[1,2-b]quinoline-3,15-dione;

9-chloro-5-ethyl-5-hydroxy-10-methyl-12-[(4-methyl-1-piperazinyl)methyl]1,4,5,13-tetrahydro-3H,15H-oxepino[3',4':6,7]indolizino[1,2-b]quinoline-3,15-dione;

12-[(diethylamino)methyl]5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-9-fluoro-5-hydroxy-10-methyl-12-[(4-methyl-1-piperidinyl)methyl]1,4,5,13-tetrahydro-3H,15H-oxepino[3',4':6,7]indolizino[1,2-b]quinoline-3,15-dione;

12-[3,6-dihydro-1(2H)-pyridinylmethyl]5-ethyl-9-fluoro-5-hydroxy-10-methyl-1,4,5,13-tetrahydro-3H,15H-oxepino[3',4':6,7]indolizino[1,2-b]quinoline-3,15-dione;

5-ethyl-9-fluoro-5-hydroxy-10-methoxy-12-(1-piperidinylmethyl)-1,4,5,13-tetrahydro-3H,15H-oxepino[3',4':6,7]indolizino[1,2-b]quinoline-3,15-dione;

5-ethyl-9-fluoro-5,10-dihydroxy-1,4,5,13-tetrahydro-3H,15H-oxepino[3',4':6,7]indolizino[1,2-b]quinoline-3,15-dione;

2,9-diethyl-9-hydroxy-1,2,3,9,10,16-hexahydro-13H-[1,3]oxazino[5,6-f]oxepino[3',4':6,7]indolizino[1,2-b]quinoline-11,14-dione;

9-ethyl-9-hydroxy-2-methyl-1,2,3,9,10,16-hexahydro-13H-[1,3]oxazino[5,6-f]oxepino[3',4':6,7]indolizino[1,2-b]quinoline-11,14-dione;

2-benzyl-9-ethyl-9-hydroxy-1,2,3,9,10,16-hexahydro-13H-[1,3]oxazino[5,6-f]oxepino[3',4':6,7]indolizino[1,2-b]quinoline-11,14-dione;

2-benzyl-9-ethyl-5-fluoro-9-hydroxy-1,2,3,9,10,16-hexahydro-13H-[1,3]oxazino[5,6-f]oxepino[3',4':6,7]indolizino[1,2-b]quinoline-11,14-dione;

(+)-5-ethyl-9,10-difluoro-5-hydroxy4,5,13,15-tetrahydro-1H,3H-oxepino[3',4':6,7]indolizino[1,2-b]quinoline-3,15-dione;

(+)-1-[9-chloro-5-ethyl-5-hydroxy-10-methyl-3,15-dioxo-4,5,13,15-tetrahydro-1H,3H-oxepino[3',4':6,7]indolizino[1,2-b]quinolin-12-ylmethyl]4-methylhexahydropyridine;

or a pharmaceutically acceptable salt of the latter.

9. A compound according to claim 8, characterized in that is one of the following compounds:

5-ethyl-5-hydroxy-1,4,5,13-tetrahydro-3H,15H-oxepino[3',4':6,7]indolizino[1,2-b]quinoline-3,15-dione;

5-ethyl-5,10-dihydroxy-1,4,5,13-tetrahydro-3H,15H-oxepino[3',4':6,7]indolizino[1,2-b]quinoline-3,15-dione;

5-ethyl-10-fluoro-5-hydroxy-1,4,5,13-tetrahydro-3H,15H-oxepino[3',4':6,7]indolizino[1,2-b]quinoline-3,15-dione;

5-ethyl-9-fluoro-5,10-dihydroxy-1,4,5,13-tetrahydro-3H,15H-oxepino[3',4':6,7]indolizino[1,2-b]quinoline-3,15-dione;

(+)-5-ethyl-9,10-difluoro-5-hydroxy-4,5,13,15-tetrahydro-1H,3H-oxepino[3',4':6,7]indolizino[1,2-b]quinoline-3,15-dione;

(+)-1-[9-chloro-5-ethyl-5-hydroxy-10-methyl-3,15-dioxo-4,5,13,15-tetrahydro-1H,3H-oxepino[3',4':6,7]indolizino[1,2-b]quinolin-12-ylmethyl]4-methylhexahydropyzidine;

or a pharmaceutically acceptable salt of the latter.

10. A compound according to claim 9, characterized in that is one of the following compounds:

(+)-5-ethyl-9,10-difluoro-5-hydroxy-4,5,13,15-tetrahydro-1H,3H-oxepino[3',4':6,7]indolizino[1,2-b]quinoline-3,15-dione;

(+)-1-[9-chloro-5-ethyl-5-hydroxy-10-methyl-3,15-dioxo-4,5,13,15-tetrahydro-1H,3H-oxepino[3',4':6,7]indolizino[1,2-b]quinolin-12-ylmethyl]-4-methylhexahydropyridine;

or a pharmaceutically acceptable salt of the latter.

* * * * *

UNITED STATES PATENT AND TRADEMARK OFFICE
CERTIFICATE OF CORRECTION

PATENT NO.     : 6,339,091 B1
DATED          : January 15, 2002
INVENTOR(S)    : Dennis Bigg et al.

It is certified that error appears in the above-identified patent and that said Letters Patent is hereby corrected as shown below:

<u>Title page,</u>
Item [75], delete the names "Jean Bernard Cazaux, Christine Le Breton and Eric Manginot" as inventors Signed and Sealed this First Day of April, 2003

JAMES E. ROGAN
*Director of the United States Patent and Trademark Office*